(12) United States Patent
Miyake et al.

(10) Patent No.: US 11,414,368 B2
(45) Date of Patent: Aug. 16, 2022

(54) DIALKOXYALKENYL ALKOXYMETHYL ETHER COMPOUND AND A PROCESS FOR PREPARING A TERMINAL CONJUGATED ALKADIENAL COMPOUND FROM THE SAME

(71) Applicant: Shin-Etsu Chemical Co., Ltd., Tokyo (JP)

(72) Inventors: Yuki Miyake, Joetsu (JP); Takeshi Kinsho, Niigata (JP); Shogo Tsukaguchi, Niigata (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 17/489,898

(22) Filed: Sep. 30, 2021

(65) Prior Publication Data

US 2022/0106247 A1    Apr. 7, 2022

(30) Foreign Application Priority Data

Oct. 2, 2020   (JP) .............................. JP2020-167451

(51) Int. Cl.
  *C07C 43/15*   (2006.01)
  *C07C 45/42*   (2006.01)
  *C07C 47/00*   (2006.01)
  *C07C 47/21*   (2006.01)

(52) U.S. Cl.
  CPC .................................. *C07C 47/21* (2013.01)

(58) Field of Classification Search
  CPC ........ C07C 43/15; C07C 45/42; C07C 45/515
  See application file for complete search history.

(56) References Cited

FOREIGN PATENT DOCUMENTS

KR        20180056877       5/2018

OTHER PUBLICATIONS

U.S. Appl. No. 17/489,905, Miyake et al., filed Sep. 30, 2021.
U.S. Appl. No. 17/489,908, Miyake et al., filed Sep. 30, 2021.
"Nickel Boride" Encyclopedia of Reagents for Organic Synthesis, vol. 6, pp. 3694-3699 (2001).
Abstracts of the 1st Latin American Meeting of Chemical Ecology, Colonia del Sacramento, Uruguay (200 pages) (Oct. 17-20, 2010).
Legrand et al. "Synthesis and Field Tests of Sex Pheromone Components of the Leafroller *Argyrotaenia sphaleropa*" Z Naturforsch C J Biosci., 59(9-10):708-712 (2004).
Mozuraitis et al. "Identification of Minor Sex Pheromone Components of the Poplar Clearwing Moth *Paranthrene tabaniformis* (Lepidoptera, Sesiidae)" Zeitschrift für Naturforschung C, 62:138-142 (2007).
Naka et al. "Synthesis and Characterization of 3,13- and 2,13-Octadecadienyl Compounds for Identification of the Sex Pheromone Secreted by a Clearwing Moth, *Nokona pernix*" Bioscience, Biotechnology, and Biochemistry, 70(2):508-516 (2006).
Nielsen et al. "Response of Male Clearwing Moths to Caged Virgin Females, Female Extracts, and Synthetic Sex Attractants" Environmental Entomology, 4(3):451-454 (1975).
Vickers et al. "Sex pheromone components of the clearwing borer, *Carmenta chrysophanes* (Meyrick) (Lepidoptera: Sesiidae): Provisional identification and field tests" Australian Journal of Entomology, 40:69-73 (2001).
Wakamura et al. "Sex pheromone of the blue-striped nettle grub moth *Parasa lepida* (Cramer) (Lepidoptera: Limacodidae): Identification and field attraction" Applied Entomology and Zoology, 42(3):347-352 (2007).
Yadav et al. "Short and Stereoselective Syntheses of Pheromone Components of Aproaerema Modicella" Synthetic Communications, 25(24):4035-4043 (1995).
Sasaerila et al. "Identification of Sex Pheromone Components of Nettle Caterpillar, *Setothosea asigna*" Journal of Chemical Ecology, 23(9):2187-2196 (1997).
Sasaerila et al. "Sex Pheromone Components of Nettle Caterpillar, *Setora nitens*" Journal of Chemical Ecology, 26(8):1983-1990 (2000).
Siderhurst et al. "n-Butyl (E)-7,9-decadienoate: sex pheromone component of the nettle caterpillar, *Darna pallivitta*" Entomologia Experimentalis et Applicata, 125:63-69 (2007).

*Primary Examiner* — Sikarl A Witherspoon
(74) *Attorney, Agent, or Firm* — Myers Bigel, P.A.

(57) ABSTRACT

The present invention provides a process for preparing a terminal conjugated alkadienal compound of the following general formula (5):

$$CH_2=CHCH=CH(CH_2)_aCHO \quad (5)$$

wherein "a" represents an integer of 1 to 15, from a dialkoxyalkenyl alkoxymethyl ether compound of the following general formula (1):

$$R^1CH_2OCH_2OCH_2CH_2CH=CH(CH_2)_aCH(OR^2)(OR^3) \quad (1)$$

wherein $R^1$ represents a hydrogen atom, an n-alkyl group having 1 to 9 carbon atoms, or a phenyl group, $R^2$ and $R^3$ represent, independently of each other, a monovalent hydrocarbon group having 1 to 15 carbon atoms, or $R^2$ and $R^3$ may form together a divalent hydrocarbon group, $R^2$-$R^3$, having 2 to 10 carbon atoms, and "a" is as defined above.

4 Claims, No Drawings

DIALKOXYALKENYL ALKOXYMETHYL ETHER COMPOUND AND A PROCESS FOR PREPARING A TERMINAL CONJUGATED ALKADIENAL COMPOUND FROM THE SAME

TECHNICAL FIELD

The present invention relates to a dialkoxyalkenyl alkoxymethyl ether compound and a process for preparing a terminal conjugated alkadienal compound from the same.

BACKGROUND ART

Nettle caterpillar, *Setothosea asigna* and *Setora nitens*, are serious pests against oil palms in southeast Asia such as Indonesia and Malaysia. These pests eat palm leaves to seriously reduce a yield of oil palms, which is a major problem in plantations. In addition, types of pesticides that can be used are limited for reducing an environmental load and managing health of workers in plantations, which makes effective prevention of the pests difficult. Biological controls have been attracting attention, and utilization of sex pheromones is expected as one of them.

It is reported that a sex pheromone of *Setothosea asigna* is a mixture of (9E)-9-dodecenal and (9E)-9,11-dodecadienal which is one of terminal conjugated alkadienal compounds (Non-Patent Literature 1 listed below). Further, it is reported that a sex pheromone of *Setora nitens* is a mixture of (9Z)-9-dodecenal and (9Z)-9,11-dodecadienal which is one of terminal conjugated alkadienal compounds (Non-Patent Literature 2 listed below).

A process for preparing (9E)-9,11-dodecadienal, sex pheromon of *Setothosea asigna*, is described, for example, in Non-Patent Literature 1 listed below, wherein 3-sulfolene is subjected to alkylation, desulfurization, and removal of THP to obtain (9E)-9,11-dodecadienol, which is then subjected to oxidation with pyridinium chlorochromate (PCC) to oxidize the hydroxyl group (Non-Patent Literature 1).

A process for preparing (9Z)-9,11-dodecadienal, sex pheromon of *Setora nitens*, is described in Non-Patent Literature 2, wherein the resultant mixture, obtained in the process described in Non-Patent Literature 1 and comprising (9E)-9,11-dodecadienol and (9Z)-9,11-dodecadienol, is subjected to a Diels-Alder reaction with tetracyanoethylene (TCNE) wherein the E-form is selectively converted into a certain compound, then the remaining (9Z)-9,11-dodecadienol in a small amount is recovered and its hydroxyl group is oxidized with pyridinium chlorochromate (PCC).

LIST OF THE LITERATURES

Non-Patent Literature

[Non-Patent Literature 1] Gerhard, Gries et al., 1997, J. Chem. Ecol. 23 (9): 2187-2196.

[Non-Patent Literature 2] Gerhard Gries et al., 2000, J. Chem. Ecol. 26 (8): 1983-1990.

[Non-Patent Literature 3] Mathew S. Sidehurst et al., 2007, Entomologia Experimentalis et Applicata, 125: 63-69.

Problems to be Solved by the Invention

However, the processes described in Non-Patent Literatures 1 and 2 utilize alkylation of 3-sulfolene as a key reaction. This reaction requires a large amount of carcinogenic hexamethylphosphoryl triamide as a solvent, and also an expensive reagent, lithium(bistrimethylsilyl)amide (LHMDS). The reaction further requires a special equipment to carry out the reaction at a low temperature. Accordingly, the processes are not industrially advantageous.

In the process described in Non-Patent Literature 1 for obtaining the E-form, an approximately 4% of a geometrical isomer, Z-form, is by-produced in the desulfurization reaction of forming a terminal conjugated diene, so that geometric selectivity is poor (Non-Patent Literature 3 listed above).

The processes described in Non-Patent Literatures 1 and 2 comprise the reactions accompanied with large environmental loads, such as desulfurization in which sulfur dioxide generates, and a PCC oxidation reaction using chromium. Further, the oxidation reaction often involves a risk of explosion and, therefore, is difficult to practice in an industrial scale.

The process of synthesizing (9Z)-9,11-dodecadienal reported in Non-Patent Literature 2 uses tetracyanoethylene (TCNE) which generates highly toxic hydrogen cyanide upon decomposed and, therefore, is unfavorable for industrial application. In addition, only a small amount of (9Z)-9,11-dodecadienol is obtained together with (9E)-9,11-dodecadienol, which lessens a yield of the desired product; and a compound formed from (9Z)-9,11-dodecadienol in a Diels-Alder reaction with TCNE is discarded. Accordingly, the process is inefficient and industrially unpractical as a process for preparing a Z-foam.

The present invention has been made in these circumstances, and aims to provide a process for efficiently preparing a terminal conjugated alkadien-1-yl-acetate compound with high geometrical selectivity.

SUMMARY OF THE INVENTION

As a result of the intensive researches to overcome the aforesaid problems of the prior art, the present inventors have found that a dialkoxyalkenyl alkoxymethyl ether compound is a useful intermediate for the preparation of a terminal conjugated alkadienal compound. The present inventors have also found that the terminal conjugated alkadienal compound is efficiently prepared with high geometrical selectivity from the dialkoxyalkenyl alkoxymethyl ether compound which is a common intermediate for preparing a terminal conjugated alkadienal compound, by constructing the geometry at the internal double bond of the terminal conjugated alkadienal compound by utilizing the reaction-dependent property that the geometry at the double bond of the dialkoxyalkenyl alkoxymethyl ether compound can be E- or Z-selectively constructed, and thus have completed the present invention.

According to one aspect of the present invention, there is provided a process for preparing a terminal conjugated alkadienal compound of the following general formula (5):

$$CH_2=CHCH=CH(CH_2)_aCHO \qquad (5)$$

wherein "a" represents an integer of 1 to 15,
the process comprising:
dealkoxymethylating a dialkoxyalkenyl alkoxymethyl ether compound of the following general formula (1):

$$R^1CH_2OCH_2OCH_2CH_2CH=CH(CH_2)_aCH(OR^2)(OR^3) \qquad (1)$$

wherein $R^1$ represents a hydrogen atom, an n-alkyl group having 1 to 9 carbon atoms, or a phenyl group, $R^2$ and $R^3$ represent, independently of each other, a monovalent hydrocarbon group having 1 to 15 carbon atoms, or $R^2$ and $R^3$ may form together a divalent hydrocarbon group, $R^2$-$R^3$, having 2 to 10 carbon atoms, and "a" is as defined above, to prepare a dialkoxy-3-alken-1-ol compound of the following general formula (2):

$$HOCH_2CH_2CH=CH(CH_2)_aCH(OR^4)(OR^5) \quad (2)$$

wherein $R^4$ and $R^5$ represent, independently of each other, a monovalent hydrocarbon group having 1 to 15 carbon atoms, or $R^4$ and $R^5$ may form together a divalent hydrocarbon group, $R^4$-$R^5$, having 2 to 10 carbon atoms, and "a" is as defined above;

halogenating the dialkoxy-3-alken-1-ol compound (2) to prepare a 1-halodialkoxy-3-alkene compound of the following general formula (3):

$$XCH_2CH_2CH=CH(CH_2)_aCH(OR^4)(OR^5) \quad (3)$$

wherein X represents a halogen atom, and $R^4$, $R^5$ and "a" are as defined above;

subjecting the 1-halodialkoxy-3-alkene compound (3) to an elimination reaction in the presence of a base to prepare a dialkoxy-1,3-alkadiene compound of the following general formula (4):

$$CH_2=CHCH=CH(CH_2)_aCH(OR^4)(OR^5) \quad (4)$$

wherein $R^4$, $R^5$ and "a" are as defined above; and hydrolyzing the dialkoxy-1,3-alkadiene compound (4) to obtain the terminal conjugated alkadienal compound (5).

According to another aspect of the present invention, there is provided a dialkoxyalkenyl alkoxymethyl ether compound of the following general formula (1):

$$R^1CH_2OCH_2OCH_2CH_2CH=CH(CH_2)_aCH(OR^2)(OR^3) \quad (1)$$

wherein $R^1$ represents a hydrogen atom, an n-alkyl group having 1 to 9 carbon atoms, or a phenyl group, $R^2$ and $R^3$ represent, independently of each other, a monovalent hydrocarbon group having 1 to 15 carbon atoms, or $R^2$ and $R^3$ may form together a divalent hydrocarbon group, $R^2$-$R^3$, having 2 to 10 carbon atoms, and "a" represents an integer of 1 to 15.

According to the present invention, the terminal conjugated alkadienal compound (5) can be efficiently prepared with high geometrical selectivity without an oxidation reaction. Furthermore, the terminal conjugated alkadienal compound (5) in E- and Z-form can be prepared from the dialkoxyalkenyl alkoxymethyl ether compound as a common intermediate.

DETAILED DESCRIPTION OF THE
PREFERRED EMBODIMENTS

Dialkoxyalkenyl Alkoxymethyl Ether Compound

First, the dialkoxyalkenyl alkoxymethyl ether compound of the following general formula (1) will be explained below.

$$R^1CH_2OCH_2OCH_2CH=CH(CH_2)_aCH(OR^2)(OR^3) \quad (1)$$

wherein $R^1$ represents a hydrogen atom, an n-alkyl group having 1 to 9 carbon atoms, preferably 1 to 5 carbon atoms, more preferably 1 to 2 carbon atoms, or a phenyl group.

Examples of the n-alkyl group, $R^1$, include linear saturated hydrocarbon groups such as a methyl group, an ethyl group, an n-propyl group, an n-butyl group, an n-pentyl group, an n-hexyl group, an n-heptyl group, an n-octyl group, and an n-nonyl group.

$R^2$ and $R^3$ represent, independently of each other, a monovalent hydrocarbon group having 1 to 15 carbon atoms, preferably 1 to 10 carbon atoms, more preferably 1 to 4 carbon atoms, or $R^2$ and $R^3$ may form together a divalent hydrocarbon group, $R^2$-$R^3$, having 2 to 10 carbon atoms, preferably 2 to 4 carbon atoms.

Examples of the monovalent hydrocarbon group, $R^2$ and $R^3$, include linear saturated hydrocarbon groups such as a methyl group, an ethyl group, an n-propyl group, an n-butyl group, an n-pentyl group, an n-hexyl group, an n-heptyl group, an n-octyl group, an n-nonyl group, an n-decyl group, an n-undecyl group, and an n-dodecyl group; branched saturated hydrocarbon groups such as an isopropyl group, a 2-isobutyl group, and a 2-methylbutyl group; linear unsaturated hydrocarbon groups such as a 2-propenyl group; branched unsaturated hydrocarbon groups such as a 2-methyl-2-propenyl group; cyclic saturated hydrocarbon groups such as a cyclopropyl group; and isomers thereof. A part of the hydrogen atoms of the hydrocarbon group may be substituted with a methyl group or an ethyl group.

The monovalent hydrocarbon group is preferably a methyl group, an ethyl group, an n-propyl group, or an n-butyl group in view of the handling.

Examples of the divalent hydrocarbon group include linear saturated hydrocarbon groups such as an ethylene group, a 1,3-propylene group, and a 1,4-butylene group; branched saturated hydrocarbon groups such as a 1,2-propylene group, a 2,2-dimethyl-1,3-propylene group, a 1,2-butylene group, a 1,3-butylene group, a 2,3-butylene group, and a 2,3-dimethyl-2,3-butylene group; linear unsaturated hydrocarbon groups such as a 1-vinylethylene group; branched unsaturated hydrocarbon groups such as a 2-methylene-1,3-propylene group; cyclic hydrocarbon groups such as a 1,2-cyclopropylene group and a 1,2-cyclobutylene group; and isomers thereof. A part of the hydrogen atoms in the hydrocarbon groups may be substituted with a methyl group or an ethyl group.

The divalent hydrocarbon group is preferably a lower hydrocarbon group (preferably having 2 to 4 carbon atoms) because these are highly reactive in the deprotection, are easily purified, and are easily available, and a by-product formed in the deprotection is easily removed by washing with water or concentration.

Considering these, examples of the more preferable divalent hydrocarbon group include an ethylene group, a 1,3-propylene group, a 1,2-propylene group, a 1,2-butylene group, a 1,3-butylene group, and a 2,3-dimethyl-2,3-butylene group.

"a" represents an integer of 1 to 15, preferably 3 to 13, more preferably 5 to 11, for easy preparing a pheromon of lepidopteran pests.

When "a" represents an integer of 7, the dialkoxyalkenyl alkoxymethyl ether compound (1) is a dialkoxydodecenyl alkoxymethyl ether compound (1: a=7). The dialkoxydodecenyl alkoxymethyl ether compound (1: a=7) is useful in preparing (9E)-9,11-dodecadienal, sex pheromon of *Setothosea asigna,* and (9Z)-9,11-dodecadienal, sex pheromon of *Setora nitens*.

Specific examples of the dialkoxyalkenyl alkoxymethyl ether compound (1) include the following compounds:

dialkoxyhexenyl methoxymethyl ether compounds such as dimethoxyhexenyl methoxymethyl ether, diethoxyhexenyl methoxymethyl ether, dipropoxyhexenyl methoxymethyl ether, dibutoxyhexenyl methoxymethyl ether, dipentyloxyhexenyl methoxymethyl ether, dihexyloxyhexenyl methoxymethyl ether, diheptyloxyhexenyl methoxymethyl ether, dioctyloxyhexenyl methoxymethyl ether, dinonyloxyhexenyl methoxymethyl ether, and didecyloxyhexenyl methoxymethyl ether;

dialkoxyheptenyl methoxymethyl ether compounds such as dimethoxyheptenyl methoxymethyl ether, diethoxyheptenyl methoxymethyl ether, dipropoxyheptenyl methoxymethyl ether, dibutoxyheptenyl methoxymethyl ether, dipentyloxyheptenyl methoxymethyl ether, dihexyloxyheptenyl methoxymethyl ether, diheptyloxyheptenyl methoxymethyl ether, dioctyloxyheptenyl methoxymethyl ether, dinonyloxyheptenyl methoxymethyl ether, and didecyloxyheptenyl methoxymethyl ether;

dialkoxyheptenyl ethoxymethyl ether compounds such as dimethoxyheptenyl ethoxymethyl ether, diethoxyheptenyl ethoxymethyl ether, dipropoxyheptenyl ethoxymethyl ether, dibutoxyheptenyl ethoxymethyl ether, dipentyloxyheptenyl ethoxymethyl ether, dihexyloxyheptenyl ethoxymethyl ether, diheptyloxyheptenyl ethoxymethyl ether, dioctyloxyheptenyl ethoxymethyl ether, dinonyloxyheptenyl ethoxymethyl ether, and didecyloxyheptenyl ethoxymethyl ether;

dialkoxyheptenyl propoxymethyl ether compounds such as dimethoxyheptenyl propoxymethyl ether, diethoxyheptenyl propoxymethyl ether, dipropoxyheptenyl propoxymethyl ether, dibutoxyheptenyl propoxymethyl ether, dipentyloxyheptenyl propoxymethyl ether, dihexyloxyheptenyl propoxymethyl ether, diheptyloxyheptenyl propoxymethyl ether, dioctyloxyheptenyl propoxymethyl ether, dinonyloxyheptenyl propoxymethyl ether, and didecyloxyheptenyl propoxymethyl ether;

dialkoxyheptenyl butoxymethyl ether compounds such as dimethoxyheptenyl butoxymethyl ether, diethoxyheptenyl butoxymethyl ether, dipropoxyheptenyl butoxymethyl ether, dibutoxyheptenyl butoxymethyl ether, dipentyloxyheptenyl butoxymethyl ether, dihexyloxyheptenyl butoxymethyl ether, diheptyloxyheptenyl butoxymethyl ether, dioctyloxyheptenyl butoxymethyl ether, dinonyloxyheptenyl butoxymethyl ether, and didecyloxyheptenyl butoxymethyl ether;

dialkoxyheptenyl pentyloxymethyl ether compounds such as dimethoxyheptenyl pentyloxymethyl ether, diethoxyheptenyl pentyloxymethyl ether, dipropoxyheptenyl pentyloxymethyl ether, dibutoxyheptenyl pentyloxymethyl ether, dipentyloxyheptenyl pentyloxymethyl ether, dihexyloxyheptenyl pentyloxymethyl ether, diheptyloxyheptenyl pentyloxymethyl ether, dioctyloxyheptenyl pentyloxymethyl ether, dinonyloxyheptenyl pentyloxymethyl ether, and didecyloxyheptenyl pentyloxymethyl ether;

dialkoxyheptenyl hexyloxymethyl ether compounds such as dimethoxyheptenyl hexyloxymethyl ether, diethoxyheptenyl hexyloxymethyl ether, dipropoxyheptenyl hexyloxymethyl ether, dibutoxyheptenyl hexyloxymethyl ether, dipentyloxyheptenyl hexyloxymethyl ether, dihexyloxyheptenyl hexyloxymethyl ether, diheptyloxyheptenyl hexyloxymethyl ether, dioctyloxyheptenyl hexyloxymethyl ether, dinonyloxyheptenyl hexyloxymethyl ether, and didecyloxyheptenyl hexyloxymethyl ether;

dialkoxyheptenyl heptyloxymethyl ether compounds such as dimethoxyheptenyl heptyloxymethyl ether, diethoxyheptenyl heptyloxymethyl ether, dipropoxyheptenyl heptyloxymethyl ether, dibutoxyheptenyl heptyloxymethyl ether, dipentyloxyheptenyl heptyloxymethyl ether, dihexyloxyheptenyl heptyloxymethyl ether, diheptyloxyheptenyl heptyloxymethyl ether, dioctyloxyheptenyl heptyloxymethyl ether, dinonyloxyheptenyl heptyloxymethyl ether, and didecyloxyheptenyl heptyloxymethyl ether;

dialkoxyheptenyl octyloxymethyl ether compounds such as dimethoxyheptenyl octyloxymethyl ether, diethoxyheptenyl octyloxymethyl ether, dipropoxyheptenyl octyloxymethyl ether, dibutoxyheptenyl octyloxymethyl ether, dipentyloxyheptenyl octyloxymethyl ether, dihexyloxyheptenyl octyloxymethyl ether, diheptyloxyheptenyl octyloxymethyl ether, dioctyloxyheptenyl octyloxymethyl ether, dinonyloxyheptenyl octyloxymethyl ether; and didecyloxyheptenyl octyloxymethyl ether;

dialkoxyheptenyl nonyloxymethyl ether compounds such as dimethoxyheptenyl nonyloxymethyl ether, diethoxyheptenyl nonyloxymethyl ether, dipropoxyheptenyl nonyloxymethyl ether, dibutoxyheptenyl nonyloxymethyl ether, dipentyloxyheptenyl nonyloxymethyl ether, dihexyloxyheptenyl nonyloxymethyl ether, diheptyloxyheptenyl nonyloxymethyl ether, dioctyloxyheptenyl nonyloxymethyl ether, dinonyloxyheptenyl nonyloxymethyl ether, and didecyloxyheptenyl nonyloxymethyl ether;

dialkoxyheptenyl decyloxymethyl ether compounds such as dimethoxyheptenyl decyloxymethyl ether, diethoxyheptenyl decyloxymethyl ether, dipropoxyheptenyl decyloxymethyl ether, dibutoxyheptenyl decyloxymethyl ether, dipentyloxyheptenyl decyloxymethyl ether, dihexyloxyheptenyl decyloxymethyl ether, diheptyloxyheptenyl decyloxymethyl ether, dioctyloxyheptenyl decyloxymethyl ether, dinonyloxyheptenyl decyloxymethyl ether, and didecyloxyheptenyl decyloxymethyl ether;

dialkoxyheptenyl benzyloxymethyl ether compounds such as dimethoxyheptenyl benzyloxymethyl ether, diethoxyheptenyl benzyloxymethyl ether, dipropoxyheptenyl benzyloxymethyl ether, dibutoxyheptenyl benzyloxymethyl ether, dipentyloxyheptenyl benzyloxymethyl ether, dihexyloxyheptenyl benzyloxymethyl ether, diheptyloxyheptenyl benzyloxymethyl ether, dioctyloxyheptenyl benzyloxymethyl ether, dinonyloxyheptenyl benzyloxymethyl ether, and didecyloxyheptenyl benzyloxymethyl ether;

dialkoxyoctenyl alkoxymethyl ether compounds such as dimethoxyoctenyl methoxymethyl ether, diethoxyoctenyl methoxymethyl ether, dipropoxyoctenyl methoxymethyl ether, dibutoxyoctenyl methoxymethyl ether, dipentyloxyoctenyl methoxymethyl ether, dihexyloxyoctenyl methoxymethyl ether, diheptyloxyoctenyl methoxymethyl ether, dioctyloxyoctenyl methoxymethyl ether, dinonyloxyoctenyl methoxymethyl ether, and didecyloxyoctenyl methoxymethyl ether;

dialkoxynonenyl alkoxymethyl ether compounds such as dimethoxynonenyl methoxymethyl ether, diethoxynonenyl methoxymethyl ether, dipropoxynonenyl methoxymethyl ether, dibutoxynonenyl methoxymethyl ether, dipentyloxynonenyl methoxymethyl ether, dihexyloxynonenyl methoxymethyl ether, diheptyloxynonenyl methoxymethyl ether, dioctyloxynonenyl methoxymethyl ether, dinonyloxynonenyl methoxymethyl ether, and didecyloxynonenyl methoxymethyl ether;

dialkoxydecenyl alkoxymethyl ether compounds such as dimethoxydecenyl methoxymethyl ether, diethoxydecenyl methoxymethyl ether, dipropoxydecenyl methoxymethyl ether, dibutoxydecenyl methoxymethyl ether, dipentyloxydecenyl methoxymethyl ether, dihexyloxydecenyl methoxymethyl ether, diheptyloxydecenyl methoxymethyl ether, dioctyloxydecenyl methoxymethyl ether, dinonyloxydecenyl methoxymethyl ether, and didecyloxydecenyl methoxymethyl ether;

dialkoxyundecenyl alkoxymethyl ether compounds such as dimethoxyundecenyl methoxymethyl ether, diethoxyundecenyl methoxymethyl ether, dipropoxyundecenyl methoxymethyl ether, dibutoxyundecenyl methoxymethyl ether, dipentyloxyundecenyl methoxymethyl ether, dihexyloxyundecenyl methoxymethyl ether, diheptyloxyundecenyl methoxymethyl ether, dioctyloxyundecenyl methoxymethyl ether, dinonyloxyundecenyl methoxymethyl ether, and didecyloxyundecenyl methoxymethyl ether;

dialkoxydodecenyl methoxymethyl ether compounds such as dimethoxydodecenyl methoxymethyl ether, diethoxydodecenyl methoxymethyl ether, dipropoxydodecenyl methoxymethyl ether, dibutoxydodecenyl methoxymethyl ether, dipentyloxydodecenyl methoxymethyl ether, dihexyloxydodecenyl methoxymethyl ether, diheptyloxydodecenyl methoxymethyl ether, dioctyloxydodecenyl methoxymethyl ether, dinonyloxydodecenyl methoxymethyl ether, and didecyloxydodecenyl methoxymethyl ether;

dialkoxydodecenyl ethoxymethyl ether compounds such as dimethoxydodecenyl ethoxymethyl ether, diethoxydodecenyl ethoxymethyl ether, dipropoxydodecenyl ethoxymethyl ether, dibutoxydodecenyl ethoxymethyl ether, dipentyloxydodecenyl ethoxymethyl ether, dihexyloxydodecenyl ethoxymethyl ether, diheptyloxydodecenyl ethoxymethyl ether, dioctyloxydodecenyl ethoxymethyl ether, dinonyloxydodecenyl ethoxymethyl ether, and didecyloxydodecenyl ethoxymethyl ether;

dialkoxydodecenyl propoxymethyl ether compounds such as dimethoxydodecenyl propoxymethyl ether, diethoxydodecenyl propoxymethyl ether, dipropoxydodecenyl propoxymethyl ether, dibutoxydodecenyl propoxymethyl ether, dipentyloxydodecenyl propoxymethyl ether, dihexyloxydodecenyl propoxymethyl ether, diheptyloxydodecenyl propoxymethyl ether, dioctyloxydodecenyl propoxymethyl ether, dinonyloxydodecenyl propoxymethyl ether, and didecyloxydodecenyl propoxymethyl ether;

dialkoxydodecenyl butoxymethyl ether compounds such as dimethoxydodecenyl butoxymethyl ether, diethoxydodecenyl butoxymethyl ether, dipropoxydodecenyl butoxymethyl ether, dibutoxydodecenyl butoxymethyl ether, dipentyloxydodecenyl butoxymethyl ether, dihexyloxydodecenyl butoxymethyl ether, diheptyloxydodecenyl butoxymethyl ether, dioctyloxydodecenyl butoxymethyl ether, dinonyloxydodecenyl butoxymethyl ether, and didecyloxydodecenyl butoxymethyl ether;

dialkoxydodecenyl pentyloxymethyl ether compounds such as dimethoxydodecenyl pentyloxymethyl ether, diethoxydodecenyl pentyloxymethyl ether, dipropoxydodecenyl pentyloxymethyl ether, dibutoxydodecenyl pentyloxymethyl ether, dipentyloxydodecenyl pentyloxymethyl ether, dihexyloxydodecenyl pentyloxymethyl ether, diheptyloxydodecenyl pentyloxymethyl ether, dioctyloxydodecenyl pentyloxymethyl ether, dinonyloxydodecenyl pentyloxymethyl ether, and didecyloxydodecenyl pentyloxymethyl ether;

dialkoxydodecenyl hexyloxymethyl ether compounds such as dimethoxydodecenyl hexyloxymethyl ether, diethoxydodecenyl hexyloxymethyl ether, dipropoxydodecenyl hexyloxymethyl ether, dibutoxydodecenyl hexyloxymethyl ether, dipentyloxydodecenyl hexyloxymethyl ether, dihexyloxydodecenyl hexyloxymethyl ether, diheptyloxydodecenyl hexyloxymethyl ether, dioctyloxydodecenyl hexyloxymethyl ether, dinonyloxydodecenyl hexyloxymethyl ether, and didecyloxydodecenyl hexyloxymethyl ether;

dialkoxydodecenyl heptyloxymethyl ether compounds such as dimethoxydodecenyl heptyloxymethyl ether, diethoxydodecenyl heptyloxymethyl ether, dipropoxydodecenyl heptyloxymethyl ether, dibutoxydodecenyl heptyloxymethyl ether, dipentyloxydodecenyl heptyloxymethyl ether, dihexyloxydodecenyl heptyloxymethyl ether, diheptyloxydodecenyl heptyloxymethyl ether, dioctyloxydodecenyl heptyloxymethyl ether, dinonyloxydodecenyl heptyloxymethyl ether, and didecyloxydodecenyl heptyloxymethyl ether;

dialkoxydodecenyl octyloxymethyl ether compounds such as dimethoxydodecenyl octyloxymethyl ether, diethoxydodecenyl octyloxymethyl ether, dipropoxydodecenyl octyloxymethyl ether, dibutoxydodecenyl octyloxymethyl ether, dipentyloxydodecenyl octyloxymethyl ether, dihexyloxydodecenyl octyloxymethyl ether, diheptyloxydodecenyl octyloxymethyl ether, dioctyloxydodecenyl octyloxymethyl ether, dinonyloxydodecenyl octyloxymethyl ether, and didecyloxydodecenyl octyloxymethyl ether;

dialkoxydodecenyl nonyloxymethyl ether compounds such as dimethoxydodecenyl nonyloxymethyl ether, diethoxydodecenyl nonyloxymethyl ether, dipropoxydodecenyl nonyloxymethyl ether, dibutoxydodecenyl nonyloxymethyl ether, dipentyloxydodecenyl nonyloxymethyl ether, dihexyloxydodecenyl nonyloxymethyl ether, diheptyloxydodecenyl nonyloxymethyl ether, dioctyloxydodecenyl nonyloxymethyl ether, dinonyloxydodecenyl nonyloxymethyl ether, and didecyloxydodecenyl nonyloxymethyl ether;

dialkoxydodecenyl decyloxymethyl ether compounds such as dimethoxydodecenyl decyloxymethyl ether, diethoxydodecenyl decyloxymethyl ether, dipropoxydodecenyl decyloxymethyl ether, dibutoxydodecenyl decyloxymethyl ether, dipentyloxydodecenyl decyloxymethyl ether, dihexyloxydodecenyl decyloxymethyl ether, diheptyloxydodecenyl decyloxymethyl ether, dioctyloxydodecenyl decyloxymethyl ether, dinonyloxydodecenyl decyloxymethyl ether, and didecyloxydodecenyl decyloxymethyl ether;

dialkoxydodecenyl benzyloxymethyl ether compounds such as dimethoxydodecenyl benzyloxymethyl ether, diethoxydodecenyl benzyloxymethyl ether, dipropoxydodecenyl benzyloxymethyl ether, dibutoxydodecenyl benzyloxymethyl ether, dipentyloxydodecenyl benzyloxymethyl ether, dihexyloxydodecenyl benzyloxymethyl ether, diheptyloxydodecenyl benzyloxymethyl ether, dioctyloxydodecenyl benzyloxymethyl ether, dinonyloxydodecenyl benzyloxymethyl ether, and didecyloxydodecenyl benzyloxymethyl ether;

dialkoxytridecenyl alkoxymethyl ether compounds such as dimethoxytridecenyl methoxymethyl ether, diethoxytridecenyl methoxymethyl ether, dipropoxytridecenyl methoxymethyl ether, dibutoxytridecenyl methoxymethyl ether, dipentyloxytridecenyl methoxymethyl ether, dihexyloxytridecenyl methoxymethyl ether, diheptyloxytridecenyl methoxymethyl ether, dioctyloxytridecenyl methoxymethyl ether, dinonyloxytridecenyl methoxymethyl ether, and didecyloxytridecenyl methoxymethyl ether;

dialkoxytetradecenyl methoxymethyl ether compounds such as dimethoxytetradecenyl methoxymethyl ether, diethoxytetradecenyl methoxymethyl ether, dipropoxytetradecenyl methoxymethyl ether, dibutoxytetradecenyl methoxymethyl ether, dipentyloxytetradecenyl methoxymethyl ether, dihexyloxytetradecenyl methoxymethyl ether, diheptyloxytetradecenyl methoxymethyl ether, dioctyloxytetradecenyl methoxymethyl ether, dinonyloxytetradecenyl methoxymethyl ether, and didecyloxytetradecenyl methoxymethyl ether;

dialkoxytetradecenyl ethoxymethyl ether compounds such as dimethoxytetradecenyl ethoxymethyl ether, diethoxytetradecenyl ethoxymethyl ether, dipropoxytetradecenyl ethoxymethyl ether, dibutoxytetradecenyl ethoxymethyl ether, dipentyloxytetradecenyl ethoxymethyl ether, dihexyloxytetradecenyl ethoxymethyl ether, diheptyloxytetradecenyl ethoxymethyl ether, dioctyloxytetradecenyl ethoxymethyl ether, dinonyloxytetradecenyl ethoxymethyl ether, and didecyloxytetradecenyl ethoxymethyl ether;

dialkoxytetradecenyl propoxymethyl ether compounds such as dimethoxytetradecenyl propoxymethyl ether, diethoxytetradecenyl propoxymethyl ether, dipropoxytetradecenyl propoxymethyl ether, dibutoxytetradecenyl propoxymethyl ether, dipentyloxytetradecenyl propoxymethyl ether, dihexyloxytetradecenyl propoxymethyl ether, diheptyloxytetradecenyl propoxymethyl ether, dioctyloxytetradecenyl propoxymethyl ether, dinonyloxytetradecenyl propoxymethyl ether, and didecyloxytetradecenyl propoxymethyl ether;

dialkoxytetradecenyl butoxymethyl ether compounds such as dimethoxytetradecenyl butoxymethyl ether, diethoxytetradecenyl butoxymethyl ether, dipropoxytetradecenyl butoxymethyl ether, dibutoxytetradecenyl butoxymethyl ether, dipentyloxytetradecenyl butoxymethyl ether, dihexyloxytetradecenyl butoxymethyl ether, diheptyloxytetradecenyl butoxymethyl ether, dioctyloxytetradecenyl butoxymethyl ether, dinonyloxytetradecenyl butoxymethyl ether, and didecyloxytetradecenyl butoxymethyl ether;

dialkoxytetradecenyl pentyloxymethyl ether compounds such as dimethoxytetradecenyl pentyloxymethyl ether, diethoxytetradecenyl pentyloxymethyl ether, dipropoxytetradecenyl pentyloxymethyl ether, dibutoxytetradecenyl pentyloxymethyl ether, dipentyloxytetradecenyl pentyloxymethyl ether, dihexyloxytetradecenyl pentyloxymethyl ether, diheptyloxytetradecenyl pentyloxymethyl ether, dioctyloxytetradecenyl pentyloxymethyl ether, dinonyloxytetradecenyl pentyloxymethyl ether, and didecyloxytetradecenyl pentyloxymethyl ether;

dialkoxytetradecenyl hexyloxymethyl ether compounds such as dimethoxytetradecenyl hexyloxymethyl ether, diethoxytetradecenyl hexyloxymethyl ether, dipropoxytetradecenyl hexyloxymethyl ether, dibutoxytetradecenyl hexyloxymethyl ether, dipentyloxytetradecenyl hexyloxymethyl ether, dihexyloxytetradecenyl hexyloxymethyl ether, diheptyloxytetradecenyl hexyloxymethyl ether, dioctyloxytetradecenyl hexyloxymethyl ether, dinonyloxytetradecenyl hexyloxymethyl ether, and didecyloxytetradecenyl hexyloxymethyl ether;

dialkoxytetradecenyl heptyloxymethyl ether compounds such as dimethoxytetradecenyl heptyloxymethyl ether, diethoxytetradecenyl heptyloxymethyl ether, dipropoxytetradecenyl heptyloxymethyl ether, dibutoxytetradecenyl heptyloxymethyl ether, dipentyloxytetradecenyl heptyloxymethyl ether, dihexyloxytetradecenyl heptyloxymethyl ether, diheptyloxytetradecenyl heptyloxymethyl ether, dioctyloxytetradecenyl heptyloxymethyl ether, dinonyloxytetradecenyl heptyloxymethyl ether, and didecyloxytetradecenyl heptyloxymethyl ether;

dialkoxytetradecenyl octyloxymethyl ether compounds such as dimethoxytetradecenyl octyloxymethyl ether, diethoxytetradecenyl octyloxymethyl ether, dipropoxytetradecenyl octyloxymethyl ether, dibutoxytetradecenyl octyloxymethyl ether, dipentyloxytetradecenyl octyloxymethyl ether, dihexyloxytetradecenyl octyloxymethyl ether, diheptyloxytetradecenyl octyloxymethyl ether, dioctyloxytetradecenyl octyloxymethyl ether, dinonyloxytetradecenyl octyloxymethyl ether, and didecyloxytetradecenyl octyloxymethyl ether;

dialkoxytetradecenyl nonyloxymethyl ether compounds such as dimethoxytetradecenyl nonyloxymethyl ether, diethoxytetradecenyl nonyloxymethyl ether, dipropoxytetradecenyl nonyloxymethyl ether, dibutoxytetradecenyl nonyloxymethyl ether, dipentyloxytetradecenyl nonyloxymethyl ether, dihexyloxytetradecenyl nonyloxymethyl ether, diheptyloxytetradecenyl nonyloxymethyl ether, dioctyloxytetradecenyl nonyloxymethyl ether, dinonyloxytetradecenyl nonyloxymethyl ether, and didecyloxytetradecenyl nonyloxymethyl ether;

dialkoxytetradecenyl decyloxymethyl ether compounds such as dimethoxytetradecenyl decyloxymethyl ether, diethoxytetradecenyl decyloxymethyl ether, dipropoxytetradecenyl decyloxymethyl ether, dibutoxytetradecenyl decyloxymethyl ether, dipentyloxytetradecenyl decyloxymethyl ether, dihexyloxytetradecenyl decyloxymethyl ether, diheptyloxytetradecenyl decyloxymethyl ether, dioctyloxytetradecenyl decyloxymethyl ether, dinonyloxytetradecenyl decyloxymethyl ether, and didecyloxytetradecenyl decyloxymethyl ether;

dialkoxytetradecenyl benzyloxymethyl ether compounds such as dimethoxytetradecenyl benzyloxymethyl ether, diethoxytetradecenyl benzyloxymethyl ether, dipropoxytetradecenyl benzyloxymethyl ether, dibutoxytetradecenyl benzyloxymethyl ether, dipentyloxytetradecenyl benzyloxymethyl ether, dihexyloxytetradecenyl benzyloxymethyl ether, diheptyloxytetradecenyl benzyloxymethyl ether, dioctyloxytetradecenyl benzyloxymethyl ether, dinonyloxytetradecenyl benzyloxymethyl ether, and didecyloxytetradecenyl benzyloxymethyl ether;

dialkoxypentadecenyl methoxymethyl ether compounds such as dimethoxypentadecenyl methoxymethyl ether, diethoxypentadecenyl methoxymethyl ether, dipropoxypentadecenyl methoxymethyl ether, dibutoxypentadecenyl methoxymethyl ether, dipentyloxypentadecenyl methoxymethyl ether, dihexyloxypentadecenyl methoxymethyl ether, diheptyloxypentadecenyl methoxymethyl ether, dioctyloxypentadecenyl methoxymethyl ether, dinonyloxypentadecenyl methoxymethyl ether, and didecyloxypentadecenyl methoxymethyl ether;

dialkoxyhexadecenyl methoxymethyl ether compounds such as dimethoxyhexadecenyl methoxymethyl ether, diethoxyhexadecenyl methoxymethyl ether, dipropoxyhexadecenyl methoxymethyl ether, dibutoxyhexadecenyl methoxymethyl ether, dipentyloxyhexadecenyl methoxymethyl ether, dihexyloxyhexadecenyl methoxymethyl ether, diheptyloxyhexadecenyl methoxymethyl ether, dioctyloxyhexadecenyl methoxymethyl ether, dinonyloxyhexadecenyl methoxymethyl ether, and didecyloxyhexadecenyl methoxymethyl ether;

dialkoxyheptadecenyl methoxymethyl ether compounds such as dimethoxyheptadecenyl methoxymethyl ether, diethoxyheptadecenyl methoxymethyl ether, dipropoxyheptadecenyl methoxymethyl ether, dibutoxyheptadecenyl methoxymethyl ether, dipentyloxyheptadecenyl methoxymethyl ether, dihexyloxyheptadecenyl methoxymethyl ether, diheptyloxyheptadecenyl methoxymethyl ether, dioctyloxyheptadecenyl methoxymethyl ether, dinonyloxyheptadecenyl methoxymethyl ether, and didecyloxyheptadecenyl methoxymethyl ether; and dialkoxyoctadecenyl methoxymethyl ether compounds such as dimethoxyoctadecenyl methoxymethyl ether, diethoxyoctadecenyl methoxymethyl ether, dipropoxyoctadecenyl methoxymethyl ether, dibutoxyoctadecenyl methoxymethyl ether, dipentyloxyoctadecenyl methoxymethyl ether, dihexyloxyoctadecenyl methoxymethyl ether, diheptyloxyoctadecenyl methoxymethyl ether, dioctyloxyoctadecenyl methoxymethyl ether, dinonyloxyoctadecenyl methoxymethyl ether, and didecyloxy octadecenyl methoxymethyl ether.

Among these dialkoxyalkenyl alkoxymethyl ether compound (1), the dialkoxydodecenyl alkoxymethyl ether compound (a=7) is preferred for preparing (9E)-9,11-dodecadienal, sex pheromon of *Setothosea asigna,* and (9Z)-9,11-dodecadienal, sex pheromon of *Setora nitens.*

The dialkoxyalkenyl alkoxymethyl ether compound (1) may be synthesized by various synthetic methods shown below, depending on the number "a" in the general formula (1). In the following description of the synthesis method, it should be noted that the description on a compound is not limited only to a case where the compound is prepared according to a specific synthesis method shown below, but applies also to a case where the compound is prepared according to other methods.

When "a" represents an integer of any of 2 and 5 to 15, the dialkoxyalkenyl alkoxymethyl ether compound (1) may be synthesized, for example, according to the following reaction scheme comprising at least 5 steps consisting of the first to third, sixth and seventh steps mentioned below (in a case where "a"=2), or at least 7 steps consisting of the first to seventh steps (in a case where "a"=5 to 15).

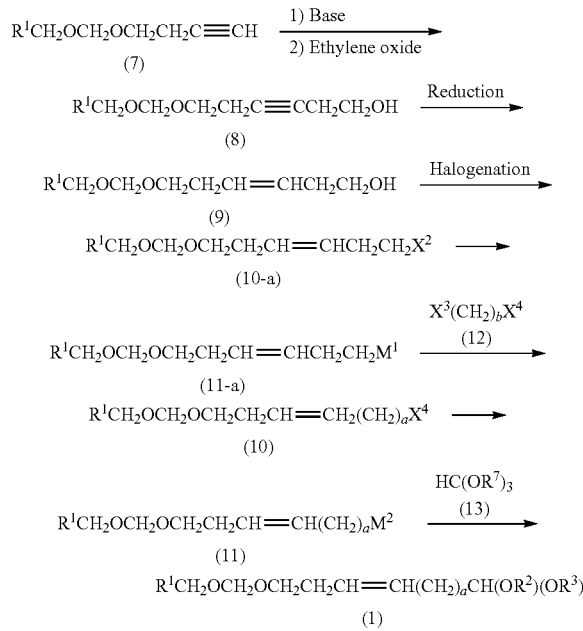

First, an alkoxymethyl 3-butynyl ether compound of the general formula (7) is reacted with a base, and then reacted with ethylene oxide to increase the number of carbon atoms, thereby obtaining a 6-hydroxy-3-hexynyl alkoxymethyl ether compound of the general formula (8) (first step). The carbon-carbon triple bond of the obtained the 6-hydroxy-3-hexynyl alkoxymethyl ether compound (8) is reduced to obtain a 6-hydroxy-3-hexenyl alkoxymethyl ether compound of the general formula (9) (second step). The hydroxyl group of the obtained 6-hydroxy-3-hexenyl alkoxymethyl ether compound (9) is halogenated to obtain a 6-halo-3-hexenyl alkoxymethyl ether compound of the general formula (10-a) (third step). The obtained 6-halo-3-hexenyl alkoxymethyl ether compound (10-a) is reacted with, for example, magnesium or an organolithium reagent in a solvent to obtain a nucleophilic reagent, 6-(alkoxymethoxy)-3-hexenyl compound of the general formula (11-a) (fourth step). Then, the obtained nucleophilic reagent, 6-(alkoxymethoxy)-3-hexenyl compound (11-a), is subjected to a coupling reaction with a dihaloalkane compound of the general formula (12) to obtain a haloalkenyl alkoxymethyl ether compound (10) having the increased number of carbon atoms (fifth step). The obtained haloalkenyl alkoxymethyl ether compound (10) is reacted with, for example, magnesium or an organolithium reagent in a solvent to obtain a nucleophilic reagent, (alkoxymethoxy)-3-alkenyl compound of the general formula (11) (sixth step). Then, the obtained nucleophilic reagent, (alkoxymethoxy)-3-alkenyl compound (11), is subjected to a nucleophilic substitution reaction with an orthoformate ester compound of the general formula (13) for acetalization to obtain the dialkoxyalkenyl alkoxymethyl ether compound (seventh step).

It should be noted that when "a" in the general formula (1) is an integer of 2, it is unnecessary to increase the carbon number by the fifth step. Therefore, the fourth step is directly followed by the seventh step to obtain a dialkoxyalkenyl alkoxymethyl ether compound (1: a=2).

The aforesaid process for preparing the dialkoxyalkenyl alkoxymethyl ether compound (1) will be explained in more detail below.

The alkoxymethyl 3-butynyl ether compound (7) indicated in the aforesaid reaction scheme for preparing the compound (1) from the compound (7) will be explained below.

$R^1$ in the general formula (7) is as defined for the general formula (1).

Specific examples of the alkoxymethyl 3-butynyl ether compound (7) include methoxymethyl 3-butynyl ether, ethoxymethyl 3-butynyl ether, propoxymethyl 3-butynyl ether, butoxymethyl 3-butynyl ether, pentyloxymethyl 3-butynyl ether, hexyloxymethyl 3-butynyl ether, heptyloxymethyl 3-butynyl ether, octyloxymethyl 3-butynyl ether, nonyloxymethyl 3-butynyl ether, decyloxymethyl 3-butynyl ether, and benzyloxymethyl 3-butynyl ether.

Examples of the base used in a homologation reaction include organometallic reagents such as n-butyllithium, tert-butyllithium, methylmagnesium chloride, methylmagnesium bromide, sodium acetylide, and potassium acetylide; and metal hydride reagents such as sodium hydride and potassium hydride. The organometallic reagents are preferred in view of the reactivity.

An amount of the base used is preferably 1.0 to 5.0 mol, more preferably 1.0 to 2.0 mol, per mol of the alkoxymethyl 3-butynyl ether compound (7) in view of the reactivity.

An amount of the ethylene oxide is preferably 1.0 to 10.0 mol, more preferably 1.0 to 3.0 mol, per mol of the alkoxymethyl 3-butynyl ether compound (7) in view of the reactivity.

A solvent may be used in the aforesaid homologation reaction, if necessary.

Examples of the solvent include usual solvents, for example, ethers such as diethyl ether, dibutyl ether, 4-methyltetrahydropyran, tetrahydrofuran (THF), cyclopentylmethylether, and 1,4-dioxane; hydrocarbons such as hexane, heptane, benzene, toluene, xylene, and cumene; chlorinated solvents such as trichloroethylene, dichloromethane, and chloroform; aprotic polar solvents such as dimethyl sulfoxide, γ-butyrolactone (GBL), N-methylpyrrolidone, N,N-dimethylformamide, N,N-dimethylacetamide, and hexamethylphosphoric triamide; and nitriles such as acetonitrile and propionitrile, with ethers such as diethyl ether, tetrahydrofuran, and 4-methyltetrahydropyran being preferred in view of the reactivity.

The solvent may be used alone or in combination thereof, if necessary. The solvent may be commercially available one.

An amount of the solvent is preferably 50 to 3,000 g, more preferably 100 to 1,200 g, per mol of the alkoxymethyl 3-butynyl ether compound (7) in view of the reactivity.

The 6-hydroxy-3-hexynyl alkoxymethyl ether compound (8) indicated in the aforesaid reaction scheme for preparing the compound (1) from the compound (7) will be explained below.

$R^1$ in the general formula (8) is as defined for the general formula (1).

Specific examples of the 6-hydroxy-3-hexynyl alkoxymethyl ether compound (8) include 6-hydroxy-3-hexynyl methoxymethyl ether, 6-hydroxy-3-hexynyl ethoxymethyl ether, 6-hydroxy-3-hexynyl propoxymethyl ether, 6-hydroxy-3-hexynyl butoxymethyl ether, 6-hydroxy-3-hexynyl pentyloxymethyl ether, 6-hydroxy-3-hexynyl hexyloxymethyl ether, 6-hydroxy-3-hexynyl heptyloxymethyl ether, 6-hydroxy-3-hexynyl octyloxymethyl ether, 6-hydroxy-3-hexynyl nonyloxymethyl ether, 6-hydroxy-3-hexynyl decyloxymethyl ether, and 6-hydroxy-3-hexynyl benzyloxymethyl ether.

Examples of the reduction to synthesize the 6-hydroxy-3-hexenyl alkoxymethyl ether compound (9) include (i) a catalytic hydrogenation, (ii) a reduction using a zinc compound in an alcohol solvent, (iii) a hydroboration with a dialkylborane, followed by protonation, (iv) a reduction using potassium hydroxide and N,N-dimethylformamide (DMF) in the presence of a palladium catalyst such as palladium acetate, (v) a hydrosilylation to obtain vinylsilane, followed by desilylation, (vi) hydroalumination, and (vii) a Birch reduction. Preferred are the catalytic hydrogenation (i), the reduction using a zinc compound (ii), the hydroboration, followed by protonation (iii), and the hydroalumination (vi) in view of the selectivity and productivity. The catalytic hydrogenation (i) is preferred, when it is desired to obtain a carbon-carbon double bond in a Z-selective manner in the 6-hydroxy-3-hexenyl alkoxymethyl ether compound (9). The hydroalumination (vi) is preferred, when it is desired to obtain a carbon-carbon double bond in an E-selective manner in the 6-hydroxy-3-hexenyl alkoxymethyl ether compound (9).

(i) Catalytic Hydrogenation

The catalytic hydrogenation is carried out by supplying a hydrogen gas in the presence of a metal catalyst.

Examples of the metal catalyst used in the catalytic hydrogenation include Lindlar catalyst; nickel catalysts such as P-2 nickel boride catalyst (Thomas J. Caggiano et al. Encyclopedia of Reagents for Organic Synthesis: 3694-3699) (hereinafter also referred to as "P-2 Ni catalyst"); and palladium catalysts such as palladium carbon and Pd-PEI that is palladium carbon poisoned by polyethylenimine polymer (PEI). Lindlar catalyst and nickel catalysts are preferred in view of the economy.

An amount of the metal catalyst varies, depending on a catalyst to be used. When the catalyst is solid, like a Lindlar catalyst, the amount is preferably 0.01 to 50 g per mol of the 6-hydroxy-3-hexynyl alkoxymethyl ether compound (8) in view of the reactivity. The P-2 Ni catalyst is preferably used in an amount of 0.001 to 0.50 mol, as reduced to a nickel compound, per mol of the 6-hydroxy-3-hexynyl alkoxymethyl ether compound (8).

The solid catalyst may be dispersed in a solvent.

When the metal catalyst is too highly active, a catalyst poison may be incorporated, if necessary.

Examples of the catalyst poison include amine compounds such as pyridine, quinoline, and ethylenediamine; phosphorus compounds such as triphenylphosphine, tritolylphosphine, and triethylphosphite; and sulfur compounds such as benzenethiol, diphenyl sulfide, dimethyl sulfide, and dimethyl sulfoxide.

An amount of the catalyst poison varies greatly, depending on a catalyst poison to be used, and is preferably 0.0001 to 10.0 g per mol of the 6-hydroxy-3-hexynyl alkoxymethyl ether compound (8) in view of the reaction rate and geometrical selectivity.

Examples of the solvent used in the catalytic hydrogenation include hydrocarbons such as hexane, heptane, benzene, toluene, xylene, and cumene; nitriles such as acetonitrile and propionitrile; esters such as methyl acetate, ethyl acetate, n-propyl acetate, and n-butyl acetate; and alcohols such as methanol, ethanol, propanol, butanol, pentanol, hexanol, 2-propanol, 2-butanol, and cyclohexanol.

The solvent may be used alone or in combination thereof, if necessary. The solvent may be commercially available one.

When a Lindlar catalyst is used, the solvent is preferably a hydrocarbon such as hexane, heptane, toluene or xylene in view of the reactivity. When a nickel catalyst is used, the solvent is preferably an alcohol such as methanol, ethanol, propanol, butanol, or 2-propanol in view of the reactivity. When a palladium catalyst such as palladium carbon is used, the solvent is preferably an ester such as methyl acetate or ethyl acetate in view of the reactivity.

An amount of the solvent varies, depending on a catalyst and/or a solvent to be used, and is preferably 0 to 1,000 g per mol of the 6-hydroxy-3-hexynyl alkoxymethyl ether compound (8) in view of the reactivity.

A reaction temperature in the catalytic hydrogenation varies, depending on a catalyst and/or solvent used, and is preferably 0 to 160° C., more preferably 20 to 100° C., in view of the geometrical selectivity.

A reaction time in the catalytic hydrogenation is preferably 1 to 100 hours in view of the yield.

(ii) Reduction Using a Zinc Compound in an Alcohol Solvent

The reduction is carried out using a zinc compound in an alcohol solvent.

An alcohol used as the solvent has preferably 1 to 10, more preferably 1 to 5, carbon atoms. Examples of the alcohol used as the solvent include linear alcohol compounds such as methanol, ethanol, propanol, butanol, pentanol, hexanol, heptanol, octanol, nonanol, and decanol; branched alcohol compounds such as 2-propanol and 2-butanol; and cyclic alcohol compounds such as cyclohexanol. Alcohol compounds having 1 to 5 carbon atoms, such as methanol, ethanol, propanol, butanol, pentanol, and 2-propanol, are preferred in view of the reactivity.

An amount of the alcohol is preferably 46 to 1,000 g per mol of the 6-hydroxy-3-hexynyl alkoxymethyl ether compound (8) in view of the reactivity.

The zinc compound refers to metallic zinc or activated zinc as explained below.

An amount of the zinc compound is preferably 1.0 to 1,000 mol, more preferably 1.0 to 200 mol, per mol of the 6-hydroxy-3-hexynyl alkoxymethyl ether compound (8) in view of the reactivity.

The reduction may take a longer time due to the low reactivity of zinc. Then, an activator which activates zinc may be added or a zinc compound which has been activated in advance may be used.

Examples of the activator include 1,2-dibromoethane, cuprous chloride, cuprous bromide, cuprous iodide, lithium bromide, iodine, and chlorotrimethylsilane.

The activator may be used alone or in combination thereof, if necessary.

An amount of the activator is preferably 0.01 to 10.0 mol per mol of the 6-hydroxy-3-hexynyl alkoxymethyl ether compound (8) in view of the reactivity.

The activated zinc maybe prepared, for example, by treating metallic zinc with an acid such as hydrochloric acid; reducing zinc chloride with metallic lithium in tetrahydrofuran; or reacting metallic zinc with 1,2-dibromoethane and lithium dibromocuprate in tetrahydrofuran.

A reaction temperature in the reduction varies, depending on a solvent to be used, and is preferably 20 to 120° C. in view of the reactivity.

A reaction time in the reduction is preferably 1 to 150 hours in view of the completion of the reaction.

(iii) Hydroboration with a Dialkylborane, Followed by Protonation

For the reduction, hydroboration with a dialkylborane is first carried out in a solvent.

The dialkylborane used in the hydroboration has preferably 4 to 18, more preferably 6 to 12, carbon atoms.

Examples of the dialkylborane include dicyclohexylborane, diisoamylborane, disiamylborane, 9-borabicyclo[3.3.1]nonane (9-BBN), diisopinocampheylborane, catecholborane, and pinacolborane. Dicyclohexylborane and diisoamylborane are preferred in view of the reactivity.

An amount of the dialkylborane is preferably 1.0 to 4.0 mol per mol of the 6-hydroxy-3-hexynyl alkoxymethyl ether compound (8) in view of the reactivity.

Examples of the solvent used in the hydroboration include ethers such as tetrahydrofuran, diethyl ether, dibutyl ether, 4-methyltetrahydropyran, cyclopentylmethylether, 1,4-dioxane, and diethyleneglycol dimethyl ether; and hydrocarbons such as hexane, heptane, benzene, toluene, xylene, and cumene. Ethers such as tetrahydrofuran, 4-methyltetrahydropyran, and diethyleneglycol dimethyl ether are more preferred in view of the reactivity.

The solvent may be used alone or in combination thereof, if necessary. The solvent may be commercially available one.

An amount of the solvent is preferably 100 to 3,000 g per mol of the 6-hydroxy-3-hexynyl alkoxymethyl ether compound (8) in view of the reactivity.

A reaction temperature in the hydroboration is preferably −20 to 50° C. in view of the geometrical selectivity.

A reaction time in the hydroboration varies, depending on a reaction temperature and/or a reaction scale, and is preferably 1 to 100 hours in view of the reactivity.

For the reduction, protonation is carried out with an acid in a solvent after the hydroboration.

Examples of the acid used in the protonation include carboxylic acids such as acetic acid, propionic acid, butyric acid, pentanoic acid, pivalic acid, heptanoic acid, trifluoroacetic acid, chloroacetic acid, formic acid, and oxalic acid; sulfonic acids such as p-toluenesulfonic acid; and mineral acids such as sulfuric acid, hydrochloric acid, nitric acid, and phosphoric acid. Carboxylic acids such as acetic acid and propionic acid are preferred in view of the reactivity.

An amount of the acid is preferably 2.0 to 20.0 mol per mol of the 6-hydroxy-3-hexynyl alkoxymethyl ether compound (8) in view of the reactivity.

The species and the amount of the solvent may be the same as those in the hydroboration, because the protonation is carried out subsequently in the hydroboration reaction mixture.

A reaction temperature in the protonation varies, depending on a reagent to be used, and is preferably 0 to 150° C. in view of the reaction rate.

A reaction time in the protonation varies, depending on a reaction temperature and/or a reaction scale, and is preferably 1 to 70 hours in view of the reactivity.

(iv) Reduction Using Potassium Hydroxide and N,N-dimethylformamide (DMF) in the Presence of a Palladium Catalyst Such as Palladium Acetate The reduction is carried out using potassium hydroxide and N,N-dimethylformamide (DMF) in the presence of a palladium catalyst such as palladium acetate, preferably at 100 to 180° C. for 6 to 100 hours.

(v) Hydrosilylation to Obtain Vinylsilane, Followed by Desilylation

The hydrosilylation is carried out with a trialkylsilane and a metal catalyst, such as a Wilkinson catalyst or a Trost catalyst.

An amount of the metal catalyst is preferably 0.0001 to 4.0 mol, more preferably 0.001 to 1.0 mol, per mol of the 6-hydroxy-3-hexynyl alkoxymethyl ether compound (8) in view of the reactivity.

The hydrosilylation is preferably carried out at 5 to 100° C. for 1 to 100 hours.

The desilylation after the hydrosilylation is preferably carried out using, for example, at least one out of acids such as sulfuric acid or hydrochloric acid, hydrogen iodide, acetyl chloride, titanium tetrachloride, and iodine at 5 to 80° C. for 1 to 100 hours.

(vi) Hydroalumination

The hydroalumination is carried out using lithium aluminum hydride.

An amount of lithium aluminum hydride is preferably 0.25 to 4.0 mol, more preferably 0.35 to 2.0 mol, per mol of the 6-hydroxy-3-hexynyl alkoxymethyl ether compound (8) in view of the reactivity.

Examples of a solvent used in the hydroalumination include ethers such as diethyl ether, dibutyl ether, 4-methyltetrahydropyran, tetrahydrofuran (THF), cyclopentylmethylether, 1,4-dioxane, and diethyleneglycol dimethyl ether; and hydrocarbons such as hexane, heptane, benzene, toluene, xylene, and cumene. Ethers such as tetrahydrofuran, 4-methyltetrahydropyran, and diethyleneglycol dimethyl ether are preferred in view of the reactivity.

The solvent may be used alone or in combination thereof, if necessary. The solvent may be commercially available one.

The hydroalumination is preferably carried out at 20 to 180° C. for 1 to 100 hours.

(vii) Birch Reduction

The Birch reduction is carried out using a metal in an amine or alcohol.

Examples of the metal include alkaline metals such as potassium, sodium, and lithium; and alkaline earth metals such as calcium and magnesium.

Examples of the amine include ammonia; and lower amines such as methylamine, ethylamine, and propylamine.

Examples of the alcohol include methanol, ethanol, and 2-methylpropanol.

The Birch reduction is preferably carried out at −78 to 20° C. for 1 to 100 hours.

The geometry of the carbon-carbon double bond of the 6-hydroxy-3-hexenyl alkoxymethyl ether compound (9) may be controlled selectively in an E- or Z-configuration by choosing reduction conditions.

The 6-hydroxy-3-hexenyl alkoxymethyl ether compound (9) indicated in the aforesaid reaction scheme for preparing the compound (1) from the compound (7) will be explained below.

$R^1$ in the general formula (9) is as defined for the general formula (1).

Specific examples of the 6-hydroxy-3-hexenyl alkoxymethyl ether compound (9) include 6-hydroxy-3-hexenyl methoxymethyl ether, 6-hydroxy-3-hexenyl ethoxymethyl ether, 6-hydroxy-3-hexenyl propoxymethyl ether, 6-hydroxy-3-hexenyl butoxymethyl ether, 6-hydroxy-3-hexenyl pentyloxymethyl ether, 6-hydroxy-3-hexenyl hexyloxymethyl ether, 6-hydroxy-3-hexenyl heptyloxymethyl ether, 6-hydroxy-3-hexenyl octyloxymethyl ether, 6-hydroxy-3-hexenyl nonyloxymethyl ether, 6-hydroxy-3-hexenyl decyloxymethyl ether, and 6-hydroxy-3-hexenyl benzyloxymethyl ether.

The halogenation reaction for synthesizing the 6-halo-3-hexenyl alkoxymethyl ether compound (10-a) may be carried out, for example, by tosylating the hydroxyl group with a p-toluenesulfonyl halide compound, followed by halogenation with a lithium halide compound, or by directly halogenating the hydroxyl group with a halogenating agent.

Examples of the halogenating agent include halogen molecules such as chlorine, bromine, and iodine; hydrogen halide compounds such as hydrogen chloride, hydrogen bromide, and hydrogen iodide; methanesulfonyl halide compounds such as methanesulfonyl chloride, methanesulfonyl bromide, and methanesulfonyl iodide; benzenesulfonyl halide compounds such as benzenesulfonyl chloride, benzenesulfonyl bromide, and benzenesulfonyl iodide; p-toluenesulfonyl halide compounds such as p-toluenesulfonyl chloride, p-toluenesulfonyl bromide, and p-toluenesulfonyl iodide; phosphorus halide compounds such as phosphorous trichloride, phosphorous pentachloride, and phosphorus tribromide; carbon tetrahalide compounds such as carbon tetrachloride, carbon tetrabromide, and carbon tetraiodide; alkylsilyl halide compounds such as tetramethylsilyl chloride, tetramethylsilyl bromide, tetramethylsilyl iodide, triethylsilyl chloride, triethylsilyl bromide, triethylsilyl iodide, triisopropylsilyl chloride, triisopropylsilyl bromide, triisopropylsilyl iodide, tert-butyldimethylsilyl chloride, tert-butyldimethylsilyl bromide, and tert-butyldimethylsilyl iodide; oxalyl halide compounds such as oxalyl chloride, oxalyl bromide, and oxalyl iodide; and N-halosuccinimide compounds such as N-chlorosuccinimide, N-bromosuccinimide, and N-iodosuccinimide. A methanesulfonyl halide compound, a benzenesulfonyl halide compound, and a p-toluenesulfonyl halide compound, particularly a methanesulfonyl halide compound, are preferred in view of the suppression of side reactions.

The halogenating agent may be used alone or in combination thereof, if necessary. The halogenating agent may be commercially available one.

An amount of the halogenating agent used is preferably 0.8 to 5.0 mol, more preferably 1.0 to 2.5 mol, per mol of the 6-hydroxy-3-hexenyl alkoxymethyl ether compound (9).

A base may be incorporated in the halogenation reaction, if necessary.

Examples of the base include hydroxides such as sodium hydroxide, potassium hydroxide, calcium hydroxide, and magnesium hydroxide; carbonates such as sodium carbonate, potassium carbonate, calcium carbonate, and magnesium carbonate; amines such as triethylamine, N,N-diisopropylethylamine, piperidine, pyrrolidine, pyridine, lutidine, 4-dimethylaminopyridine, N,N-dimethylaniline, N,N-diethylaniline, and 1,8-diazabicyclo[5.4.0]-7-undecene (DBU); and phosphines such as tributylphosphine, triphenylphosphine, and tritolylphosphine.

When the halogenating agent is a methanesulfonyl halide compound, a benzenesulfonyl halide compound, or a p-toluenesulfonyl halide compound, the base is preferably an amine, more preferably pyridines such as pyridine, lutidine, or 4-dimethylaminopyridine.

The base may be used alone or in combination thereof, if necessary. The base may be commercially available one.

An amount of the base is preferably 0 to 8.0 mol, more preferably 0 to 3.0 mol, per mol of the 6-hydroxy-3-hexenyl alkoxymethyl ether compound (9) in view of the yield and/or economy.

A metal salt may be incorporated in the halogenation reaction, if necessary.

Examples of the metal salt include lithium salts such as lithium chloride, lithium bromide, and lithium iodide; sodium salts such as sodium chloride, sodium bromide, and sodium iodide; potassium salts such as potassium chloride, potassium bromide, and potassium iodide; calcium salts such as calcium chloride, calcium bromide, and calcium iodide; and magnesium salts such as magnesium chloride, magnesium bromide, and magnesium iodide.

The metal salt may be used alone or in combination thereof, if necessary. The metal salt may be commercially available one.

An amount of the metal salt is preferably 0 to 30.0 mol, more preferably 0 to 5.0 mol, per mol of the 6-hydroxy-3-hexenyl alkoxymethyl ether compound (9) in view of the reactivity.

Although the metal salt increases a concentration of halide ions in the reaction system to thereby enhance the reactivity, it is preferred in view of the economy and/or environmental protection not to incorporate the metal salt.

A solvent may be incorporated in the halogenation reaction, if necessary.

Examples of the solvent include usual solvents, for example, ethers such as diethyl ether, dibutyl ether, 4-methyltetrahydropyran, tetrahydrofuran (THF), cyclopentylmethylether, and 1,4-dioxane; hydrocarbons such as hexane, heptane, benzene, toluene, xylene, and cumene; chlorinated solvents such as trichloroethylene, dichloromethane, and chloroform; aprotic polar solvents such as dimethyl sulfoxide, γ-butyrolactone (GBL), N-methylpyrrolidone (NMP), N,N-dimethylformamide (DMF), N,N-dimethylacetamide (DMAC), and hexamethylphosphoric triamide (HMPA); nitriles such as acetonitrile and propionitrile; and esters such as methyl acetate, ethyl acetate, n-propyl acetate, and n-butyl acetate. 4-Methyltetrahydropyran, dichloromethane, chloroform, γ-butyrolactone, N-methylpyrrolidone, N,N-dimethylformamide, N,N-dimethylacetamide, and acetonitrile are preferred in view of the reactivity. γ-Butyrolactone and acetonitrile are particularly preferred in view of the safety.

The solvent may be used alone or in combination thereof, if necessary. The solvent may be commercially available one.

An amount of the solvent used in the halogenation reaction is preferably 0 to 3,000 g, more preferably 0 to 800 g, per mol of the 6-hydroxy-3-hexenyl alkoxymethyl ether compound (9).

The solvent may occupy a part of a reactor space to reduce a space for the starting materials, resulting in a decreased productivity. Therefore, the reaction may be carried out without a solvent or with the base as the solvent.

A reaction temperature in the halogenation varies, depending on a halogenating agent to be used, and is preferably 5 to 180° C. in view of the reactivity.

A reaction time in the halogenation reaction varies, depending on a halogenating agent and/or a reaction scale, and is preferably 0.5 to 100 hours in view of the reactivity.

The 6-halo-3-hexenyl alkoxymethyl ether compound (10-a) indicated in the aforesaid reaction scheme for preparing the compound (1) from the compound (7) will be explained below.

$R^1$ in the general formula (10-a) is as defined for the general formula (1).

Specific examples of the 6-halo-3-hexenyl alkoxymethyl ether compound (10-a) include 6-halo-3-hexenyl methoxymethyl ether, 6-halo-3-hexenyl ethoxymethyl ether, 6-halo-3-hexenyl propoxymethyl ether, 6-halo-3-hexenyl butoxymethyl ether, 6-halo-3-hexenyl pentyloxymethyl ether, 6-halo-3-hexenyl hexyloxymethyl ether, 6-halo-3-hexenyl heptyloxymethyl ether, 6-halo-3-hexenyl octyloxymethyl ether, 6-halo-3-hexenyl nonyloxymethyl ether, 6-halo-3-hexenyl decyloxymethyl ether, and 6-halo-3-hexenyl benzyloxymethyl ether.

The 6-halo-3-hexenyl alkoxymethyl ether compound (10-a) is reacted with, for example, magnesium or an organolithium reagent in a solvent to obtain the nucleophilic reagent, 6-(alkoxymethoxy)-3-hexenyl compound (11-a), which is then subjected to a coupling reaction with the dihaloalkane compound (12), whereby the number of carbon atoms of the haloalkenyl alkoxymethyl ether compound (10) may be increased. The increase in the number of carbon atoms through the coupling reaction is carried out when "a" in the general formula (1), which represents the target compound, dialkoxyalkenyl alkoxymethyl ether compound (1), is an integer of 5 to 15.

That is, one example of the process for synthesizing the nucleophilic reagent, 6-(alkoxymethoxy)-3-hexenyl compound (11-a), comprises reacting the 6-halo-3-hexenyl alkoxymethyl ether compound (10-a) with magnesium in a solvent to obtain a 6-(alkoxymethoxy)-3-hexenyl nucleophilic reagent (11-a: $M^1$=MgZ$^1$) which is a Grignard reagent, as shown in the following chemical reaction formula. This process is hereinafter referred to as "conversion with magnesium".

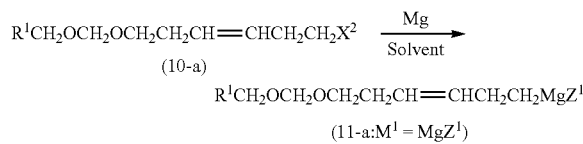

An amount of magnesium used in the conversion with magnesium is preferably 1.0 to 2.0 s per mol of the 6-halo-3-hexenyl alkoxymethyl ether compound (10-a) in view of the completion of the reaction.

Examples of the solvent used in the conversion with magnesium include ethers such as tetrahydrofuran, diethyl ether, and 4-methyltetrahydropyran; and hydrocarbons such as toluene, xylene, and hexane. Ethers such as tetrahydrofuran, diethyl ether, and 4-methyltetrahydropyran, particularly tetrahydrofuran, are preferred in view of a reaction rate of the Grignard reagent formation.

The solvent may be used alone or in combination thereof, if necessary. The solvent may be commercially available one.

An amount of the solvent used is preferably 50 to 5,000 g, more preferably 100 g to 3,000 g, per mol of the 6-halo-3-hexenyl alkoxymethyl ether compound (10-a) in view of the reactivity.

A reaction temperature in the conversion with magnesium varies, depending on a solvent to be used, and is preferably 0 to 120° C. in view of the reactivity.

A reaction time in the conversion with magnesium varies, depending on a solvent and/or a reaction scale to be used, and is preferably 0.5 to 100 hours in view of the reactivity.

Another example of the process for synthesizing the nucleophilic reagent, 6-(alkoxymethoxy)-3-hexenyl compound (11-a), comprises reacting the 6-halo-3-hexenyl alkoxymethyl ether compound (10-a) with an organolithium reagent in a solvent to obtain a 6-(alkoxymethoxy)-3-hexenyl lithium compound (11-a: $M^1$=Li), as shown in the following chemical reaction formula. This process is hereinafter referred to as "conversion with an organolithium reagent".

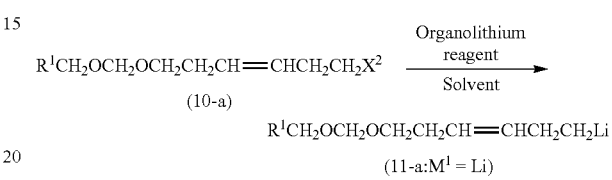

Examples of the organolithium reagent include linear organolithium reagents such as methyllithium, ethyllithium, n-propyllithium, n-butyllithium, and n-pentyllithium; and branched organolithium reagents such as sec-butyllithium and tert-butyllithium. Methyllithium, n-butyllithium, sec-butyllithium, and tert-butyllithium are preferred in view of the availability.

An amount of the organolithium reagent used is preferably 1.0 to 4.0 mol, more preferably 1.0 to 2.0 mol, per mol of the 6-halo-3-hexenyl alkoxymethyl ether compound (10-a) in view of the reactivity.

Examples of the solvent used in the conversion with an organolithium reagent include ethers such as tetrahydrofuran, diethyl ether, and 4-methyltetrahydropyran; and hydrocarbons such as toluene, xylene, and hexane. A preferable solvent varies, depending on an organolithium reagent to be used. Generally, tetrahydrofuran, diethyl ether, toluene, and hexane are preferred in view of the reactivity.

The solvent may be used alone or in combination thereof, if necessary. The solvent may be commercially available one.

An amount of the solvent used is preferably 50 to 5,000 g, more preferably 100 to 3,000 g, per mol of the 6-halo-3-hexenyl alkoxymethyl ether compound (10-a) in view of the reactivity.

A reaction temperature in the conversion with an organolithium reagent varies, depending on a solvent to be used, and is preferably −78 to 25° C. in view of the reactivity.

A reaction time in the conversion with an organolithium reagent varies, depending on a solvent and/or a reaction scale to be used, and is preferably 0.5 to 100 hours in view of the reactivity.

The nucleophilic reagent, 6-(alkoxymethoxy)-3-hexenyl compound (11-a), indicated in the aforesaid reaction scheme for preparing the compound (1) from the compound (7) will be explained below.

$R^1$ in the general formula (11-a) is as defined for the general formula (1).

$M^1$ represents Li or MZ$^1$, wherein Z$^1$ represents a halogen atom or a 6-(alkoxymethoxy)-3-hexenyl group. Examples of the halogen atom, Z$^1$, include a chlorine atom, a bromine atom, and an iodine atom.

Examples of the nucleophilic reagent, 6-(alkoxymethoxy)-3-hexenyl compound (11-a), include (3E)-6-(alkoxymethoxy)-3-hexenyl compound of the following general formula (11-a-E), (3Z)-6-(alkoxymethoxy)-3-hexenyl compound of the following general formula (11-a-Z), and a mixture thereof.

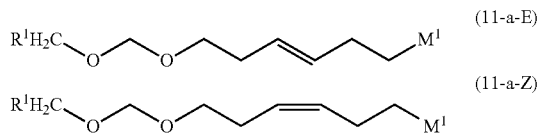

Specific examples of the nucleophilic reagent, (3E)-6-(alkoxymethoxy)-3-hexenyl compound (11-a-E), include the following compounds:

(3E)-6-(alkoxymethoxy)-3-hexenyllithium compounds such as (3E)-6-(methoxymethoxy)-3-hexenyllithium, (3E)-6-(ethoxymethoxy)-3-hexenyllithium, (3E)-6-(propoxymethoxy)-3-hexenyllithium, (3E)-6-(butoxymethoxy)-3-hexenyllithium, (3E)-6-(pentyloxymethoxy)-3-hexenyllithium, (3E)-6-(hexyloxymethoxy)-3-hexenyllithium, (3E)-6-(heptyloxymethoxy)-3-hexenyllithium, (3E)-6-(octyloxymethoxy)-3-hexenyllithium, (3E)-6-(nonyloxymethoxy)-3-hexenyllithium, and (3E)-6-(decyloxymethoxy)-3-hexenyllithium;

(3E)-6-(alkoxymethoxy)-3-hexenylmagnesium chloride compounds such as (3E)-6-(methoxymethoxy)-3-hexenylmagnesium chloride, (3E)-6-(ethoxymethoxy)-3-hexenylmagnesium chloride, (3E)-6-(propoxymethoxy)-3-hexenylmagnesium chloride, (3E)-6-(butoxymethoxy)-3-hexenylmagnesium chloride, (3E)-6-(pentyloxymethoxy)-3-hexenylmagnesium chloride, (3E)-6-(hexyloxymethoxy)-3-hexenylmagnesium chloride, (3E)-6-(heptyloxymethoxy)-3-hexenylmagnesium chloride, (3E)-6-(octyloxymethoxy)-3-hexenylmagnesium chloride, (3E)-6-(nonyloxymethoxy)-3-hexenylmagnesium chloride, and (3E)-6-(decyloxymethoxy)-3-hexenylmagnesium chloride;

(3E)-6-(alkoxymethoxy)-3-hexenylmagnesium bromide compounds such as (3E)-6-(methoxymethoxy)-3-hexenylmagnesium bromide, (3E)-6-(ethoxymethoxy)-3-hexenylmagnesium bromide, (3E)-6-(propoxymethoxy)-3-hexenylmagnesium bromide, (3E)-6-(butoxymethoxy)-3-hexenylmagnesium bromide, (3E)-6-(pentyloxymethoxy)-3-hexenylmagnesium bromide, (3E)-6-(hexyloxymethoxy)-3-hexenylmagnesium bromide, (3E)-6-(heptyloxymethoxy)-3-hexenylmagnesium bromide, (3E)-6-(octyloxymethoxy)-3-hexenylmagnesium bromide, (3E)-6-(nonyloxymethoxy)-3-hexenylmagnesium bromide, and (3E)-6-(decyloxymethoxy)-3-hexenylmagnesium bromide; and (3E)-6-(alkoxymethoxy)-3-hexenylmagnesium iodide compounds such as (3E)-6-(methoxymethoxy)-3-hexenylmagnesium iodide, (3E)-6-(ethoxymethoxy)-3-hexenylmagnesium iodide, (3E)-6-(propoxymethoxy)-3-hexenylmagnesium iodide, (3E)-6-(butoxymethoxy)-3-hexenylmagnesium iodide, (3E)-6-(pentyloxymethoxy)-3-hexenylmagnesium iodide, (3E)-6-(hexyloxymethoxy)-3-hexenylmagnesium iodide, (3E)-6-(heptyloxymethoxy)-3-hexenylmagnesium iodide, (3E)-6-(octyloxymethoxy)-3-hexenylmagnesium iodide, (3E)-6-(nonyloxymethoxy)-3-hexenylmagnesium iodide, and (3E)-6-(decyloxymethoxy)-3-hexenylmagnesium iodide.

Among these, (3E)-6-(alkoxymethoxy)-3-hexenylmagnesium halide compounds such as (3E)-6-(alkoxymethoxy)-3-hexenylmagnesium chloride compounds are preferred in view of the availability.

Specific examples of the nucleophilic reagent, (3Z)-6-(alkoxymethoxy)-3-hexenyl compound (11-a-Z), include the following compounds:

(3Z)-6-(alkoxymethoxy)-3-hexenyllithium compounds such as (3Z)-6-(methoxymethoxy)-3-hexenyllithium, (3Z)-6-(ethoxymethoxy)-3-hexenyllithium, (3Z)-6-(propoxymethoxy)-3-hexenyllithium, (3Z)-6-(butoxymethoxy)-3-hexenyllithium, (3Z)-6-(pentyloxymethoxy)-3-hexenyllithium, (3Z)-6-(hexyloxymethoxy)-3-hexenyllithium, (3Z)-6-(heptyloxymethoxy)-3-hexenyllithium, (3Z)-6-(octyloxymethoxy)-3-hexenyllithium, (3Z)-6-(nonyloxymethoxy)-3-hexenyllithium, and (3Z)-6-(decyloxymethoxy)-3-hexenyllithium;

(3Z)-6-(alkoxymethoxy)-3-hexenylmagnesium chloride compounds such as (3Z)-6-(methoxymethoxy)-3-hexenylmagnesium chloride, (3Z)-6-(ethoxymethoxy)-3-hexenylmagnesium chloride, (3Z)-6-(propoxymethoxy)-3-hexenylmagnesium chloride, (3Z)-6-(butoxymethoxy)-3-hexenylmagnesium chloride, (3Z)-6-(pentyloxymethoxy)-3-hexenylmagnesium chloride, (3Z)-6-(hexyloxymethoxy)-3-hexenylmagnesium chloride, (3Z)-6-(heptyloxymethoxy)-3-hexenylmagnesium chloride, (3Z)-6-(octyloxymethoxy)-3-hexenylmagnesium chloride, (3Z)-6-(nonyloxymethoxy)-3-hexenylmagnesium chloride, and (3Z)-6-(decyloxymethoxy)-3-hexenylmagnesium chloride;

(3Z)-6-(alkoxymethoxy)-3-hexenylmagnesium bromide compounds such as (3Z)-6-(methoxymethoxy)-3-hexenylmagnesium bromide, (3Z)-6-(ethoxymethoxy)-3-hexenylmagnesium bromide, (3Z)-6-(propoxymethoxy)-3-hexenylmagnesium bromide, (3Z)-6-(butoxymethoxy)-3-hexenylmagnesium bromide, (3Z)-6-(pentyloxymethoxy)-3-hexenylmagnesium bromide, (3Z)-6-(hexyloxymethoxy)-3-hexenylmagnesium bromide, (3Z)-6-(heptyloxymethoxy)-3-hexenylmagnesium bromide, (3Z)-6-(octyloxymethoxy)-3-hexenylmagnesium bromide, (3Z)-6-(nonyloxymethoxy)-3-hexenylmagnesium bromide, and (3Z)-6-(decyloxymethoxy)-3-hexenylmagnesium bromide; and (3Z)-6-(alkoxymethoxy)-3-hexenylmagnesium iodide compounds such as (3Z)-6-(methoxymethoxy)-3-hexenylmagnesium iodide, (3Z)-6-(ethoxymethoxy)-3-hexenylmagnesium iodide, (3Z)-6-(propoxymethoxy)-3-hexenylmagnesium iodide, (3Z)-6-(butoxymethoxy)-3-hexenylmagnesium iodide, (3Z)-6-(pentyloxymethoxy)-3-hexenylmagnesium iodide, (3Z)-6-(hexyloxymethoxy)-3-hexenylmagnesium iodide, (3Z)-6-(heptyloxymethoxy)-3-hexenylmagnesium iodide, (3Z)-6-(octyloxymethoxy)-3-hexenylmagnesium iodide, (3Z)-6-(nonyloxymethoxy)-3-hexenylmagnesium iodide, and (3Z)-6-(decyloxymethoxy)-3-hexenylmagnesium iodide.

Among these, (3Z)-6-(alkoxymethoxy)-3-hexenylmagnesium halide compounds such as (3Z)-6-(alkoxymethoxy)-3-hexenylmagnesium chloride compounds are preferred in view of the availability.

The nucleophilic reagent, 6-(alkoxymethoxy)-3-hexenyl compound (11-a), may be used alone or in combination thereof, if necessary.

The nucleophilic reagent, 6-(alkoxymethoxy)-3-hexenyl compound (11-a), may be commercially available one or may be prepared in house.

The dihaloalkane compound (12) indicated in the aforesaid reaction scheme for preparing the compound (1) from the compound (7) will be explained below.

$X^3$ and $X^4$ in the general formula (12) represent, independently of each other, a halogen atom such as a fluorine atom, a chlorine atom, a bromine atom, or an iodine atom.

"b" in the general formula (12) represents an integer of 3 to 13, preferably 3 to 9.

The haloalkenyl alkoxymethyl ether compound (10) having a desired number of carbon atoms may be-prepared by choosing the number of carbon number, i.e., "b", of the dihaloalkane compound (12).

An amount of the dihaloalkane compound (12) is preferably 0.7 to 5.0 mol, more preferably 0.7 to 2.5 mol, per mol of the 6-halo-3-hexenyl alkoxymethyl ether compound (10-a) in view of the reactivity.

Specific examples of the dihaloalkane compound (12) include the following compounds:

1,3-dihalopropane compounds (b=3) such as 1,3-dichloropropane, 1,3-dibromopropane, 1,3-diiodopropane, 1-bromo-3-chloropropane, 1-chloro-3-iodopropane, and 1-bromo-3-iodopropane;

1,4-dihalobutane compounds (b=4) such as 1,4-dichlorobutane, 1,4-dibromobutane, 1,4-diiodobutane, 1-bromo-4-chlorobutane, 1-chloro-4-iodobutane, and 1-bromo-4-iodobutane;

1,5-dihalopentane compounds (b=5) such as 1,5-dichloropentane, 1,5-dibromopentane, 1,5-diiodopentane, 1-bromo-5-chloropentane, 1-chloro-5-iodopentane, and 1-bromo-5-iodopentane;

1,6-dihalohexane compounds (b=6) such as 1,6-dichlorohexane, 1,6-dibromohexane, 1,6-diiodohexane, 1-bromo-6-chlorohexane, 1-chloro-6-iodohexane, and 1-bromo-6-iodohexane;

1,7-dihaloheptane compounds (b=7) such as 1,7-dichloroheptane, 1,7-dibromoheptane, 1,7-diiodoheptane, 1-bromo-7-chloroheptane, 1-chloro-7-iodoheptane, and 1-bromo-7-iodoheptane;

1,8-dihalooctane compounds (b=8) such as 1,8-dichlorooctane, 1,8-dibromooctane, 1,8-diiodooctane, 1-bromo-8-chlorooctane, 1-chloro-8-iodooctane, and 1-bromo-8-iodooctane;

1,9-dihalononane compounds (b=9) such as 1,9-dichlorononane, 1,9-dibromononane, 1,9-diiodononane, 1-bromo-9-chlorononane, 1-chloro-9-iodononane, and 1-bromo-9-iodononane;

1,10-dihalodecane compounds (b=10) such as 1,10-dichlorodecane, 1,10-dibromodecane, 1,10-diiododecane, 1-bromo-10-chlorodecane, 1-chloro-10-iododecane, and 1-bromo-10-iododecane;

1,11-dihaloundecane compounds (b=11) such as 1,11-dichloroundecane, 1,11-dibromoundecane, 1,11-diiodoundecane, 1-bromo-11-chloroundecane, 1-chloro-11-iodoundecane, and 1-bromo-11-iodoundecane;

1,12-dihalododecane compounds (b=12) such as 1,12-dichlorododecane, 1,12-dibromododecane, 1,12-diiodododecane, 1-bromo-12-chlorododecane, 1-chloro-12-iodododecane, and 1-bromo-12-iodododecane; and 1,13-dihalotridecane compounds (b=13) such as 1,13-dichlorotridecane, 1,13-dibromotridecane, 1,13-diiodotridecane, 1-bromo-13-chlorotridecane, 1-chloro-13-iodotridecane, and 1-bromo-13-iodotridecane.

The dihaloalkane compound (12) maybe used alone or in combination thereof, if necessary. The dihaloalkane compound (12) may be commercially available one or may be prepared in house.

A solvent may be incorporated in the coupling reaction, if necessary. Examples of the solvent include usual solvents, for example, ethers such as diethyl ether, dibutyl ether, 4-methyltetrahydropyran, tetrahydrofuran (THF), cyclopentylmethylether, and 1,4-dioxane; hydrocarbons such as hexane, heptane, benzene, toluene, xylene, and cumene; chlorinated solvents such as trichloroethylene, dichloromethane, and chloroform; aprotic polar solvents such as dimethyl sulfoxide, γ-butyrolactone (GBL), N-methylpyrrolidone (NMP), N,N-dimethylformamide (DMF), N,N-dimethylacetamide (DMAC), and hexamethylphosphoric triamide (HMPA); and nitriles such as acetonitrile and propionitrile. Toluene, tetrahydrofuran, 4-methyltetrahydropyran, and acetonitrile, particularly tetrahydrofuran, are preferred in view of the reactivity.

The solvent may be used alone or in combination thereof, if necessary. The solvent may be commercially available one.

An amount of the solvent used is preferably 30 to 5,000 g, more preferably 50 to 3,000 g, per mol of the 6-halo-3-hexenyl alkoxymethyl ether compound (10-a) in view of the reactivity.

A catalyst may be incorporated in the coupling reaction, if necessary. Examples of the catalyst include copper compounds including cuprous halides such as cuprous chloride, cuprous bromide, and cuprous iodide, and cupric halides such as cupric chloride, cupric bromide, and cupric iodide; iron compounds such as iron(II) chloride, iron(III) chloride, iron(II) bromide, iron(III) bromide, iron(II) iodide, iron(III) iodide, and iron(III) acetylacetonate; silver compounds such as silver chloride, silver nitrate, and silver acetate; titanium compounds such as titanium tetrachloride, titanium tetrabromide, titanium(IV) methoxide, titanium(IV) ethoxide, titanium(IV) isopropoxide, and titanium (IV) oxide; palladium(II) compounds such as dichlorobis(triphenylphosphine)palladium and dichloro[1,1'-bis(diphenylphosphino)ferrocene]palladium; and nickel compounds such as nickel chloride, dichloro[1,2-bis(diphenylphosphino)ethane]nickel (II), and dichlorobis(triphenylphosphine)nickel(II). When the nucleophilic reagent, 6-(alkoxymethoxy)-3-hexenyl compound (11-a), is a Grignard reagent, that is, a 6-(alkoxymethoxy)-3-hexenylmagnesium halide compound (11-a: $M^1$=Mg$Z^1$), copper compounds, particularly cuprous halides such as cuprous chloride, cuprous bromide, and cuprous iodide, are preferred in view of the reactivity and/or economy.

The catalyst may be used alone or in combination thereof, if necessary. The catalyst may be commercially available one.

An amount of the catalyst used is preferably 0.0003 to 0.300 mol, more preferably 0.003 to 0.100 mol, per mol of the 6-halo-3-hexenyl alkoxymethyl ether compound (10-a) in view of the reaction rate and easy post-processing.

When the catalyst is used in the coupling reaction, a co-catalyst may also be incorporated, if necessary. Examples of the co-catalyst include a trialkyl phosphite compound having 3 to 9 carbon atoms, such as triethyl phosphite; and an arylphosphine compound having 18 to 44 carbon atoms, such as triphenylphosphine, tritolylphosphine, or 2,2'-bis(diphenylphosphino)-1,1'-binaphthyl (BINAP). A trialkyl phosphite, particularly triethyl phosphite, is preferred in view of the reactivity.

The co-catalyst may be used alone or in combination thereof, if necessary. The co-catalyst may be commercially available one.

An amount of the co-catalyst used is preferably 0.0001 to 1.00 mol, more preferably 0.001 to 0.300 mol, per mol of the 6-halo-3-hexenyl alkoxymethyl ether compound (10-a).

When the organolithium reagent is used in the coupling reaction, N,N,N',N'-tetramethylethylenediamine (TMEDA), hexamethylphosphoric triamide (HMPA), or N,N'-dimethylpropylene urea (DMPU) maybe incorporated to improve a reaction rate, if necessary.

When the catalyst is used in the coupling reaction, a lithium halide may also be incorporated, if necessary. Examples of the lithium halide include lithium chloride, lithium bromide, and lithium iodide. Lithium chloride is preferred in view of the reactivity.

An amount of the lithium halide used in the coupling reaction is preferably 0.0001 to 1.00 mol, more preferably 0.001 to 0.300 mol, per mol of the 6-halo-3-hexenyl alkoxymethyl ether compound (10-a), in view of the reactivity.

A reaction temperature in the coupling reaction varies, depending on the nucleophilic reagent, 6-(alkoxymethoxy)-3-hexenyl compound (11-a), and is preferably −78 to 80° C., more preferably −25 to 40° C. in view of the reactivity.

A reaction time in the coupling reaction varies, depending on a solvent and/or a reaction scale, and is preferably 0.5 to 100 hours in view of the reactivity.

The haloalkenyl alkoxymethyl ether compound (10) indicated in the aforesaid reaction scheme for preparing the compound (1) from the compound (7) will be explained below.

$R^1$ and $X^4$ in the general formula (10) are as defined for the general formula (1).

Specific examples of the haloalkenyl alkoxymethyl ether compound (10) include the following compounds:

7-halo-3-heptenyl alkoxymethyl ether compounds (a=3) such as 7-chloro-3-heptenyl methoxymethyl ether, 7-chloro-3-heptenyl ethoxymethyl ether, 7-bromo-3-heptenyl methoxymethyl ether, 7-bromo-3-heptenyl ethoxymethyl ether, 7-iodo-3-heptenyl methoxymethyl ether, and 7-iodo-3-heptenyl ethoxymethyl ether;

8-halo-3-octenyl alkoxymethyl ether compounds (a=4) such as 8-chloro-3-octenyl methoxymethyl ether, 8-chloro-3-octenyl ethoxymethyl ether, 8-bromo-3-octenyl methoxymethyl ether, 8-bromo-3-octenyl ethoxymethyl ether, 8-iodo-3-octenyl methoxymethyl ether, and 8-iodo-3-octenyl ethoxymethyl ether;

9-halo-3-nonanyl alkoxymethyl ether compounds (a=5) such as 9-chloro-3-nonanyl methoxymethyl ether, 9-chloro-3-nonanyl ethoxymethyl ether, 9-bromo-3-nonanyl methoxymethyl ether, 9-bromo-3-nonanyl ethoxymethyl ether, 9-iodo-3-nonanyl methoxymethyl ether, and 9-iodo-3-nonanyl ethoxymethyl ether;

10-halo-3-decenyl alkoxymethyl ether compounds (a=6) such as 10-chloro-3-decenyl methoxymethyl ether, 10-chloro-3-decenyl ethoxymethyl ether, 10-chloro-3-decenyl propoxymethyl ether, 10-chloro-3-decenyl butoxymethyl ether, 10-chloro-3-decenyl pentyloxymethyl ether, 10-chloro-3-decenyl hexyloxymethyl ether, 10-chloro-3-decenyl heptyloxymethyl ether, 10-chloro-3-decenyl octyloxymethyl ether, 10-chloro-3-decenyl nonyloxymethyl ether, 10-chloro-3-decenyl decyloxymethyl ether, 10-chloro-3-decenyl benzyloxymethyl ether, 10-bromo-3-decenyl methoxymethyl ether, 10-bromo-3-decenyl ethoxymethyl ether, 10-bromo-3-decenyl propoxymethyl ether, 10-bromo-3-decenyl butoxymethyl ether 10-bromo-3-decenyl pentyloxymethyl ether, 10-bromo-3-decenyl hexyloxymethyl ether, 10-bromo-3-decenyl heptyloxymethyl ether, 10-bromo-3-decenyl octyloxymethyl ether, 10-bromo-3-decenyl nonyloxymethyl ether, 10-bromo-3-decenyl decyloxymethyl ether, 10-bromo-3-decenyl benzyloxymethyl ether, 10-iodo-3-decenyl methoxymethyl ether, 10-iodo-3-decenyl ethoxymethyl ether, 10-iodo-3-decenyl propoxymethyl ether, 10-iodo-3-decenyl butoxymethyl ether, 10-iodo-3-decenyl pentyloxymethyl ether, 10-iodo-3-decenyl hexyloxymethyl ether, 10-iodo-3-decenyl heptyloxymethyl ether, 10-iodo-3-decenyl octyloxymethyl ether, 10-iodo-3-decenyl nonyloxymethyl ether, 10-iodo-3-decenyl decyloxymethyl ether, and 10-iodo-3-decenyl benzyloxymethyl ether;

11-halo-3-undecenyl alkoxymethyl ether compounds (a=7) such as 11-chloro-3-undecenyl methoxymethyl ether, 11-chloro-3-undecenyl ethoxymethyl ether, 11-bromo-3-undecenyl methoxymethyl ether, 11-bromo-3-undecenyl ethoxymethyl ether, 11-iodo-3-undecenyl methoxymethyl ether, and 11-iodo-3-undecenyl ethoxymethyl ether;

12-halo-3-dodecenyl alkoxymethyl ether compounds (a=8) such as 12-chloro-3-dodecenyl methoxymethyl ether, 12-chloro-3-dodecenyl ethoxymethyl ether, 12-bromo-3-dodecenyl methoxymethyl ether, 12-bromo-3-dodecenyl ethoxymethyl ether, 12-iodo-3-dodecenyl methoxymethyl ether, and 12-iodo-3-dodecenyl ethoxymethyl ether;

13-halo-3-tridecenyl alkoxymethyl ether compounds (a=9) such as 13-chloro-3-tridecenyl methoxymethyl ether, 13-chloro-3-tridecenyl ethoxymethyl ether, 13-bromo-3-tridecenyl methoxymethyl ether, 13-bromo-3-tridecenyl ethoxymethyl ether, 13-iodo-3-tridecenyl methoxymethyl ether, and 13-iodo-3-tridecenyl ethoxymethyl ether;

14-halo-3-tetradecenyl alkoxymethyl ether compounds (a=10) such as 14-chloro-3-tetradecenyl methoxymethyl ether, 14-chloro-3-tetradecenyl ethoxymethyl ether, 14-chloro-3-tetradecenyl propoxymethyl ether, 14-chloro-3-tetradecenyl butoxymethyl ether, 14-chloro-3-tetradecenyl pentyloxymethyl ether, 14-chloro-3-tetradecenyl hexyloxymethyl ether, 14-chloro-3-tetradecenyl heptyloxymethyl ether, 14-chloro-3-tetradecenyl octyloxymethyl ether, 14-chloro-3-tetradecenyl nonyloxymethyl ether, 14-chloro-3-tetradecenyl decyloxymethyl ether, 14-chloro-3-tetradecenyl benzyloxymethyl ether, 14-bromo-3-tetradecenyl methoxymethyl ether, 14-bromo-3-tetradecenyl ethoxymethyl ether, 14-bromo-3-tetradecenyl propoxymethyl ether, 14-bromo-3-tetradecenyl butoxymethyl ether, 14-bromo-3-tetradecenyl pentyloxymethyl ether, 14-bromo-3-tetradecenyl hexyloxymethyl ether, 14-bromo-3-tetradecenyl heptyloxymethyl ether, 14-bromo-3-tetradecenyl octyloxymethyl ether, 14-bromo-3-tetradecenyl nonyloxymethyl ether, 14-bromo-3-tetradecenyl decyloxymethyl ether, 14-bromo-3-tetradecenyl benzyloxymethyl ether, 14-iodo-3-tetradecenyl methoxymethyl ether, 14-iodo-3-tetradecenyl ethoxymethyl ether, 14-iodo-3-tetradecenyl propoxymethyl ether, 14-iodo-3-tetradecenyl butoxymethyl ether, 14-iodo-3-tetradecenyl pentyloxymethyl ether, 14-iodo-3-tetradecenyl hexyloxymethyl ether, 14-iodo-3-tetradecenyl heptyloxymethyl ether, 14-iodo-3-tetradecenyl octyloxymethyl ether, 14-iodo-3-tetradecenyl nonyloxymethyl ether, 14-iodo-3-tetradecenyl decyloxymethyl ether, and 14-iodo-3-tetradecenyl benzyloxymethyl ether;

15-halo-3-pentadecenyl alkoxymethyl ether compounds (a=11) such as 15-chloro-3-pentadecenyl methoxymethyl ether, 15-chloro-3-pentadecenyl ethoxymethyl ether, 15-bromo-3-pentadecenyl methoxymethyl ether, 15-bromo-3-pentadecenyl ethoxymethyl ether, 15-iodo-3-pentadecenyl methoxymethyl ether, and 15-iodo-3-pentadecenyl ethoxymethyl ether;

16-halo-3-hexadecenyl alkoxymethyl ether compounds (a=12) such as 16-chloro-3-hexadecenyl methoxymethyl ether, 16-chloro-3-hexadecenyl ethoxymethyl ether, 16-bromo-3-hexadecenyl methoxymethyl ether, 16-bromo-3-hexadecenyl ethoxymethyl ether, 16-iodo-3-hexadecenyl methoxymethyl ether, and 16-iodo-3-hexadecenyl ethoxymethyl ether;

17-halo-3-heptadecenyl alkoxymethyl ether compounds (a=13) such as 17-chloro-3-heptadecenyl methoxymethyl ether, 17-chloro-3-heptadecenyl ethoxymethyl ether, 17-bromo-3-heptadecenyl methoxymethyl ether, 17-bromo-3-heptadecenyl ethoxymethyl ether, 17-iodo-3-heptadecenyl methoxymethyl ether, and 17-iodo-3-heptadecenyl ethoxymethyl ether; and 18-halo-3-octadecenyl alkoxymethyl ether compounds (a=14) such as 18-chloro-3-octadecenyl methoxymethyl ether, 18-chloro-3-octadecenyl ethoxymethyl ether, 18-bromo-3-octadecenyl methoxymethyl ether, 18-bromo-3-octadecenyl ethoxymethyl ether, 18-iodo-3-octadecenyl methoxymethyl ether, and 18-iodo-3-octadecenyl ethoxymethyl ether.

One example of the process for synthesizing the (alkoxymethoxy)-3-alkenylmagnesium halide compound (11) comprises reacting the halo-3-alkenyl alkoxymethyl ether compound (10) with magnesium in a solvent to obtain an (alkoxymethoxy)-3-alkenylmagnesium halide compound (11: $M^2=MgZ^2$) which is a Grignard reagent, as shown in the following chemical reaction formula.

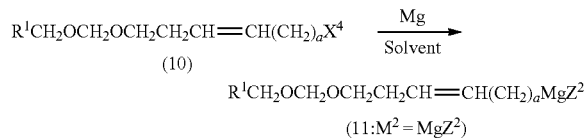

An amount of magnesium, the species and an amount of the solvent, a reaction temperature and a reaction time in the aforesaid chemical reaction are the same as those mentioned for the conversion with magnesium.

Another example of the process for synthesizing the nucleophilic reagent, (alkoxymethoxy)-3-alkenyl compound (11), comprises reacting the halo-3-alkenyl alkoxymethyl ether compound (10) with an organolithium reagent in a solvent to obtain an (alkoxymethoxy)-3-alkenyllithium compound (11: $M^2=Li$), as shown in the following chemical reaction formula.

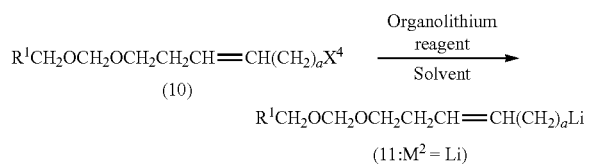

An amount of an organolithium reagent, the species and an amount of the solvent, a reaction temperature and a reaction time in the aforesaid chemical reaction formula are the same as those mentioned for the conversion with an organolithium reagent.

The nucleophilic reagent, (alkoxymethoxy)-3-alkenyl compound (11), indicated in the aforesaid reaction scheme for preparing the compound (1) from the compound (7) will be explained below.

$R^1$ in the general formula (11) is as defined for the general formula (1).

$M^2$ represents Li or $MgZ^2$, wherein $Z^2$ represents a halogen atom or an (alkoxymethoxy)-3-aklkenyl group. Examples of the halogen atom, $Z^2$, include a chlorine atom, a bromine atom, and an iodine atom.

Examples of the nucleophilic reagent, (alkoxymethoxy)-3-alkenyl compound (11), include (3E)-(alkoxymethoxy)-3-alkenyl compound of the following general formula (11-E), (3Z)-(alkoxymethoxy)-3-alkenyl compound of the following general formula (11-Z), and a mixture thereof.

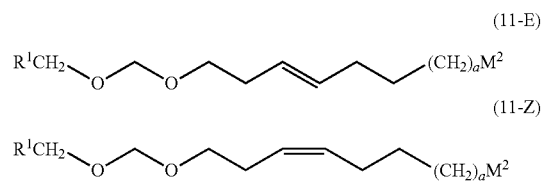

Specific examples of the nucleophilic reagent, (3E)-(alkoxymethoxy)-3-alkenyl compound (11-E), include the following compounds:

(3E)-(alkoxymethoxy)-3-alkenyllithium compounds such as (3E)-(methoxymethoxy)-3-alkenyllithium, (3E)-(ethoxymethoxy)-3-alkenyllithium, (3E)-(propoxymethoxy)-3-alkenyllithium, (3E)-(butoxymethoxy)-3-alkenyllithium, (3E)-(pentyloxymethoxy)-3-alkenyllithium, (3E)-(hexyloxymethoxy)-3-alkenyllithium, (3E)-(heptyloxymethoxy)-3-alkenyllithium, (3E)-(octyloxymethoxy)-3-alkenyllithium, (3E)-(nonyloxymethoxy)-3-alkenyllithium, and (3E)-(decyloxymethoxy)-3-alkenyllithium;

(3E)-(alkoxymethoxy)-3-alkenylmagnesium chloride compounds such as (3E)-(methoxymethoxy)-3-alkenylmagnesium chloride, (3E)-(ethoxymethoxy)-3-alkenylmagnesium chloride, (3E)-(propoxymethoxy)-3-alkenylmagnesium chloride, (3E)-(butoxymethoxy)-3-alkenylmagnesium chloride, (3E)-(pentyloxymethoxy)-3-alkenylmagnesium chloride, (3E)-(hexyloxymethoxy)-3-alkenylmagnesium chloride, (3E)-(heptyloxymethoxy)-3-alkenylmagnesium chloride, (3E)-(octyloxymethoxy)-3-alkenylmagnesium chloride, (3E)-(nonyloxymethoxy)-3-alkenylmagnesium chloride, and (3E)-(decyloxymethoxy)-3-alkenylmagnesium chloride;

(3E)-(alkoxymethoxy)-3-alkenylmagnesium bromide compounds such as (3E)-(methoxymethoxy)-3-alkenylmagnesium bromide, (3E)-(ethoxymethoxy)-3-alkenylmagnesium bromide, (3E)-(propoxymethoxy)-3-alkenylmagnesium bromide, (3E)-(butoxymethoxy)-3-alkenylmagnesium bromide, (3E)-(pentyloxymethoxy)-3-alkenylmagnesium bromide, (3E)-(hexyloxymethoxy)-3-alkenylmagnesium bromide, (3E)-(heptyloxymethoxy)-3-alkenylmagnesium bromide, (3E)-(octyloxymethoxy)-3-alkenylmagnesium bromide, (3E)-(nonyloxymethoxy)-3-alkenylmagnesium bromide, and (3E)-(decyloxymethoxy)-3-alkenylmagnesium bromide; and (3E)-(alkoxymethoxy)-3-alkenylmagnesium iodide compounds such as (3E)-(methoxymethoxy)-3-alkenylmagnesium iodide, (3E)-(ethoxymethoxy)-3-alkenylmagnesium iodide, (3E)-(propoxymethoxy)-3-alkenylmagnesium iodide, (3E)-(butoxymethoxy)-3-alkenylmagnesium iodide, (3E)-(pentyloxymethoxy)-3-alkenylmagnesium iodide, (3E)-(hexyloxymethoxy)-3-alkenylmagnesium iodide, (3E)-(heptyloxymethoxy)-3-alkenylmagnesium iodide, (3E)-(octyloxymethoxy)-3-alkenylmagnesium iodide, (3E)-(nonyloxymethoxy)-3-alkenylmagnesium iodide, and (3E)-(decyloxymethoxy)-3-alkenylmagnesium iodide.

Among these, (3E)-(alkoxymethoxy)-3-alkenylmagnesium halide compounds such as (3E)-(alkoxymethoxy)-3-alkenylmagnesium chloride compounds are preferred in view of the availability.

Specific examples of the nucleophilic reagent, (3Z)-(alkoxymethoxy)-3-alkenyl compound (11-Z), include the following compounds:

(3Z)-(alkoxymethoxy)-3-alkenyllithium compounds such as (3Z)-(methoxymethoxy)-3-alkenyllithium, (3Z)-

(ethoxymethoxy)-3-alkenyllithium, (3Z)-(propoxymethoxy)-3-alkenyllithium, (3Z)-(butoxymethoxy)-3-alkenyllithium, (3Z)-(pentyloxymethoxy)-3-alkenyllithium, (3Z)-(hexyloxymethoxy)-3-alkenyllithium, (3Z)-(heptyloxymethoxy)-3-alkenyllithium, (3Z)-(octyloxymethoxy)-3-alkenyllithium, (3Z)-(nonyloxymethoxy)-3-alkenyllithium, and (3Z)-(decyloxymethoxy)-3-alkenyllithium;

(3Z)-(alkoxymethoxy)-3-alkenylmagnesium chloride compounds such as (3Z)-(methoxymethoxy)-3-alkenylmagnesium chloride, (3Z)-(ethoxymethoxy)-3-alkenylmagnesium chloride, (3Z)-(propoxymethoxy)-3-alkenylmagnesium chloride, (3Z)-(butoxymethoxy)-3-alkenylmagnesium chloride, (3Z)-(pentyloxymethoxy)-3-alkenylmagnesium chloride, (3Z)-(hexyloxymethoxy)-3-alkenylmagnesium chloride, (3Z)-(heptyloxymethoxy)-3-alkenylmagnesium chloride, (3Z)-(octyloxymethoxy)-3-alkenylmagnesium chloride, (3Z)-(nonyloxymethoxy)-3-alkenylmagnesium chloride, and (3Z)-(decyloxymethoxy)-3-alkenylmagnesium chloride;

(3Z)-(alkoxymethoxy)-3-alkenylmagnesium bromide compounds such as (3Z)-(methoxymethoxy)-3-alkenylmagnesium bromide, (3Z)-(ethoxymethoxy)-3-alkenylmagnesium bromide, (3Z)-(propoxymethoxy)-3-alkenylmagnesium bromide, (3Z)-(butoxymethoxy)-3-alkenylmagnesium bromide, (3Z)-(pentyloxymethoxy)-3-alkenylmagnesium bromide, (3Z)-(hexyloxymethoxy)-3-alkenylmagnesium bromide, (3Z)-(heptyloxymethoxy)-3-alkenylmagnesium bromide, (3Z)-(octyloxymethoxy)-3-alkenylmagnesium bromide, (3Z)-(nonyloxymethoxy)-3-alkenylmagnesium bromide, and (3Z)-(decyloxymethoxy)-3-alkenylmagnesium bromide; and (3Z)-(alkoxymethoxy)-3-alkenylmagnesium iodide compounds such as (3Z)-(methoxymethoxy)-3-alkenylmagnesium iodide, (3Z)-(ethoxymethoxy)-3-alkenylmagnesium iodide, (3Z)-(propoxymethoxy)-3-alkenylmagnesium iodide, (3Z)-(butoxymethoxy)-3-alkenylmagnesium iodide, (3Z)-(pentyloxymethoxy)-3-alkenylmagnesium iodide, (3Z)-(hexyloxymethoxy)-3-alkenylmagnesium iodide, (3Z)-(heptyloxymethoxy)-3-alkenylmagnesium iodide, (3Z)-(octyloxymethoxy)-3-alkenylmagnesium iodide, (3Z)-(nonyloxymethoxy)-3-alkenylmagnesium iodide, and (3Z)-(decyloxymethoxy)-3-alkenylmagnesium iodide.

Among these, (3Z)-(alkoxymethoxy)-3-alkenylmagnesium halide compounds such as (3Z)-(alkoxymethoxy)-3-alkenylmagnesium chloride compounds are preferred in view of the availability.

The nucleophilic reagent, (alkoxymethoxy)-3-alkenyl compound (11), may be used alone or in combination thereof, if necessary.

The nucleophilic reagent, (alkoxymethoxy)-3-alkenyl compound (11), may be commercially available one or may be prepared in house.

The orthoformate ester compound (13) indicated in the aforesaid reaction scheme for preparing the compound (1) from the compound (7) will be explained below.

The orthoformate ester compounds are represented by the following general formula (13).

$$HC(OR^7)_3 \quad (13)$$

Three $R^7$'s in the orthoformate ester compound (13) may be same with or different from each other and represent an alkyl group having 1 to 6 carbon atoms, preferably 1 to 3 carbon atoms.

Examples of the alkyl group having 1 to 6 carbon atoms include linear alkyl groups such as a methyl group, an ethyl group, an n-propyl group, an n-butyl group, an n-pentyl group and an n-hexyl group; and branched alkyl groups such as an isopropyl group and an isobutyl group.

Examples of the orthoformate ester compound (13) include methyl orthoformate, ethyl orthoformate, propyl orthoformate, butyl orthoformate, pentyl orthoformate, and hexyl orthoformate, with methyl orthoformate and ethyl orthoformate being preferred in view of availability.

The orthoformate ester compound (13) may be used either alone or in combination thereof. The orthoformate ester compound (13) may be commercially available one.

Examples of a solvent used in the nucleophilic substitution reaction includes hydrocarbons such as toluene, xylene, and hexane; and ethers such as tetrahydrofuran, 4-methyltetrahydropyran, and diethyl ether, with tetrahydrofuran, toluene, and 4-methyltetrahydropyran being preferred in view of the reactivity.

The solvent may be used alone or in combination thereof, if necessary. The solvent may be commercially available one.

When the nucleophilic reagent, (alkoxymethoxy)-3-alkenyl compound (11), is diluted with a solvent, or when a solvent is used in the preparation of the nucleophilic reagent, (alkoxymethoxy)-3-alkenyl compound (11), such a solvent may be common with the solvent used in the nucleophilic substitution reaction or may be different from the solvent used in the nucleophilic substitution reaction.

In a case where the solvents are not common, a solvent used in the preparation of compound (11) may be replaced, in the nucleophilic substitution reaction step, with a solvent which increases a reaction rate of the nucleophilic substitution reaction.

For instance, in a case where tetrahydrofuran is used in preparing the nucleophilic reagent, (alkoxymethoxy)-3-alkenyl compound (11), and toluene is selected as a solvent for the nucleophilic substitution reaction, the nucleophilic reagent, (alkoxymethoxy)-3-alkenyl compound (11) containing tetrahydrofuran is placed in a reactor containing the orthoformic ester compound and toluene, and tetrahydrofuran is distilled off in a course of raising a reaction temperature, so that tetrahydrofuran may be replaced with toluene gradually in the nucleophilic substitution reaction system.

An amount of the solvent is preferably from 100 to 6000 g per mol of the orthoformate ester compound (13) in view of the reactivity.

A reaction temperature in the nucleophilic substitution reaction is preferably from 75 to 130° C. in view to smoothly proceed with the reaction and prevent evaporation of the solvent.

A reaction time in the nucleophilic substitution reaction varies, depending on a solvent used or a production scale, and is preferably from 1 to 100 hours.

When "a" is an integer of 1, the dialkoxyalkenyl alkoxymethyl ether compound (1), i.e., dialkoxypentenyl alkoxymethyl ether compound (1; a=1) may be synthesized, for example, as shown in the following chemical reaction formula including the three steps.

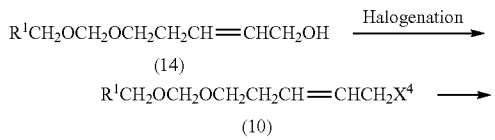

-continued

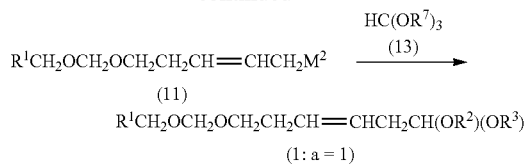

First, the hydroxy group of the 5-hydroxy-3-pentenyl alkoxymethyl ether compound of the general formula (14) is halogenated to obtain a 5-halo-3-pentenyl alkoxymethyl ether compound of the general formula (10) (first step). The obtained 5-halo-3-pentenyl alkoxymethyl ether compound (10) is reacted with, for example, magnesium or an organolithium reagent in a solvent to obtain a nucleophilic reagent, 5-(alkoxymethoxy)-3-pentenyl compound of the general formula (11) (second step). Then, the obtained nucleophilic reagent, 5-(alkoxymethoxy)-3-pentenyl compound (11), is subjected to a nucleophilic substitution reaction with an orthoformate ester compound of the general formula (13) for acetalization to thereby obtain the dialkoxypentenyl alkoxymethyl ether compound (1) (third step).

When "a" is an integer of 3 or 4, the dialkoxyalkenyl alkoxymethyl ether compound (1) may be synthesized, for example, as shown in the following chemical reaction formula including four steps.

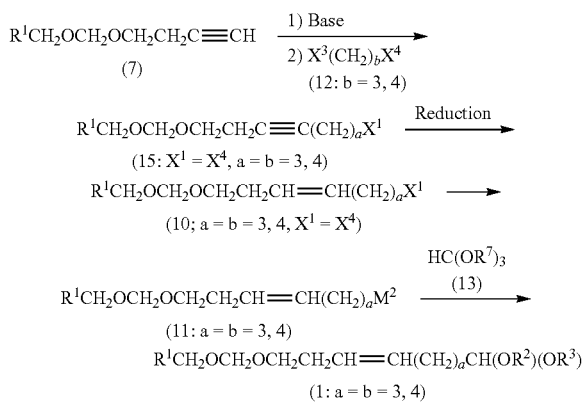

First, an alkoxymethyl 3-butynyl ether compound of the general formula (7) is reacted with a base and then subjected to a coupling reaction with a dihaloalkane of the general formula (12) to obtain a halo-3-alkynyl alkoxymethyl ether compound of the general formula (15) (first step). The carbon-carbon triple bond of the obtained halo-3-alkynyl alkoxymethyl ether compound of the general formula (15) is reduced to obtain a halo-3-alkenyl alkoxymethyl ether compound of the general formula (10) (second step). The obtained halo-3-alkenyl alkoxymethyl ether compound (10) is reacted with, for example, magnesium or an organolithium reagent in a solvent to obtain the nucleophilic reagent, (alkoxymethoxy)-3-alkenyl compound (11) (third step). Then, the obtained nucleophilic reagent, (alkoxymethoxy)-3-alkenyl compound (11), is subjected to a nucleophilic substitution reaction with an orthoformate ester compound of the general formula (13) for acetalization to thereby obtain the dialkoxyalkenyl alkoxymethyl ether compound (1) (forth step).

Preparation of the dialkoxy-3-alken-1-ol Compound (2) Through Dealkoxymethylation The dialkoxy-3-alken-1-ol compound (2) may be prepared by dealkoxymethylating the dialkoxyalkenyl alkoxymethyl ether compound (1), as shown in the following chemical reaction formula.

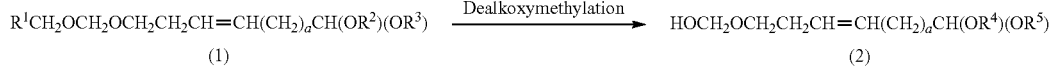

One or plural species of the dialkoxyalkenyl alkoxymethyl ether compound (1) may be used in the dealkoxymethylation, if necessary.

For example, a mixture of a (3E)-12,12-dialkoxy-3-dodecenyl methoxymethyl ether compound (1: $R^1$=H; a=7) and a (3Z)-12,12-dialkoxy-3-dodecenyl methoxymethyl ether compound (1: $R^1$=H; a=7) will give a mixture of a (3E)-12,12-dialkoxy-3-dodecen-1-ol compound (2: a=7) and a (3Z)-12,12-dialkoxy-3-dodecen-1-ol compound (2: a=7).

Optimal conditions of the dealkoxymethylation varies, depending on $R^1$. For example, when $R^1$ is a phenyl group, the dealkoxymethylation may be carried out in Birch reduction conditions in which sodium is used in liquid ammonia. When $R^1$ is a hydrogen atom or an n-alkyl group such as a methyl group, the dealkoxymethylation may be carried out using an acid or an alcohol compound (6) mentioned below.

Examples of the acid include inorganic acids such as hydrochloric acid and hydrobromic acid; sulfonic acids such as p-toluenesulfonic acid and benzenesulfonic acid; organic acids such as trifluoroacetic acid, acetic acid, formic acid, and oxalic acid; and Lewis acids such as iodotrimethylsilane and titanium tetrachloride. p-Toluenesulfonic acid, benzenesulfonic acid and hydrochloric acid, particularly p-toluenesulfonic acid, are preferred in view of the suppression of side reactions.

The acid may be used alone or in combination thereof, if necessary. The acid may be commercially available one.

An amount of the acid used is preferably 0.0001 to 10.0 mol, more preferably 0.001 to 1.0 mol, per mol of the dialkoxyalkenyl alkoxymethyl ether compound (1).

The alcohol compound (6) is represented by the following general formula (6):

$$R^6OH \quad (6)$$

$R^6$ represents a monovalent hydrocarbon group having 1 to 15 carbon atoms, preferably having 1 to 6 carbon atoms, in view of the price or availability. The monovalent hydrocarbon group is as defined for $R^2$ and $R^3$ of the general formula (1).

Examples of the alcohol compound (6) include linear alcohols such as methanol, ethanol, n-propanol, n-butanol, n-pentanol, n-hexanol, n-heptanol, n-octanol, n-nonanol, n-decanol, n-undecanol, n-dodecanol, n-tridecanol, n-tetradecanol, and n-pentadecanol; branched alcohols such as isopropanol and 2-butanol; and diols such as ethyleneglycol, propyleneglycol, 2-methyl-1,3-propanediol, 2,2-dimethyl-1,3-propanediol, 1,2-dimethyl-1,3-propanediol, 1,3-dimethyl-1,3-propanediol, and 2-methyl-1,4-butanediol. Methanol and ethanol, particularly methanol, are preferred in view of the reactivity.

Transacetalization will occur simultaneously with the dealkoxymethylation of the interest in acidic conditions. Meanwhile, if $R^2$ and $R^3$ in the dialkoxyalkenyl alkoxymethyl ether compound (1) is same as $R^6$ in $R^6OH$ (6), the alkoxy group of the acetal cannot change. Accordingly, $R^6OH$ (6) is preferred in which $R^6$ is same as $R^2$ and $R^3$.

Alternatively, the transacetalization may be carried out with $R^6OH$ (6) in which $R^6$ is purposely different from $R^2$ and $R^3$, so that at least one of $R^2$ and $R^3$ in the dialkoxyalkenyl alkoxymethyl ether compound (1) is replaced with $R^4$ and $R^5$ which are different from $R^2$ or $R^3$. To this end, $R^6OH$ (6) is preferred in which $R^6$ is same as $R^4$ or $R^5$, or $R^4$ and $R^5$ (i.e., $R^4=R^5$). In this manner, the replacement of $R^2$ and $R^3$ in the acetal with $R^4$ and $R^5$ makes it possible to adjust a boiling point of the dialkoxy-3-alken-1-ol compound (2) or stability of the acetal.

The alcohol compound (6) may be used alone or in combination thereof, if necessary.

The alcohol compound (6) may be commercially available one.

An amount of the alcohol compound (6) used is preferably 1 to 1,000 mol, more preferably 3 to 100 mol, per mol of the dialkoxyalkenyl alkoxymethyl ether compound (1) in view of the reactivity.

A solvent other than the alcohol compound (6) may be used in the dealkoxymethylation, if necessary.

Examples of the solvent include usual solvents, for example, ethers such as diethyl ether, dibutyl ether, 4-methyltetrahydropyran, tetrahydrofuran (THF), cyclopentylmethylether, and 1,4-dioxane; hydrocarbons such as hexane, heptane, benzene, toluene, xylene, and cumene; chlorinated solvents such as trichloroethylene, dichloromethane, and chloroform; aprotic polar solvents such as dimethyl sulfoxide, γ-butyrolactone (GBL), N-methylpyrrolidone (NMP), N,N-dimethylformamide (DMF), N,N-dimethylacetamide (DMAC), and hexamethylphosphoric triamide (HMPA); nitriles such as acetonitrile and propionitrile; and esters such as methyl acetate, ethyl acetate, n-propyl acetate, and n-butyl acetate.

The solvent may be used alone or in combination thereof, if necessary. The solvent may be commercially available one.

An amount of the solvent used in the dealkoxymethylation is preferably 0 to 2,000 g, more preferably 0 to 500 g, per mol of the dialkoxyalkenyl alkoxymethyl ether compound (1).

The solvent occupies a space of a reactor to reduce a space for starting material, resulting in a decreased productivity. Therefore, the dealkoxymethylation may be carried out without a solvent.

A reaction temperature in the dealkoxymethylation varies, depending on a dialkoxyalkenyl alkoxymethyl ether compound (1) to be used, and is preferably 5 to 180° C. in view of the reactivity.

A reaction time in the dealkoxymethylation varies, depending on a dialkoxyalkenyl alkoxymethyl ether compound (1) and/or a reaction scale, and is preferably 1 to 100 hours in view of the reactivity.

In the dealkoxymethylation, a by-produced alkoxymethoxymethane may be distilled off from the reaction system, if necessary, whereby the equilibrium is shifted to the product side to reduce the reaction time.

Among the dialkoxyacetal, which is a protecting group for the carbonyl group, and an alkoxymethyl group which is a protecting group for the hydroxyl group, both of which exists in one and the same molecule of the dialkoxyalkenyl alkoxymethyl ether compound (1), it is difficult to selectively hydrolyze the alkoxymethyl group to cause dealkoxymethylation, and the easier hydrolysable dialkoxyacetal may be hydrolyzed first. Therefore, it is important in view of the yield to cause dealkoxymethylation in conditions where aldehyde which occurred by hydrolyzation of the dialkoxyacetal is immediately re-acetalyzed. Isomerization of the carbon-carbon double bond may occur in some conditions, whereby the geometric selectivity is lowered. Accordingly, proper selection of reaction conditions is important.

The dialkoxy-3-alken-1-ol compound (2) will be explained below.

$R^4$ and $R^5$ in the general formula (2) represent, independently of each other, a monovalent hydrocarbon group having 1 to 15 carbon atoms, or $R^4$ and $R^5$ may form together a divalent hydrocarbon group, $R^4$-$R^5$, having 2 to 10 carbon atoms, and "a" is as defined for the general formula (1).

Specific examples of the dialkoxy-3-alken-1-ol compound (2) include the following compounds:

(3E)-6,6-dialkoxy-3-hexen-1-ol compounds such as (3E)-6,6-dimethoxy-3-hexen-1-ol, (3E)-6,6-diethoxy-3-hexen-1-ol, (3E)-6,6-dipropoxy-3-hexen-1-ol, (3E)-6,6-dibutoxy-3-hexen-1-ol, (3E)-6,6-dipentyloxy-3-hexen-1-ol, (3E)-6,6-dihexyloxy-3-hexen-1-ol, (3E)-6,6-diheptyloxy-3-hexen-1-ol, (3E)-6,6-dioctyloxy-3-hexen-1-ol, (3E)-6,6-dinonyloxy-3-hexen-1-ol, and (3E)-6,6-didecyloxy-3-hexen-1-ol;

(3E)-7,7-dialkoxy-3-hepten-1-ol compounds such as (3E)-7,7-dimethoxy-3-hepten-1-ol, (3E)-7,7-diethoxy-3-hepten-1-ol, (3E)-7,7-dipropoxy-3-hepten-1-ol, (3E)-7,7-dibutoxy-3-hepten-1-ol, (3E)-7,7-dipentyloxy-3-hepten-1-ol, (3E)-7,7-dihexyloxy-3-hepten-1-ol, (3E)-7,7-diheptyloxy-3-hepten-1-ol, (3E)-7,7-dioctyloxy-3-hepten-1-ol, (3E)-7,7-dinonyloxy-3-hepten-1-ol, and (3E)-7,7-didecyloxy-3-hepten-1-ol;

(3E)-8,8-dialkoxy-3-octen-1-ol compounds such as (3E)-8,8-dimethoxy-3-octen-1-ol, (3E)-8,8-diethoxy-3-octen-1-ol, (3E)-8,8-dipropoxy-3-octen-1-ol, (3E)-8,8-dibutoxy-3-octen-1-ol, (3E)-8,8-dipentyloxy-3-octen-1-ol, (3E)-8,8-dihexyloxy-3-octen-1-ol, (3E)-8,8-diheptyloxy-3-octen-1-ol, (3E)-8,8-dioctyloxy-3-octen-1-ol, (3E)-8,8-dinonyloxy-3-octen-1-ol, and (3E)-8,8-didecyloxy-3-octen-1-ol;

(3E)-9,9-dialkoxy-3-nonen-1-ol compounds such as (3E)-9,9-dimethoxy-3-nonen-1-ol, (3E)-9,9-diethoxy-3-nonen-1-ol, (3E)-9,9-dipropoxy-3-nonen-1-ol, (3E)-9,9-dibutoxy-3-nonen-1-ol, (3E)-9,9-dipentyloxy-3-nonen-1-ol, (3E)-9,9-dihexyloxy-3-nonen-1-ol, (3E)-9,9-diheptyloxy-3-nonen-1-ol, (3E)-9,9-dioctyloxy-3-nonen-1-ol, (3E)-9,9-dinonyloxy-3-nonen-1-ol, and (3E)-9,9-didecyloxy-3-nonen-1-ol;

(3E)-10,10-dialkoxy-3-decen-1-ol compounds such as (3E)-10,10-dimethoxy-3-decen-1-ol, (3E)-10,10-diethoxy-3-decen-1-ol, (3E)-10,10-dipropoxy-3-decen-1-ol, (3E)-10,10-dibutoxy-3-decen-1-ol, (3E)-10,10-dipentyloxy-3-decen-1-ol, (3E)-10,10-dihexyloxy-3-decen-1-ol, (3E)-10,10-diheptyloxy-3-decen-1-ol, (3E)-10,10-dioctyloxy-3-decen-1-ol, (3E)-10, 10-dinonyloxy-3-decen-1-ol, and (3E)-10,10-didecyloxy-3-decen-1-ol;

(3E)-11,11-dialkoxy-3-undecen-1-ol compounds such as (3E)-11,11-dimethoxy-3-undecen-1-ol, (3E)-11,11-diethoxy-3-undecen-1-ol, (3E)-11,11-dipropoxy-3-undecen-1-ol, (3E)-11,11-dibutoxy-3-undecen-1-ol, (3E)-11,11-dipentyloxy-3-undecen-1-ol, (3E)-11,11-dihexyloxy-3-undecen-1-ol, (3E)-11,11-diheptyloxy-3-undecen-1-ol, (3E)-11,11-dioctyloxy-3-undecen-1-ol, (3E)-11,11-dinonyloxy-3-undecen-1-ol, and (3E)-11,11-didecyloxy-3-undecen-1-ol;

(3E)-12,12-dialkoxy-3-dodecen-1-ol compounds such as (3E)-12,12-dimethoxy-3-dodecen-1-ol, (3E)-12,12-diethoxy-3-dodecen-1-ol, (3E)-12,12-dipropoxy-3-dodecen-1-ol, (3E)-12,12-dibutoxy-3-dodecen-1-ol, (3E)-12,12-dipentyloxy-3-dodecen-1-ol, (3E)-12,12-dihexyloxy-3-dodecen-1-ol, (3E)-12,12-diheptyloxy--dodecen-1-ol, (3E)-12,12-dioctyloxy-3-dodecen-1-ol, (3E)-12,12-dinonyloxy-3-dodecen-1-ol, and (3E)-12,12-didecyloxy-3-dodecen-1-ol;

(3E)-13,13-dialkoxy-3-tridecen-1-ol compounds such as (3E)-13,13-dimethoxy-3-tridecen-1-ol, (3E)-13,13-diethoxy-3-tridecen-1-ol, (3E)-13,13-dipropoxy-3-tridecen-1-ol, (3E)-13,13-dibutoxy-3-tridecen-1-ol, (3E)-13,13-dipentyloxy-3-tridecen-1-ol, (3E)-13,13-dihexyloxy-3-tridecen-1-ol, (3E)-13,13-diheptyloxy-3-tridecen-1-ol, (3E)-13,13-dioctyloxy-3-tridecen-1-ol, (3E)-13, 13-dinonyloxy-3-tridecen-1-ol, and (3E)-13,13-didecyloxy-3-tridecen-1-ol;

(3E)-14,14-dialkoxy-3-tetradecen-1-ol compounds such as (3E)-14,14-dimethoxy-3-tetradecen-1-ol, (3E)-14,14-diethoxy-3-tetradecen-1-ol, (3E)-14,14-dipropoxy-3-tetradecen-1-ol, (3E)-14,14-dibutoxy-3-tetradecen-1-ol, (3E)-14,14-dipentyloxy-3-tetradecen-1-ol, (3E)-14,14-dihexyloxy-3-tetradecen-1-ol, (3E)-14,14-diheptyloxy-3-tetradecen-1-ol, (3E)-14,14-dioctyloxy-3-tetradecen-1-ol, (3E)-14,14-dinonyloxy 3-tetradecen-1-ol, and (3E)-14,14-didecyloxy-3-tetradecen-1-ol;

(3E)-15,15-dialkoxy-3-pentadecen-1-ol compounds such as (3E)-15,15-dimethoxy-3-pentadecen-1-ol, (3E)-15,15-diethoxy-3-pentadecen-1-ol, (3E)-15,15-dipropoxy-3-pentadecen-1-ol, (3E)-15,15-dibutoxy-3-pentadecen-1-ol, (3E)-15,15-dipentyloxy-3-pentadecen-1-ol, (3E)-15,15-dihexyloxy-3-pentadecen-1-ol, (3E)-15,15-diheptyloxy-3-pentadecen-1-ol, (3E)-15,15-dioctyloxy-3-pentadecen-1-ol, (3E)-15,15-dinonyloxy-3-pentadecen-1-ol, and (3E)-15,15-didecyloxy-3-pentadecen-1-ol;

(3E)-16,16-dialkoxy-3-hexadecen-1-ol compounds such as (3E)-16,16-dimethoxy-3-hexadecen-1-ol, (3E)-16,16-diethoxy-3-hexadecen-1-ol, (3E)-16,16-dipropoxy-3-hexadecen-1-ol, (3E)-16,16-dibutoxy-3-hexadecen-1-ol, (3E)-16,16-dipentyloxy-3-hexadecen-1-ol, (3E)-16,16-dihexyloxy-3-hexadecen-1-ol, (3E)-16,16-diheptyloxy-3-hexadecen-1-ol, (3E)-16,16-dioctyloxy-3-hexadecen-1-ol, (3E)-16,16-dinonyloxy-3-hexadecen-1-ol, and (3E)-16,16-didecyloxy-3-hexadecen-1-ol;

(3E)-17,17-dialkoxy-3-heptadecen-1-ol compounds such as (3E)-17,17-dimethoxy-3-heptadecen-1-ol, (3E)-17,17-diethoxy-3-heptadecen-1-ol, (3E)-17,17-dipropoxy-3-heptadecen-1-ol, (3E)-17,17-dibutoxy-3-heptadecen-1-ol, (3E)-17,17-dipentyloxy-3-heptadecen-1-ol, (3E)-17,17-dihexyloxy-3-heptadecen-1-ol, (3E)-17,17-diheptyloxy-3-heptadecen-1-ol, (3E)-17,17-dioctyloxy-3-heptadecen-1-ol, (3E)-17,17-dinonyloxy-3-heptadecen-1-ol, and (3E)-17,17-didecyloxy-3-heptadecen-1-ol;

(3E)-18,18-dialkoxy-3-octadecen-1-ol compounds such as (3E)-18,18-dimethoxy-3-octadecen-1-ol, (3E)-18,18-diethoxy-3-octadecen-1-ol, (3E)-18,18-dipropoxy-3-octadecen-1-ol, (3E)-18,18-dibutoxy-3-octadecen-1-ol, (3E)-18,18-dipentyloxy-3-octadecen-1-ol, (3E)-18,18-dihexyloxy-3-octadecen-1-ol, (3E)-18,18-diheptyloxy-3-octadecen-1-ol, (3E)-18,18-dioctyloxy-3-octadecen-1-ol, (3E)-18,18-dinonyloxy-3-octadecen-1-ol, and (3E)-18,18-didecyloxy-3-octadecen-1-ol;

(3Z)-6,6-dialkoxy-3-hexen-1-ol compounds such as (3Z)-6,6-dimethoxy-3-hexen-1-ol, (3Z)-6,6-diethoxy-3-hexen-1-ol, (3Z)-6,6-dipropoxy-3-hexen-1-ol, (3Z)-6,6-dibutoxy-3-hexen-1-ol, (3Z)-6,6-dipentyloxy-3-hexen-1-ol, (3Z)-6,6-dihexyloxy-3-hexen-1-ol, (3Z)-6,6-diheptyloxy-3-hexen-1-ol, (3Z)-6,6-dioctyloxy-3-hexen-1-ol, (3Z)-6,6-dinonyloxy-3-hexen-1-ol, and (3Z)-6,6-didecyloxy-3-hexen-1-ol;

(3Z)-7,7-dialkoxy-3-hepten-1-ol compounds such as (3Z)-7,7-dimethoxy-3-hepten-1-ol, (3Z)-7,7-diethoxy-3-hepten-1-ol, (3Z)-7,7-dipropoxy-3-hepten-1-ol, (3Z)-7,7-dibutoxy-3-hepten-1-ol, (3Z)-7,7-dipentyloxy-3-hepten-1-ol, (3Z)-7,7-dihexyloxy-3-hepten-1-ol, (3Z)-7,7-diheptyloxy-3-hepten-1-ol, (3Z)-7,7-dioctyloxy-3-hepten-1-ol, (3Z)-7,7-dinonyloxy-3-hepten-1-ol, and (3Z)-7,7-didecyloxy-3-hepten-1-ol;

(3Z)-8,8-dialkoxy-3-octen-1-ol compounds such as (3Z)-8,8-dimethoxy-3-octen-1-ol, (3Z)-8,8-diethoxy-3-octen-1-ol, (3Z)-8,8-dipropoxy-3-octen-1-ol, (3Z)-8,8-dibutoxy-3-octen-1-ol, (3Z)-8,8-dipentyloxy-3-octen-1-ol, (3Z)-8,8-dihexyloxy-3-octen-1-ol, (3Z)-8,8-diheptyloxy-3-octen-1-ol, (3Z)-8,8-dioctyloxy-3-octen-1-ol, (3Z)-8,8-dinonyloxy-3-octen-1-ol, and (3Z)-8,8-didecyloxy-3-octen-1-ol;

(3Z)-9,9-dialkoxy-3-nonen-1-ol compounds such as (3Z)-9,9-dimethoxy-3-nonen-1-ol, (3Z)-9,9-diethoxy-3-nonen-1-ol, (3Z)-9,9-dipropoxy-3-nonen-1-ol, (3Z)-9,9-dibutoxy-3-nonen-1-ol, (3Z)-9,9-dipentyloxy-3-nonen-1-ol, (3Z)-9,9-dihexyloxy-3-nonen-1-ol, (3Z)-9,9-diheptyloxy-3-nonen-1-ol, (3Z)-9,9-dioctyloxy-3-nonen-1-ol, (3Z)-9,9-dinonyloxy-3-nonen-1-ol, and (3Z)-9,9-didecyloxy-3-nonen-1-ol;

(3Z)-10,10-dialkoxy-3-decen-1-ol compounds such as (3Z)-10,10-dimethoxy-3-decen-1-ol, (3Z)-10,10-diethoxy-3-decen-1-ol, (3Z)-10,10-dipropoxy-3-decen-1-ol, (3Z)-10,10-dibutoxy-3-decen-1-ol, (3Z)-10,10-dipentyloxy-3-decen-1-ol, (3Z)-10,10-dihexyloxy-3-decen-1-ol, (3Z)-10,10-diheptyloxy-3-decen-1-ol, (3Z)-10,10-dioctyloxy-3-decen-1-ol, (3Z)-10, 10-dinonyloxy-3-decen-1-ol, and (3Z)-10,10-didecyloxy-3-decen-1-ol;

(3Z)-11,11-dialkoxy-3-undecen-1-ol compounds such as (3Z)-11,11-dimethoxy-3-undecen-1-ol, (3Z)-11,11-diethoxy-3-undecen-1-ol, (3Z)-11,11-dipropoxy-3-undecen-1-ol, (3Z)-11,11-dibutoxy-3-undecen-1-ol, (3Z)-11,11-dipentyloxy-3-undecen-1-ol, (3Z)-11,11-dihexyloxy-3-undecen-1-ol, (3Z)-11,11-diheptyloxy-3-undecen-1-ol, (3Z)-11,11-dioctyloxy-3-undecen-1-ol, (3Z)-11,11-dinonyloxy-3-undecen-1-ol, and (3Z)-11,11-didecyloxy-3-undecen-1-ol;

(3Z)-12,12-dialkoxy-3-dodecen-1-ol compounds such as (3Z)-12,12-dimethoxy-3-dodecen-1-ol, (3Z)-12,12-diethoxy-3-dodecen-1-ol, (3Z)-12,12-dipropoxy-3-dodecen-1-ol, (3Z)-12,12-dibutoxy-3-dodecen-1-ol, (3Z)-12,12-dipentyloxy-3-dodecen-1-ol, (3Z)-12,12-dihexyloxy-3-dodecen-1-ol, (3Z)-12,12-diheptyloxy-3-dodecen-1-ol, (3Z)-12,12-dioctyloxy-3-dodecen-1-ol, (3Z)-12,12-dinonyloxy-3-dodecen-1-ol, and (3Z)-12,12-didecyloxy-3-dodecen-1-ol;

(3Z)-13,13-dialkoxy-3-tridecen-1-ol compounds such as (3Z)-13,13-dimethoxy-3-tridecen-1-ol, (3Z)-13,13-diethoxy-3-tridecen-1-ol, (3Z)-13,13-dipropoxy-3-tridecen-1-ol, (3Z)-13,13-dibutoxy-3-tridecen-1-ol, (3Z)-13,13-dipentyloxy-3-tridecen-1-ol, (3Z)-13,13-dihexyloxy-3-tridecen-1-ol, (3Z)-13,13-diheptyloxy-3-tridecen-1-ol, (3Z)-13,13-dioctyloxy-3-tridecen-1-ol, (3Z)-13, 13-dinonyloxy-3-tridecen-1-ol, and (3Z)-13,13-didecyloxy-3-tridecen-1-ol;

(3Z)-14,14-dialkoxy-3-tetradecen-1-ol compounds such as (3Z)-14,14-dimethoxy-3-tetradecen-1-ol, (3Z)-14,14-diethoxy-3-tetradecen-1-ol, (3Z)-14,14-dipropoxy-3-tetradecen-1-ol, (3Z)-14,14-dibutoxy-3-tetradecen-1-ol, (3Z)-14,14-dipentyloxy-3-tetradecen-1-ol, (3Z)-14,14-dihexyloxy-3-tetradecen-1-ol, (3Z)-14,14-diheptyloxy-3-tetradecen-1- ol, (3Z)-14,14-dioctyloxy-3-tetradecen-1-ol, (3Z)-14,14-dinonyloxy-3-tetradecen-1-ol, and (3Z)-14,14-didecyloxy-3-tetradecen-1-ol;

(3Z)-15,15-dialkoxy-3-pentadecen-1-ol compounds such as (3Z)-15,15-dimethoxy-3-pentadecen-1-ol, (3Z)-15,15-diethoxy-3-pentadecen-1-ol, (3Z)-15,15-dipropoxy-3-pentadecen-1-ol, (3Z)-15,15-dibutoxy-3-pentadecen-1-ol, (3Z)-15,15-dipentyloxy-3-pentadecen-1-ol, (3Z)-15,15-dihexyloxy-3-pentadecen-1-ol, (3Z)-15,15-diheptyloxy-3-pentadecen-1-ol, (3Z)-15,15-dioctyloxy-3-pentadecen-1-ol, (3Z)-15,15-dinonyloxy-3-pentadecen-1-ol, and (3Z)-15,15-didecyloxy-3-pentadecen-1-ol;

(3Z)-16,16-dialkoxy-3-hexadecen-1-ol compounds such as (3Z)-16,16-dimethoxy-3-hexadecen-1-ol, (3Z)-16,16-diethoxy-3-hexadecen-1-ol, (3Z)-16,16-dipropoxy-3-hexadecen-1-ol, (3Z)-16,16-dibutoxy-3-hexadecen-1-ol, (3Z)-16,16-dipentyloxy-3-hexadecen-1-ol, (3Z)-16,16-dihexyloxy-3-hexadecen-1-ol, (3Z)-16,16-diheptyloxy-3-hexadecen-1-ol, (3Z)-16,16-dioctyloxy-3-hexadecen-1-ol, (3Z)-16,16-dinonyloxy-3-hexadecen-1-ol, and (3Z)-16,16-didecyloxy-3-hexadecen-1-ol;

(3Z)-17,17-dialkoxy-3-heptadecen-1-ol compounds such as (3Z)-17,17-dimethoxy-3-heptadecen-1-ol, (3Z)-17,17-diethoxy-3-heptadecen-1-ol, (3Z)-17,17-dipropoxy-3-heptadecen-1-ol, (3Z)-17,17-dibutoxy-3-heptadecen-1-ol, (3Z)-17,17-dipentyloxy-3-heptadecen-1-ol, (3Z)-17,17-dihexyloxy-3-heptadecen-1-ol, (3Z)-17,17-diheptyloxy-3-heptadecen-1-ol, (3Z)-17,17-dioctyloxy-3-heptadecen-1-ol, (3Z)-17,17-dinonyloxy-3-heptadecen-1-ol, and (3Z)-17,17-didecyloxy-3-heptadecen-1-ol; and (3Z)-18,18-dialkoxy-3-octadecen-1-ol compounds such as (3Z)-18,18-dimethoxy-3-octadecen-1-ol, (3Z)-18,18-diethoxy-3-octadecen-1-ol, (3Z)-18,18-dipropoxy-3-octadecen-1-ol, (3Z)-18,18-dibutoxy-3-octadecen-1-ol, (3Z)-18,18-dipentyloxy-3-octadecen-1-ol, (3Z)-18,18-dihexyloxy-3-octadecen-1-ol, (3Z)-18,18-diheptyloxy-3-octadecen-1-ol, (3Z)-18,18-dioctyloxy-3-octadecen-1-ol, (3Z)-18,18-dinonyloxy-3-octadecen-1-ol, and (3Z)-18,18-didecyloxy-3-octadecen-1-ol.

Preparation of the 1-halodialkoxy-3-alkene
Compound (3) Through Halogenation

The 1-halodialkoxy-3-alkene compound (3) may be prepared by halogenating the dialkoxy-3-alken-1-ol compound (2), as shown in the following chemical reaction formula.

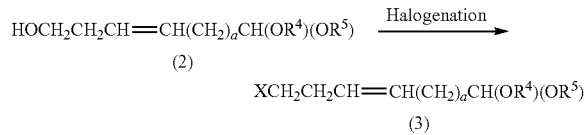

In the halogenation, one or plural species of the dialkoxy-3-alken-1-ol compound (2) may be used, if necessary.

For example, a mixture of a (3E)-12,12-dialkoxy-3-dodecen-1-ol compound (2: a=7) and a (3Z)-12,12-dialkoxy-3-dodecen-1-ol compound (2: a=7) will give a mixture of a (3E)-1-halo-12,12-dialkoxy-3-dodecene compound (3: a=7) and a (3Z)-1-halo-12,12-dialkoxy-3-dodecene compound (3: a=7).

The halogenation reaction may be carried out, for example, by tosylating the hydroxyl group with a p-toluenesulfonyl halide compound, followed by halogenation with a lithium halide compound or by directly halogenating the hydroxyl group with a halogenating agent.

Examples of the halogenating agent include halogen molecules such as chlorine, bromine, and iodine; hydrogen halide compounds such as hydrogen chloride, hydrogen bromide, and hydrogen iodide; methanesulfonyl halide compounds such as methanesulfonyl chloride, methanesulfonyl bromide, and methanesulfonyl iodide; benzenesulfonyl halide compounds such as benzenesulfonyl chloride, benzenesulfonyl bromide, and benzenesulfonyl iodide; p-toluenesulfonyl halide compounds such as p-toluenesulfonyl chloride, p-toluenesulfonyl bromide, and p-toluenesulfonyl iodide; phosphorus halide compounds such as phosphorous trichloride, phosphorous pentachloride, and phosphorus tribromide; carbon tetrahalide compounds such as carbon tetrachloride, carbon tetrabromide, and carbon tetraiodide; alkylsilyl halide compounds such as tetramethylsilyl chloride, tetramethylsilyl bromide, tetramethylsilyl iodide, triethylsilyl chloride, triethylsilyl bromide, triethylsilyl iodide, triisopropylsilyl chloride, triisopropylsilyl bromide, triisopropylsilyl iodide, tert-butyldimethylsilyl chloride, tert-butyldimethylsilyl bromide, and tert-butyldimethylsilyl iodide; oxalyl halide compounds such as oxalyl chloride, oxalyl bromide, and oxalyl iodide; and N-halosuccinimide compounds such as N-chlorosuccinimide, N-bromosuccinimide, and N-iodosuccinimide. A methanesulfonyl halide compound, a benzenesulfonyl halide compound, and a p-toluenesulfonyl halide compound, particularly a methanesulfonyl halide compound, are preferred in view of the suppression of side reactions.

The halogenating agent may be used alone or in combination thereof, if necessary. The halogenating agent may be commercially available one.

An amount of the halogenating agent used is preferably 0.8 to 5.0 mol, more preferably 1.0 to 2.5 mol, per mol of the dialkoxy-3-alken-1-ol compound (2).

A base may be incorporated in the halogenation reaction, if necessary.

Examples of the base include hydroxides such as sodium hydroxide, potassium hydroxide, calcium hydroxide, and magnesium hydroxide; carbonates such as sodium carbonate, potassium carbonate, calcium carbonate, and magnesium carbonate; amines such as triethylamine, N,N-diisopropylethylamine, piperidine, pyrrolidine, pyridine, lutidine, 4-dimethylaminopyridine, N,N-dimethylaniline, N,N-diethylaniline, and 1,8-diazabicyclo[5.4.0]-7-undecene (DBU).

When the halogenating agent is a methanesulfonyl halide compound, a benzenesulfonyl halide compound, or a p-toluenesulfonyl halide compound, the base is preferably an amine, more preferably pyridines such as pyridine, lutidine, or 4-dimethylaminopyridine.

The base may be used alone or in combination thereof, if necessary. The base may be commercially available one.

An amount of the base is preferably 0 to 8.0 mol, more preferably 0 to 3.0 mol, per mol of the dialkoxy-3-alken-1-ol compound (2) in view of the yield and/or economy.

A metal salt may be incorporated in the halogenation reaction, if necessary.

Examples of the metal salt include lithium salts such as lithium chloride, lithium bromide, and lithium iodide; sodium salts such as sodium chloride, sodium bromide, and sodium iodide; potassium salts such as potassium chloride, potassium bromide, and potassium iodide; calcium salts such as calcium chloride, calcium bromide, and calcium iodide; and magnesium salts such as magnesium chloride, magnesium bromide, and magnesium iodide.

The metal salt may be used alone or in combination thereof, if necessary. The metal salt may be commercially available one.

An amount of the metal salt is preferably 0 to 30.0 mol, more preferably 0 to 5.0 mol, per mol of the dialkoxy-3-alken-1-ol compound (2) in view of the reactivity.

Although the metal salt increases a concentration of halide ions in the reaction system to thereby enhance the reactivity, it is preferred, in view of economy and/or environmental protection, not to incorporate the metal salt.

A solvent may be incorporated in the halogenation reaction, if necessary.

Examples of the solvent include usual solvents, for example, ethers such as diethyl ether, dibutyl ether, 4-methyltetrahydropyran, tetrahydrofuran (THF), cyclopentylmethylether, and 1,4-dioxane; hydrocarbons such as hexane, heptane, benzene, toluene, xylene, and cumene; chlorinated solvents such as trichloroethylene, dichloromethane, and chloroform; aprotic polar solvents such as dimethyl sulfoxide, γ-butyrolactone (GBL), N-methylpyrrolidone N,N-dimethylformamide (DMF), N,N-dimethylacetamide (DMAC), and hexamethylphosphoric triamide (HMPA); nitriles such as acetonitrile and propionitrile; and esters such as methyl acetate, ethyl acetate, n-propyl acetate, and n-butyl acetate. 4-Methyltetrahydropyran, dichloromethane, chloroform, γ-butyrolactone, N-methylpyrrolidone, N,N-dimethylformamide, N,N-dimethylacetamide, and acetonitrile are preferred in view of the reactivity. γ-Butyrolactone and acetonitrile are particularly preferred in view of the safety.

The solvent may be used alone or in combination thereof, if necessary. The solvent may be commercially available one.

An amount of the solvent used in the halogenation reaction is preferably 0 to 2,000 g, more preferably 0 to 600 g, per mol of the dialkoxy-3-alken-1-ol compound (2).

The solvent may occupy a part of a reactor space to reduce a space for the starting materials, resulting in a decreased productivity. Therefore, the reaction may be carried out without a solvent or with the base as the solvent.

A reaction temperature in the halogenation varies, depending on a halogenating agent to be used, and is preferably 5 to 180° C. in view of the reactivity.

A reaction time in the halogenation reaction varies, depending on a halogenating agent and/or a reaction scale, and is preferably 1 to 100 hours in view of the reactivity.

The 1-halodialkoxy-3-alkene compound (3) will be explained below.

X in the general formula (3) represents a halogen atom such as a fluorine atom, a chlorine atom, a bromine atom, or iodine atom, $R^4$ and $R^5$ are as defined for the general formula (2), and "a" is as defined for the general formula (1).

Specific examples of the 1-halodialkoxy-3-alkene compound (3) include the following compounds:

(3E)-1-halo-6,6-dimethoxy-3-hexene compounds such as (3E)-1-chloro-6,6-dimethoxy-3-hexene, (3E)-1-bromo-6,6-dimethoxy-3-hexene, and (3E)-1-iodo-6,6-dimethoxy-3-hexene;

(3E)-1-halo-6,6-diethoxy-3-hexene compounds such as (3E)-1-chloro-6,6-diethoxy-3-hexene, (3E)-1-bromo-6,6-diethoxy-3-hexene, and (3E)-1-iodo-6,6-diethoxy-3-hexene;

(3E)-1-halo-7,7-dimethoxy-3-heptene compounds such as (3E)-1-chloro-7,7-dimethoxy-3-heptene, (3E)-1-bromo-7,7-dimethoxy-3-heptene, and (3E)-1-iodo-7,7-dimethoxy-3-heptene;

(3E)-1-halo-7,7-diethoxy-3-heptene compounds such as (3E)-1-chloro-7,7-diethoxy-3-heptene, (3E)-1-bromo-7,7-diethoxy-3-heptene, and (3E)-1-iodo-7,7-diethoxy-3-heptene;

(3E)-1-halo-8,8-dimethoxy-3-octene compounds such as (3E)-1-chloro-8,8-dimethoxy-3-octene, (3E)-1-bromo-8,8-dimethoxy-3-octene, and (3E)-1-iodo-8,8-dimethoxy-3-octene;

(3E)-1-halo-8,8-diethoxy-3-octene compounds such as (3E)-1-chloro-8,8-diethoxy-3-octene, (3E)-1-bromo-8,8-diethoxy-3-octene, and (3E)-1-iodo-8,8-diethoxy-3-octene;

(3E)-1-halo-9,9-dimethoxy-3-nonene compounds such as (3E)-1-chloro-9,9-dimethoxy-3-nonene, (3E)-1-bromo-9,9-dimethoxy-3-nonene, and (3E)-1-iodo-9,9-dimethoxy-3-nonene;

(3E)-1-halo-9,9-diethoxy-3-nonene compounds such as (3E)-1-chloro-9,9-diethoxy-3-nonene, (3E)-1-bromo-9,9-diethoxy-3-nonene, and (3E)-1-iodo-9,9-diethoxy-3-nonene;

(3E)-1-halo-10,10-dimethoxy-3-decene compounds such as (3E)-1-chloro-10,10-dimethoxy-3-decene, (3E)-1-bromo-10,10-dimethoxy-3-decene, and (3E)-1-iodo-10,10-dimethoxy-3-decene;

(3E)-1-halo-10,10-diethoxy-3-decene compounds such as (3E)-1-chloro-10,10-diethoxy-3-decene, (3E)-1-bromo-10,10-diethoxy-3-decene, and (3E)-1-iodo-10,10-diethoxy-3-decene;

(3E)-1-halo-11,11-dimethoxy-3-undecene compounds such as (3E)-1-chloro-11,11-dimethoxy-3-undecene, (3E)-1-bromo-11,11-dimethoxy-3-undecene, and (3E)-1-iodo-11,11-dimethoxy-3-undecene;

(3E)-1-halo-11,11-diethoxy-3-undecene compounds such as (3E)-1-chloro-11,11-diethoxy-3-undecene, (3E)-1-bromo-11,11-diethoxy-3-undecene, and (3E)-1-iodo-11,11-diethoxy-3-undecene;

(3E)-1-halo-12,12-dimethoxy-3-dodecene compounds such as (3E)-1-chloro-12,12-dimethoxy-3-dodecene, (3E)-1-bromo-12,12-dimethoxy-3-dodecene, and (3E)-1-iodo-12,12-dimethoxy-3-dodecene;

(3E)-1-halo-12,12-diethoxy-3-dodecene compounds such as (3E)-1-chloro-12,12-diethoxy-3-dodecene, (3E)-1-bromo-12,12-diethoxy-3-dodecene, and (3E)-1-iodo-12,12-diethoxy-3-dodecene;

(3E)-1-halo-12,12-dipropoxy-3-dodecene compounds such as (3E)-1-chloro-12,12-dipropoxy-3-dodecene, (3E)-1-bromo-12,12-dipropoxy-3-dodecene, and (3E)-1-iodo-12,12-dipropoxy-3-dodecene;

(3E)-1-halo-12,12-dibutoxy-3-dodecene compounds such as (3E)-1-chloro-12,12-dibutoxy-3-dodecene, (3E)-1-bromo-12,12-dibutoxy-3-dodecene, and (3E)-1-iodo-12,12-dibutoxy-3-dodecene;

(3E)-1-halo-12,12-dipentoxy-3-dodecene compounds such as (3E)-1-chloro-12,12-dipentoxy-3-dodecene, (3E)-1-bromo-12,12-dipentoxy-3-dodecene, and (3E)-1-iodo-12,12-dipentoxy-3-dodecene;

(3E)-1-halo-12,12-dihexyloxy-3-dodecene compounds such as (3E)-1-chloro-12,12-dihexyloxy-3-dodecene, (3E)-1-bromo-12,12-dihexyloxy-3-dodecene, and (3E)-1-iodo-12,12-dihexyloxy-3-dodecene;

(3E)-1-halo-12,12-diheptyloxy-3-dodecene compounds such as (3E)-1-chloro-12,12-diheptyloxy-3-dodecene, (3E)-1-bromo-12,12-diheptyloxy-3-dodecene, and (3E)-1-iodo-12,12-diheptyloxy-3-dodecene;

(3E)-1-halo-12,12-dioctyloxy-3-dodecene compounds such as (3E)-1-chloro-12,12-dioctyloxy-3-dodecene, (3E)-1-bromo-12,12-dioctyloxy-3-dodecene, and (3E)-1-iodo-12,12-dioctyloxy-3-dodecene;

(3E)-1-halo-12,12-dinonyloxy-3-dodecene compounds such as (3E)-1-chloro-12,12-dinonyloxy-3-dodecene, (3E)-1-bromo-12,12-dinonyloxy3-dodecene, and (3E)-1-iodo-12,12-dinonyloxy-3-dodecene;

(3E)-1-halo-12,12-didecyloxy-3-dodecene compounds such as (3E)-1-chloro-12,12-didecyloxy-3-dodecene, (3E)-1-bromo-12,12-didecyloxy-3-dodecene, and (3E)-1-iodo-12,12-didecyloxy-3-dodecene;

(3E)-1-halo-13,13-dimethoxy-3-tridecene compounds such as (3E)-1-chloro-13,13-dimethoxy-3-tridecene, (3E)-1-bromo-13,13-dimethoxy-3-tridecene, and (3E)-1-iodo-13,13-dimethoxy-3-tridecene;

(3E)-1-halo-13,13-diethoxy-3-tridecene compounds such as (3E)-1-chloro-13,13-diethoxy-3-tridecene, (3E)-1-bromo-13,13-diethoxy-3-tridecene, and (3E)-1-iodo-13,13-diethoxy-3-tridecene;

(3E)-1-halo-14,14-dimethoxy-3-tetradecene compounds such as (3E)-1-chloro-14,14-dimethoxy-3-tetradecene, (3E)-1-bromo-14,14-dimethoxy-3-tetradecene, and (3E)-1-iodo-14,14-dimethoxy-3-tetradecene;

(3E)-1-halo-14,14-diethoxy-3-tetradecene compounds such as (3E)-1-chloro-14,14-diethoxy-3-tetradecene, (3E)-1-bromo-14,14-diethoxy-3-tetradecene, and (3E)-1-iodo-14,14-diethoxy-3-tetradecene;

(3E)-1-halo-14,14-dipropoxy-3-tetradecene compounds such as (3E)-1-chloro-14,14-dipropoxy-3-tetradecene, (3E)-1-bromo-14,14-dipropoxy-3-tetradecene, and (3E)-1-iodo-14,14-dipropoxy-3-tetradecene;

(3E)-1-halo-14,14-dibutoxy-3-tetradecene compounds such as (3E)-1-chloro-14,14-dibutoxy-3-tetradecene, (3E)-1-bromo-14,14-dibutoxy-3-tetradecene, and (3E)-1-iodo-14,14-dibutoxy-3-tetradecene;

(3E)-1-halo-14,14-dipentoxy-3-tetradecene compounds such as (3E)-1-chloro-14,14-dipentoxy-3-tetradecene, (3E)-1-bromo-14,14-dipentoxy-3-tetradecene, and (3E)-1-iodo-14,14-dipentoxy-3-tetradecene;

(3E)-1-halo-14,14-dihexyloxy-3-tetradecene compounds such as (3E)-1-chloro-14,14-dihexyloxy-3-tetradecene, (3E)-1-bromo-14,14-dihexyloxy-3-tetradecene, and (3E)-1-iodo-14,14-dihexyloxy-3-tetradecene;

(3E)-1-halo-14,14-diheptyloxy-3-tetradecene compounds such as (3E)-1-chloro-14,14-diheptyloxy-3-tetradecene, (3E)-1-bromo-14,14-diheptyloxy-3-tetradecene, and (3E)-1-iodo-14,14-diheptyloxy-3-tetradecene;

(3E)-1-halo-14,14-dioctyloxy-3-tetradecene compounds such as (3E)-1-chloro-14,14-dioctyloxy-3-tetradecene, (3E)-1-bromo-14,14-dioctyloxy-3-tetradecene, and (3E)-1-iodo-14,14-dioctyloxy-3-tetradecene;

(3E)-1-halo-14,14-dinonyloxy-3-tetradecene compounds such as (3E)-1-chloro-14,14-dinonyloxy-3-tetradecene, (3E)-1-bromo-14,14-dinonyloxy-3-tetradecene, and (3E)-1-iodo-14,14-dinonyloxy-3-tetradecene;

(3E)-1-halo-14,14-didecyloxy-3-tetradecene compounds such as (3E)-1-chloro-14,14-didecyloxy-3-tetradecene, (3E)-1-bromo-14,14-didecyloxy-3-tetradecene, and (3E)-1-iodo-14,14-didecyloxy-3-tetradecene;

(3E)-1-halo-15,15-dimethoxy-3-pentadecene compounds such as (3E)-1-chloro-15,15-dimethoxy-3-pentadecene, (3E)-1-bromo-15,15-dimethoxy-3-pentadecene, and (3E)-1-iodo-15,15-dimethoxy-3-pentadecene;

(3E)-1-halo-15,15-diethoxy-3-pentadecene compounds such as (3E)-1-chloro-15,15-diethoxy-3-pentadecene, (3E)-1-bromo-15,15-diethoxy-3-pentadecene, and (3E)-1-iodo-15,15-diethoxy-3-pentadecene;

(3E)-1-halo-16,16-dimethoxy-3-hexadeceene compounds such as (3E)-1-chloro-16,16-dimethoxy-3-hexadecene, (3E)-1-bromo-16,16-dimethoxy-3-hexadecene, and (3E)-1-iodo-16,16-dimethoxy-3-hexadecene;

(3E)-1-halo-16,16-diethoxy-3-hexadeceene compounds such as (3E)-1-chloro-16,16-diethoxy-3-hexadecene, (3E)-1-bromo-16,16-diethoxy-3-hexadecene, and (3E)-1-iodo-16,16-diethoxy-3-hexadecene;

(3E)-1-halo-17,17-dimethoxy-3-heptadecene compounds such as (3E)-1-chloro-17,17-dimethoxy-3-heptadecene, (3E)-1-bromo-17,17-dimethoxy-3-heptadecene, and (3E)-1-iodo-17,17-dimethoxy-3-heptadecene;

(3E)-1-halo-17,17-diethoxy-3-heptadecene compound such as (3E)-1-chloro-17,17-diethoxy-3-heptadecene, (3E)-1-bromo-17,17-diethoxy-3-heptadecene, and (3E)-1-iodo-17,17-diethoxy-3-heptadecene;

(3E)-1-halo-18,18-dimethoxy-3-octadecene compounds such as (3E)-1-chloro-18,18-dimethoxy-3-octadecene, (3E)-1-bromo-18,18-dimethoxy-3-octadecene, and (3E)-1-iodo-18,18-dimethoxy-3-octadecene;

(3E)-1-halo-18,18-diethoxy-3-octadecene compounds such as (3E)-1-chloro-18,18-diethoxy-3-octadecene, (3E)-1-bromo-18,18-diethoxy-3-octadecene, and (3E)-1-iodo-18,18-diethoxy-3-octadecene;

(3Z)-1-halo-6,6-dimethoxy-3-hexene compounds such as (3Z)-1-chloro-6,6-dimethoxy-3-hexene, (3Z)-1-bromo-6,6-dimethoxy-3-hexene, and (3Z)-1-iodo-6,6-dimethoxy-3-hexene;

(3Z)-1-halo-6,6-diethoxy-3-hexene compounds such as (3Z)-1-chloro-6,6-diethoxy-3-hexene, (3Z)-1-bromo-6,6-diethoxy-3-hexene, and (3Z)-1-iodo-6,6-diethoxy-3-hexene;

(3Z)-1-halo-7,7-dimethoxy-3-heptene compounds such as (3Z)-1-chloro-7,7-dimethoxy-3-heptene, (3Z)-1-bromo-7,7-dimethoxy-3-heptene, and (3Z)-1-iodo-7,7-dimethoxy-3-heptene;

(3Z)-1-halo-7,7-diethoxy-3-heptene compounds such as (3Z)-1-chloro-7,7-diethoxy-3-heptene, (3Z)-1-bromo-7,7-diethoxy-3-heptene, and (3Z)-1-iodo-7,7-diethoxy-3-heptene;

(3Z)-1-halo-8,8-dimethoxy-3-octene compounds such as (3Z)-1-chloro-8,8-dimethoxy-3-octene, (3Z)-1-bromo-8,8-dimethoxy-3-octene, and (3Z)-1-iodo-8,8-dimethoxy-3-octene;

(3Z)-1-halo-8,8-diethoxy-3-octene compounds such as (3Z)-1-chloro-8,8-diethoxy-3-octene, (3Z)-1-bromo-8,8-diethoxy-3-octene, and (3Z)-1-iodo-8,8-diethoxy-3-octene;

(3Z)-1-halo-9,9-dimethoxy-3-nonene compounds such as (3Z)-1-chloro-9,9-dimethoxy-3-nonene, (3Z)-1-bromo-9,9-dimethoxy-3-nonene, and (3Z)-1-iodo-9,9-dimethoxy-3-nonene;

(3Z)-1-halo-9,9-diethoxy-3-nonene compounds such as (3Z)-1-chloro-9,9-diethoxy-3-nonene, (3Z)-1-bromo-9,9-diethoxy-3-nonene, and (3Z)-1-iodo-9,9-diethoxy-3-nonene;

(3Z)-1-halo-10,10-dimethoxy-3-decene compounds such as (3Z)-1-chloro-10,10-dimethoxy-3-decene, (3Z)-1-bromo-10,10-dimethoxy-3-decene, and (3Z)-1-iodo-10,10-dimethoxy-3-decene;

(3Z)-1-halo-10,10-diethoxy-3-decene compounds such as (3Z)-1-chloro-10,10-diethoxy-3-decene, (3Z)-1-bromo-10,10-diethoxy-3-decene, and (3Z)-1-iodo-10,10-diethoxy-3-decene;

(3Z)-1-halo-11,11-dimethoxy-3-undecene compounds such as (3Z)-1-chloro-11,11-dimethoxy-3-undecene, (3Z)-1-bromo-11,11-dimethoxy-3-undecene, and (3Z)-1-iodo-11,11-dimethoxy-3-undecene;

(3Z)-1-halo-11,11-diethoxy-3-undecene compounds such as (3Z)-1-chloro-11,11-diethoxy-3-undecene, (3Z)-1-bromo-11,11-diethoxy-3-undecene, and (3Z)-1-iodo-11,11-diethoxy-3-undecene;

(3Z)-1-halo-12,12-dimethoxy-3-dodecene compounds such as (3Z)-1-chloro-12,12-dimethoxy-3-dodecene, (3Z)-1-bromo-12,12-dimethoxy-3-dodecene, and (3Z)-1-iodo-12,12-dimethoxy-3-dodecene;

(3Z)-1-halo-12,12-diethoxy-3-dodecene compounds such as (3Z)-1-chloro-12,12-diethoxy-3-dodecene, (3Z)-1-bromo-12,12-diethoxy-3-dodecene, and (3Z)-1-iodo-12,12-diethoxy-3-dodecene;

(3Z)-1-halo-12,12-dipropoxy-3-dodecene compounds such as (3Z)-1-chloro-12,12-dipropoxy-3-dodecene, (3Z)-1-bromo-12,12-dipropoxy-3-dodecene, and (3Z)-1-iodo-12,12-dipropoxy-3-dodecene;

(3Z)-1-halo-12,12-dibutoxy-3-dodecene compounds such as (3Z)-1-chloro-12,12-dibutoxy-3-dodecene, (3Z)-1-bromo-12,12-dibutoxy-3-dodecene, and (3Z)-1-iodo-12,12-dibutoxy-3-dodecene;

(3Z)-1-halo-12,12-dipentoxy-3-dodecene compounds such as (3Z)-1-chloro-12,12-dipentoxy-3-dodecene, (3Z)-1-bromo-12,12-dipentoxy-3-dodecene, and (3Z)-1-iodo-12,12-dipentoxy-3-dodecene;

(3Z)-1-halo-12,12-dihexyloxy-3-dodecene compounds such as (3Z)-1-chloro-12,12-dihexyloxy-3-dodecene, (3Z)-1-bromo-12,12-dihexyloxy-3-dodecene, and (3Z)-1-iodo-12,12-dihexyloxy-3-dodecene;

(3Z)-1-halo-12,12-diheptyloxy-3-dodecene compounds such as (3Z)-1-chloro-12,12-diheptyloxy-3-dodecene, (3Z)-1-bromo-12,12-diheptyloxy-3-dodecene, and (3Z)-1-iodo-12,12-diheptyloxy-3-dodecene;

(3Z)-1-halo-12,12-dioctyloxy-3-dodecene compounds such as (3Z)-1-chloro-12,12-dioctyloxy-3-dodecene, (3Z)-1-bromo-12,12-dioctyloxy-3-dodecene, and (3Z)-1-iodo-12,12-dioctyloxy-3-dodecene;

(3Z)-1-halo-12,12-dinonyloxy-3-dodecene compounds such as (3Z)-1-chloro-12,12-dinonyloxy-3-dodecene, (3Z)-1-bromo-12,12-dinonyloxy-3-dodecene, and (3Z)-1-iodo-12,12-dinonyloxy-3-dodecene;

(3Z)-1-halo-12,12-didecyloxy-3-dodecene compounds such as (3Z)-1-chloro-12,12-didecyloxy-3-dodecene, (3Z)-1-bromo-12,12-didecyloxy-3-dodecene, and (3Z)-1-iodo-12,12-didecyloxy-3-dodecene;

(3Z)-1-halo-13,13-dimethoxy-3-tridecene compounds such as (3Z)-1-chloro-13,13-dimethoxy-3-tridecene, (3Z)-1-bromo-13,13-dimethoxy-3-tridecene, and (3Z)-1-iodo-13,13-dimethoxy-3-tridecene;

(3Z)-1-halo-13,13-diethoxy-3-tridecene compounds such as (3Z)-1-chloro-13,13-diethoxy-3-tridecene, (3Z)-1-bromo-13,13-diethoxy-3-tridecene, and (3Z)-1-iodo-13,13-diethoxy-3-tridecene;

(3Z)-1-halo-14,14-dimethoxy-3-tetradecene compounds such as (3Z)-1-chloro-14,14-dimethoxy-3-tetradecene, (3Z)-1-bromo-14,14-dimethoxy-3-tetradecene, and (3Z)-1-iodo-14,14-dimethoxy-3-tetradecene;

(3Z)-1-halo-14,14-diethoxy-3-tetradecene compounds such as (3Z)-1-chloro-14,14-diethoxy-3-tetradecene, (3Z)-1-bromo-14,14-diethoxy-3-tetradecene, and (3Z)-1-iodo-14,14-diethoxy-3-tetradecene;

(3Z)-1-halo-14,14-dipropoxy-3-tetradecene compounds such as (3Z)-1-chloro-14,14-dipropoxy-3-tetradecene, (3Z)-1-bromo-14,14-dipropoxy-3-tetradecene, and (3Z)-1-iodo-14,14-dipropoxy-3-tetradecene;

(3Z)-1-halo-14,14-dibutoxy-3-tetradecene compounds such as (3Z)-1-chloro-14,14-dibutoxy-3-tetradecene, (3Z)-1-bromo-14,14-dibutoxy-3-tetradecene, and (3Z)-1-iodo-14,14-dibutoxy-3-tetradecene;

(3Z)-1-halo-14,14-dipentoxy-3-tetradecene compounds such as (3Z)-1-chloro-14,14-dipentoxy-3-tetradecene, (3Z)-1-bromo-14,14-dipentoxy-3-tetradecene, and (3Z)-1-iodo-14,14-dipentoxy-3-tetradecene;

(3Z)-1-halo-14,14-dihexyloxy-3-tetradecene compounds such as (3Z)-1-chloro-14,14-dihexyloxy-3-tetradecene, (3Z)-1-bromo-14,14-dihexyloxy-3-tetradecene, and (3Z)-1-iodo-14,14-dihexyloxy-3-tetradecene;

(3Z)-1-halo-14,14-diheptyloxy-3-tetradecene compounds such as (3Z)-1-chloro-14,14-diheptyloxy-3-tetradecene, (3Z)-1-bromo-14,14-diheptyloxy-3-tetradecene, and (3Z)-1-iodo-14,14-diheptyloxy-3-tetradecene;

(3Z)-1-halo-14,14-dioctyloxy-3-tetradecene compounds such as (3Z)-1-chloro-14,14-dioctyloxy-3-tetradecene, (3Z)-1-bromo-14,14-dioctyloxy-3-tetradecene, and (3Z)-1-iodo-14,14-dioctyloxy-3-tetradecene;

(3Z)-1-halo-14,14-dinonyloxy-3-tetradecene compounds such as (3Z)-1-chloro-14,14-dinonyloxy-3-tetradecene, (3Z)-1-bromo-14,14-dinonyloxy-3-tetradecene, and (3Z)-1-iodo-14,14-dinonyloxy-3-tetradecene;

(3Z)-1-halo-14,14-didecyloxy-3-tetradecene compounds such as (3Z)-1-chloro-14,14-didecyloxy-3-tetradecene, (3Z)-1-bromo-14,14-didecyloxy-3-tetradecene, and (3Z)-1-iodo-14,14-didecyloxy-3-tetradecene;

(3Z)-1-halo-15,15-dimethoxy-3-pentadecene compounds such as (3Z)-1-chloro-15,15-dimethoxy-3-pentadecene, (3Z)-1-bromo-15,15-dimethoxy-3-pentadecene, and (3Z)-1-iodo-15,15-dimethoxy-3-pentadecene;

(3Z)-1-halo-15,15-diethoxy-3-pentadecene compounds such as (3Z)-1-chloro-15,15-diethoxy-3-pentadecene, (3Z)-1-bromo-15,15-diethoxy-3-pentadecene, and (3Z)-1-iodo-15,15-diethoxy-3-pentadecene;

(3Z)-1-halo-16,16-dimethoxy-3-hexadeceene compounds such as (3Z)-1-chloro-16,16-dimethoxy-3-hexadecene, (3Z)-1-bromo-16,16-dimethoxy-3-hexadecene, and (3Z)-1-iodo-16,16-dimethoxy-3-hexadecene;

(3Z)-1-halo-16,16-diethoxy-3-hexadeceene compounds such as (3Z)-1-chloro-16,16-diethoxy-3-hexadecene, (3Z)-1-bromo-16,16-diethoxy-3-hexadecene, and (3Z)-1-iodo-16,16-diethoxy-3-hexadecene;

(3Z)-1-halo-17,17-dimethoxy-3-heptadecene compounds such as (3Z)-1-chloro-17,17-dimethoxy-3-heptadecene, (3Z)-1-bromo-17,17-dimethoxy-3-heptadecene, and (3Z)-1-iodo-17,17-dimethoxy-3-heptadecene;

(3Z)-1-halo-17,17-diethoxy-3-heptadecene compound such as (3Z)-1-chloro-17,17-diethoxy-3-heptadecene, (3Z)-1-bromo-17,17-diethoxy-3-heptadecene, and (3Z)-1-iodo-17,17-diethoxy-3-heptadecene;

(3Z)-1-halo-18,18-dimethoxy-3-octadecene compounds such as (3Z)-1-chloro-18,18-dimethoxy-3-octadecene, (3Z)-1-bromo-18,18-dimethoxy-3-octadecene, and (3Z)-1-iodo-18,18-dimethoxy-3-octadecene; and (3Z)-1-halo-18,18-diethoxy-3-octadecene compounds such as (3Z)-1-chloro-18,18-diethoxy-3-octadecene, (3Z)-1-bromo-18,18-diethoxy-3-octadecene, and (3Z)-1-iodo-18,18-diethoxy-3-octadecene.

Preparation of the dialkoxy-1,3-alkadiene Compound (4) Through Elimination Reaction The dialkoxy-1,3-alkadiene compound (4) may be prepared by eliminating a hydrogen halide, HX, from the 1-halodialkoxy-3-alkene compound (3) in the presence of a base, as shown in the following chemical reaction formula.

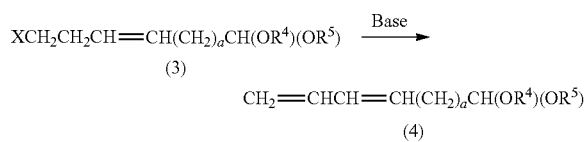

(4)

One or plural species of the 1-halodialkoxy-3-alkene compound (3) may be used in the elimination reaction, if necessary.

Examples of the base used in the elimination reaction for the eliminating group X include hydroxides such as sodium hydroxide, potassium hydroxide, calcium hydroxide, and magnesium hydroxide; metal alkoxides such as sodium methoxide, sodium ethoxide, sodium t-butoxide, sodium t-amyloxide, lithium methoxide, lithium ethoxide, lithium t-butoxide, lithium t-amyloxide, potassium methoxide, potassium ethoxide, potassium t-butoxide, and potassium t-amyloxide; organometallic reagents as methyllithium, ethyllithium, n-butyllithium, methylmagnesium chloride, dimsyl sodium, sodium acetylide, and potassium acetylide; metal amides such as sodium amide, lithium amide, lithium diisopropylamide, lithium hexamethyldisilazide, sodium hexamethyldisilazide, potassium hexamethyldisilazide, and lithium dicyclohexylamide; metal hydride reagents such as sodium hydride, potassium hydride, and calcium hydride; and amines such as triethylamine, N,N-diisopropylethylamine, piperidine, pyrrolidine, pyridine, lutidine, 4-dimethylaminopyridine, N,N-dimethylaniline, N,N-diethylaniline, and 1,8-diazabicyclo[5.4.0]-7-undecene (DBU).

Amines such as DBU; and metal alkoxides such as sodium methoxide, sodium ethoxide, sodium t-butoxide, and potassium t-butoxide are preferred for the suppression of side reactions and a better yield of the dialkoxy-1,3-alkadiene compound (4).

The base may be used alone or in combination thereof, if necessary. The base may be commercially available one.

An amount of the base is preferably 0.8 to 10.0 mol, more preferably 1.0 to 5.0 mol, per mol of the 1-halodialkoxy-3-alkene compound (3) in view of the yield and/or economy.

A solvent may be incorporated in the elimination reaction, if necessary.

Examples of the solvent include usual solvents, for example, ethers such as diethyl ether, dibutyl ether, 4-methyltetrahydropyran, tetrahydrofuran, cyclopentylmethylether, and 1,4-dioxane; hydrocarbons such as hexane, heptane, benzene, toluene, xylene, and cumene; chlorinated solvents such as trichloroethylene, dichloromethane, and chloroform; aprotic polar solvents such as dimethyl sulfoxide, γ-butyrolactone, N-methylpyrrolidone, N,N-dimethylformamide, N,N-dimethylacetamide, and hexamethylphosphoric triamide; nitriles such as acetonitrile and propionitrile; and esters such as methyl acetate, ethyl acetate, n-propyl acetate, and n-butyl acetate. Preferred are ethers such as 4-methyltetrahydropyran and tetrahydrofuran; aprotic polar solvents such as γ-butyrolactone, N-methylpyrrolidone, N,N-dimethylformamide, and N,N-dimethylacetamide; nitriles such as acetonitrile, more preferably tetrahydrofuran, γ-butyrolactone, N-methylpyrrolidone, N,N-dimethylformamide, N,N-dimethylacetamide, and acetonitrile in view of the reactivity.

The solvent may be used alone or in combination thereof, if necessary. The solvent may be commercially available one.

An amount of the solvent used in the deacetylation is preferably 0 to 6,000 g, more preferably 0 to 2,000 g, per mol of the 1-halodialkoxy-3-alkene compound (3).

A reaction temperature in the elimination reaction varies, depending on a base to be used, and is preferably −40 to 140° C., more preferably −20 to 100° C., in view of the reactivity.

A reaction time in the elimination reaction varies, depending on a base to be used and/or a reaction scale, and is preferably 1 to 100 hours in view of the reactivity.

The dialkoxy-1,3-alkadiene compound (4) will be explained below.

$R^4$ and $R^5$ in the dialkoxy-1,3-alkadiene compound (4) are as defined for the general formula (2), and "a" is as defined for the general formula (1).

Specific examples for $R^4$ and $R^5$ being a monovalent hydrocarbon group and a divalent hydrocarbon group are the same as those defined for $R^2$ and $R^3$ being a monovalent hydrocarbon group and a divalent hydrocarbon group, respectively, in the dialkoxyalkenyl alkoxymethyl ether compound (1).

Specific examples of the dialkoxy-1,3-alkadiene compound (4) include the following compounds:

(3E)-6,6-dialkoxy-1,3-hexadiene compounds such as (3E)-6,6-dimethoxy-1,3-hexadiene, (3E)-6,6-diethoxy-1,3-hexadiene, (3E)-6,6-dipropoxy-1,3-hexadiene, (3E)-6,6-dibutoxy-1,3-hexadiene, (3E)-6,6-dipentyloxy-1,3-hexadiene, (3E)-6,6-dihexyloxy-1,3-hexadiene, (3E)-6,6-diheptyloxy-1,3-hexadiene, (3E)-6,6-dioctyloxy-1,3-hexadiene, (3E)-6,6-dinonyloxy-1,3-hexadiene, and (3E)-6,6-didecyloxy-1,3-hexadiene;

(3E)-7,7-dialkoxy-1,3-heptadiene compounds such as (3E)-7,7-dimethoxy-1,3-heptadiene, (3E)-7,7-diethoxy-1,3-heptadiene, (3E)-7,7-dipropoxy-1,3-heptadiene, (3E)-7,7-dibutoxy-1,3-heptadiene, (3E)-7,7-dipentyloxy-1,3-heptadiene, (3E)-7,7-dihexyloxy-1,3-heptadiene, (3E)-7,7-diheptyloxy-1,3-heptadiene, (3E)-7,7-dioctyloxy-1,3-heptadiene, (3E)-7,7-dinonyloxy-1,3-heptadiene, and (3E)-7,7-didecyloxy-1,3-heptadiene;

(3E)-8,8-dialkoxy-1,3-octadiene compounds such as (3E)-8,8-dimethoxy-1,3-octadiene and (3E)-8,8-diethoxy-1,3-octadiene;

(3E)-9,9-dialkoxy-1,3-nonadiene compounds such as (3E)-9,9-dimethoxy-1,3-nonadiene and (3E)-9,9-diethoxy-1,3-nonadiene;

(3E)-10,10-dialkoxy-1,3-decadiene compounds such as (3E)-10,10-dimethoxy-1,3-decadiene and (3E)-10,10-diethoxy-1,3-decadiene;

(3E)-11,11-dialkoxy-1,3-undecadiene compounds such as (3E)-11,11-dimethoxy-1,3-undecadiene and (3E)-11,11-diethoxy-1,3-undecaziene;

(3E)-12,12-dialkoxy-1,3-dodecadiene compounds such as (3E)-12,12-dimethoxy-1,3-dodecadiene, (3E)-12,12-diethoxy-1,3-dodecadiene, (3E)-12,12-dipropoxy-1,3-dodecadiene, (3E)-12,12-dibutoxy-1,3-dodecadiene, (3E)-12,12-dipentyloxy-1,3-dodecadiene, (3E)-12,12-dihexyloxy-1,3-dodecadiene, (3E)-12,12-diheptyloxy-1,3-dodecadiene, (3E)-12,12-dioctyloxy-1,3-dodecadiene, (3E)-12,12-dinonyloxy-1,3-dodecadiene, and (3E)-12,12-didecyloxy-1,3-dodecadiene;

(3E)-13,13-dialkoxy-1,3-tridecadiene compounds such as (3E)-13,13-dimethoxy-1,3-tridecadiene and (3E)-13,13-diethoxy-1,3-tridecadiene;

(3E)-14,14-dialkoxy-1,3-tetradecadiene compounds such as (3E)-14,14-dimethoxy-1,3-tetradecadiene, (3E)-14,14-diethoxy-1,3-tetradecadiene, (3E)-14,14-dipropoxy-1,3-tetradecadiene, (3E)-14,14-dibutoxy-1,3-tetradecadiene, (3E)-14,14-dipentyloxy-1,3-tetradecadiene, (3E)-14,14-dihexyloxy-1,3-tetradecadene, (3E)-14,14-diheptyloxy-1,3-tetradecadiene, (3E)-14,14-dioctyloxy-1,3-tetradecadiene, (3E)-14,14-dinonyloxy-1,3-tetradecadiene, and (3E)-14,14-didecyloxy-1,3-tetradecadiene;

(3E)-15,15-dialkoxy-1,3-pentadecadiene compounds such as (3E)-15,15-dimethoxy-1,3-pentadecaziene and (3E)-15,15-diethoxy-1,3-pentadecadiene;

(3E)-16,16-dialkoxy-1,3-hexadecadiene compounds such as (3E)-16,16-dimethoxy-1,3-hexadecadiene and (3E)-16,16-diethoxy-1,3-hexadecadiene;

(3E)-17,17-dialkoxy-1,3-heptadecadiene compounds such as (3E)-17,17-dimethoxy-1,3-heptadecadiene and (3E)-17,17-diethoxy-1,3-heptadecadiene;

(3E)-18,18-dialkoxy-1,3-octadecadiene compounds such as (3E)-18,18-dimethoxy-1,3-octadecadiene and (3E)-18,18-diethoxy-1,3-octadecadiene;

(3Z)-6,6-dialkoxy-1,3-hexadiene compounds such as (3Z)-6,6-dimethoxy-1,3-hexadiene and (3Z)-6,6-diethoxy-1,3-hexadiene, (3Z)-6,6-dipropoxy-1,3-hexadiene, (3Z)-6,6-dibutoxy-1,3-hexadiene, (3Z)-6,6-dipentyloxy-1,3-hexadiene, (3Z)-6,6-dihexyloxy-1,3-hexadiene, (3Z)-6,6-diheptyloxy-1,3-hexadiene, (3Z)-6,6-dioctyloxy-1,3-hexadiene, (3Z)-6,6-dinonyloxy-1,3-hexadiene, and (3Z)-6,6-didecyloxy-1,3-hexadiene;

(3Z)-7,7-dialkoxy-1,3-heptadiene compounds such as (3Z)-7,7-dimethoxy-1,3-heptadiene, (3Z)-7,7-diethoxy-1,3-heptadiene, (3Z)-7,7-dipropoxy-1,3-heptadiene, (3Z)-7,7-dibutoxy-1,3-heptadiene, (3Z)-7,7-dipentyloxy-1,3-heptadiene, (3Z)-7,7-dihexyloxy-1,3-heptadiene, (3Z)-7,7-diheptyloxy-1,3-heptadiene, (3Z)-7,7-dioctyloxy-1,3-heptadiene, (3Z)-7,7-dinonyloxy-1,3-heptadiene, and (3Z)-7,7-didecyloxy-1,3-heptadiene;

(3Z)-8,8-dialkoxy-1,3-octadiene compounds such as (3Z)-8,8-dimethoxy-1,3-octadiene and (3Z)-8,8-diethoxy-1,3-octadiene;

(3Z)-9,9-dialkoxy-1,3-nonadiene compounds such as (3Z)-9,9-dimethoxy-1,3-nonadiene and (3Z)-9,9-diethoxy-1,3-nonadiene;

(3Z)-10,10-dialkoxy-1,3-decadiene compounds such as (3Z)-10,10-dimethoxy-1,3-decadiene and (3Z)-10,10-diethoxy-1,3-decadiene;

(3Z)-11,11-dialkoxy-1,3-undecadiene compounds such as (3Z)-11,11-dimethoxy-1,3-undecadiene and (3Z)-11,11-diethoxy-1,3-undecaziene;

(3Z)-12,12-dialkoxy-1,3-dodecadiene compounds such as (3Z)-12,12-dimethoxy-1,3-dodecadiene, (3Z)-12,12-diethoxy-1,3-dodecadiene, (3Z)-12,12-dipropoxy-1,3-dodecadiene, (3Z)-12,12-dibutoxy-1,3-dodecadiene, (3Z)-12,12-dipentyloxy-1,3-dodecadiene, (3Z)-12,12-dihexyloxy-1,3-dodecadiene, (3Z)-12,12-diheptyloxy-1,3-dodecadiene, (3Z)-12,12-dioctyloxy-1,3-dodecadiene, (3Z)-12,12-dinonyloxy-1,3-dodecadiene, and (3Z)-12,12-didecyloxy-1,3-dodecadiene;

(3Z)-13,13-dialkoxy-1,3-tridecadiene compounds such as (3Z)-13,13-dimethoxy-1,3-tridecadiene and (3Z)-13,13-diethoxy-1,3-tridecadiene;

(3Z)-14,14-dialkoxy-1,3-tetradecadiene compounds such as (3Z)-14,14-dimethoxy-1,3-tetradecadiene, (3Z)-14,14-diethoxy-1,3-tetradecadiene, (3Z)-14,14-dipropoxy-1,3-tetradecadiene, (3Z)-14,14-dibutoxy-1,3-tetradecadiene, (3Z)-14,14-dipentyloxy-1,3-tetradecadiene, (3Z)-14,14-dihexyloxy-1,3-tetradecadene, (3Z)-14,14-diheptyloxy-1,3-tetradecadiene, (3Z)-14,14-dioctyloxy-1,3-tetradecadiene, (3Z)-14,14-dinonyloxy-1,3-tetradecadiene, and (3Z)-14,14-didecyloxy-1,3-tetradecadiene;

(3Z)-15,15-dialkoxy-1,3-pentadecadiene compounds such as (3Z)-15,15-dimethoxy-1,3-pentadecaziene and (3Z)-15,15-diethoxy-1,3-pentadecadiene;

(3Z)-16,16-dialkoxy-1,3-hexadecadiene compounds such as (3Z)-16,16-dimethoxy-1,3-hexadecadiene and (3Z)-16,16-diethoxy-1,3-hexadecadiene;

(3Z)-17,17-dialkoxy-1,3-heptadecadiene compounds such as (3Z)-17,17-dimethoxy-1,3-heptadecadiene and (3Z)-17,17-diethoxy-1,3-heptadecadiene; and (3Z)-18,18-dialkoxy-1,3-octadecadiene compounds such as (3Z)-18,18-dimethoxy-1,3-octadecadiene and (3Z)-18,18-diethoxy-1,3-octadecadiene.

Preparation of the Terminal Conjugated Alkadienal Compound (5) Through Hydrolysis The terminal conjugated alkadienal compound (5) may be prepared by hydrolyzing the dialkoxy-1,3-alkadiene compound (4), as shown in the following chemical reaction formula.

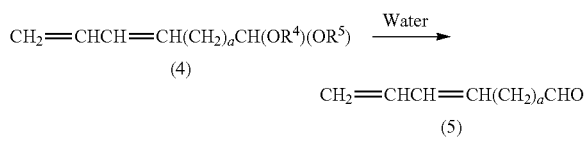

One or plural species of the dialkoxy-1,3-alkadiene compound (4) may be used in the hydrolysis reaction, if necessary.

For example, a mixture of a (3E)-12,12-dialkoxy-1,3-dodecadiene compound (4: a=7) and a (3Z)-12,12-dialkoxy-1,3-dodecadiene compound (4: a=7) will give a mixture of (9E)-9,11-dodecadienal (5: a=7), i.e., sex pheromon of *Setothosea asigna*, and (9Z)-9,11-dodecadienal (5: a=7), i.e., sex pheromon of *Setora nitens*.

Each of the E-form and the Z-foam may be synthesized independently, or a mixture of them may be synthesized as stated above. When a complex active agent for communication disruption effective for both *Setothosea asigna* and *Setora nitens* is desired, the E- and Z-forms may be prepared separately and mixed, or—a mixture of E- and Z-forms may be prepared at once.

The hydrolysis may be carried out, typically, in acidic conditions.

Examples of an acid to provide acidic conditions include inorganic acids such as hydrochloric acid and hydrobromic acid; p-toluenesulfonic acid, benzenesulfonic acid, trifluoroacetic acid, acetic acid, formic acid, oxalic acid, iodotrimethylsilane, and titanium tetrachloride, with acetic acid, formic acid, and oxalic acid being preferred in view of the reactivity.

The acid may be used either alone or in combination thereof. The acids may be commercially available one.

An amount of the acid used is preferably 0.01 to 10.0 mol per mol of the dialkoxy-1,3-alkadiene compound (4).

An amount of water used in the hydrolysis is preferably from 18 to 3,000 g per mol of the dialkoxy-1,3-alkadiene compound (4) in view of reactivity.

A solvent may be incorporated in the hydrolysis, if necessary, in addition to the aforesaid acid and water.

Examples of the solvent include hydrocarbons such as hexane, heptane, toluene, xylene, benzene, and cumene; ethers such as diethyl ether, dibutyl ether, 4-methyltetrahydropyran, tetrahydrofuran, cyclopentylmethylether, and 1,4-dioxane; aprotic polar solvents such as dimethyl sulfoxide, N,N-dimethylformamide, N,N-dimethylacetamide, N-methylpyrrolidone, acetonitrile, acetone, γ-butyrolactone, dichloromethane, and chloroform; and alcohols such as methanol and ethanol.

The solvent may be used either alone or in combination thereof. The solvent may be commercially available one.

An optimum solvent varies, depending on an acid used. For instance, when oxalic acid is used, tetrahydrofuran, acetone and γ-butyrolactone are preferred in view of the reactivity.

An amount of the solvent is preferably from 0 to 3000 g per mol of the dialkoxy-1,3-alkadiene compound (4) in view of the reactivity.

A reaction temperature in the hydrolysis varies, depending on an acid and/or solvent used, and is preferably from 5 to 180° C. in view of the reactivity.

A reaction time in the hydrolysis varies, depending on a solvent used and/or a production scale, and is preferably from 1 to 100 hours in view of the reactivity.

Usually, the 1-halodialkoxy-3-alkene compound (3) is subjected to the elimination reaction in the presence of a base, and water is added, followed by phase separation, concentration and purification. However, the 1-halodialkoxy-3-alkene compound (3) may be subjected directly to the hydrolysis reaction without concentration and purification. Then, the solvent used in the elimination reaction is utilized also in the hydrolysis reaction. Therefore, waste is reduced, and/or energy and/or time for concentration and purification are reduced, which make the process industrially advantageous.

The terminal conjugated alkadienal compound (5) will be explained below.

"a" in the general formula (5) is as defined for the general formula (1).

Specific examples of the terminal conjugated alkadienal compound (5) include 4,6-hexadienal compounds such as (4E)-4,6-hexadienal and (4Z)-4,6-hexadienal; 5,8-octadienal compounds such as (5E)-5,8-octadienal and (5Z)-5,8-octadienal; 6,8-nonadienal compounds such as (6E)-6,8-nonadienal and (6Z)-6,8-nonadienal; 7,9-decadienal compounds such as (7E)-7,9-decadienal and (7Z)-7,9-decadienal; 8,10-undecadienal compounds such as (8E)-8,10-undecadienal and (8Z)-8,10-undecadienal; 9,11-dodecadienal compounds such as (9E)-9,11-dodecadienal and (9Z)-9,11-dodecadienal; 10,12-tridecadienal compounds such as (10E)-10,12-tridecadienal and (10Z)-10,12-tridecadienal; 11,13-tetradecadienal compounds such as (11E)-11,13-tetradecadienal and (11Z)-11,13-tetradecadienal; 12,14-pentadecadienal compounds such as (12E)-12,14-pentadecazienal and (12Z)-12,14-pentadecadienal; 13,15-hexadecadienal compounds such as (13E)-13,15-hexadecadienal and (13Z)-13,15-hexadecadienal; 14,16-heptadecadienal compounds such as (14E)-14,16-heptadecadienal and (14Z)-14,16-heptadecadienal; and 15,17-octadecadienal compounds such as (15E)-15,17-octadecadienal and (15Z)-15,17-octadecadienal.

EXAMPLES

The present invention will be explained with reference to the following Examples. It should be noted that the present invention is not limited to or by the Examples.

The term "purity" as used herein means an area percentage in gas chromatography (GC), unless otherwise specified. The term "production ratio" means a ratio of area percentages in GC. The term "yield" is calculated from the area percentages determined by GC.

In the Examples, monitoring of the reactions and calculation of the yields were carried out in the following GC conditions.

GC conditions: GC: Capillary gas chromatograph GC-2014 (Shimadzu Corporation); column: DB-WAX (sp-2331), 0.25 μm×0.25 mmφ×30 m; carrier gas: He (1.55 mL/min), detector: FID; column temperature: 150° C., elevated in a rate of 5° C./min, and up to 230° C.

The yield was calculated according to the following equation in consideration of purities (% GC) of a starting material and a product.

Yield (%)={[(weight of a product obtained by a reaction×% GC)/molecular weight of a product]÷[(weight of a starting material in a reaction×% GC)/molecular weight of a starting material]}×100

GBL represents γ-butyrolactone, THF represents tetrahydrofuran, Ph represents a phenyl group, and $^t$Bu represents tert-butyl group.

Example 1

Preparation of (3E)-12,12-diethoxy-3-dodecenyl methoxymethyl ether (1: R$^1$=H, R$^2$=R$^3$=CH$_2$CH$_3$; a=7)

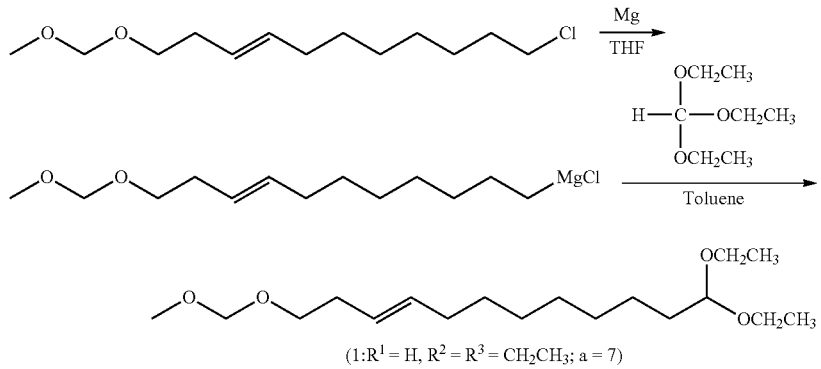

Magnesium (77.34 g, 3.18 mol) and tetrahydrofuran (909.30 g) were placed in a reactor at room temperature and stirred at 60 to 65° C. for 21 minutes. After the completion of the stirring, (3E)-11-chloro-3-undecenyl methoxymethyl ether (782.04 g, 3.031 mol, purity 96.41%; 3Z: 3E=92.7:

7.3) was added dropwise at 60 to 75° C. After the completion of the dropwise addition, the reaction mixture was stirred at 75 to 80° C. for 2 hours.

Subsequently, toluene (1409.42 g) and ethyl orthoformate (583.95 g, 3.94 mol) were added dropwise at 75 to 85° C. After the completion of the dropwise addition, the reaction mixture was stirred at 90 to 100° C. for 16 hours. After the completion of the stirring, the reaction mixture was cooled to 30 to 45° C., and an aqueous acetic acid solution (acetic acid, 378.88 g and water, 1136.63 g) was added to the reaction mixture, followed by phase separation. The aqueous phase was removed to obtain the organic phase. The organic phase thus obtained was concentrated at a reduced pressure, and the concentrate was subjected to distillation at a reduced pressure to obtain (3E)-12,12-diethoxy-3-dodecenyl methoxymethyl ether (1: $R^1$=H, $R^2$=$R^3$=$CH_2CH_3$; a=7) (887.38 g, 2.67 mol, purity 95.21%; 3Z: 3E=92.6: 7.4, bp=159.2 to 167.8° C./0.40 kPa (3. 0 mmHg)) in a yield of 88.10%.

The following is the spectrum data of the (3E)-12,12-diethoxy-3-dodecenyl methoxymethyl ether (1: $R^1$=H, $R^2$=$R^3$=$CH_2CH_3$; a=7) thus prepared.

[Nuclear magnetic resonance spectrum]: $^1$H-NMR (500 MHz, CDCl$_3$): δ=1.19 (6H, t, J=6.9 Hz), 1.23-1.38 (10H, m), 1.59 (2H, dt, J=9.2 Hz, 6.1 Hz), 1.97 (2H, q-like, J=6.6 Hz), 2.28 (2H, ddt, J=1.1 Hz, 6.7 Hz, 6.7 Hz), 3.35 (3H, s), 3.47 (1H, q, J=7.3 Hz,), 3.49 (1H, q, J=7.3 Hz), 3.53 (2H, t, J=6.9 Hz), 3.61 (1H, q, J=7.3 Hz), 3.63 (1H, q, J=7.3 Hz), 4.46 (1H, t, J=5.7 Hz), 4.61 (2H, s), 5.35-5.43 (1H, m), 5.46-5.54 (1H, m); $^{13}$C-NMR (500 MHz, CDCl$_3$): δ=15.33, 24.72, 29.04, 29.38, 29.41, 32.59, 33.03, 33.56, 55.09, 60.78, 67.65, 96.32, 102.93, 126.10, 132.72.

[Mass spectrum]: EI-mass spectrum (70 eV): m/z 315 (M$^+$-1), 271, 239, 208, 181, 103, 75, 45, 29.

[Infrared absorption spectrum] (D-ATR): vmax=2926, 2855, 1443, 1374, 1150, 1112, 1062, 968, 919.

Example 2

Preparation of (3Z)-12,12-diethoxy-3-dodecenyl methoxymethyl ether (1: $R^1$=H, $R^2$=$R^3$=$CH_2CH_3$; a=7)

Magnesium (81.65 g, 3.36 mol) and tetrahydrofuran (960.00 g) were placed in a reactor at room temperature and stirred at 60 to 65° C. for 11 minutes. After the completion of the stirring, the (3Z)-11-chloro-3-undecenylmethoxymethyl ether (840.24 g, 3.20 mol, purity 94.75%; 3Z: 3E=96.2: 3.8) was added dropwise at 60 to 75° C. After the completion of the dropwise addition, the reaction mixture was stirred at 75 to 80° C. for 3 hours.

Subsequently, toluene (1488.00 g) and ethyl orthoformate (616.51 g, 4.16 mol) were added dropwise at 75 to 85° C. After the completion of the dropwise addition, the reaction mixture was stirred at 90 to 100° C. for 15.5 hours. After the completion of the stirring, the reaction mixture was cooled to 30 to 45° C., and an aqueous acetic acid solution (acetic acid, 400.00 g and water, 1200.00 g) were added to the reaction mixture, followed by phase separation. The aqueous phase was removed to obtain the organic phase. The organic phase thus obtained was concentrated at a reduced pressure, and the concentrate was subjected to distillation at a reduced pressure to obtain (3Z)-12,12-diethoxy-3-dodecenyl methoxymethyl ether (1: $R^1$=H, $R^2$=$R^3$=$CH_2CH_3$; a=7) (907.41 g, 2.71 mol, purity 92.59%; 3Z: 3E=95.7: 4.3, bp=160.0 to 167.1° C./0.40 kPa (3. 0 mmHg)) in a yield of 84.56%.

The following is the spectrum data of the (3Z)-12,12-diethoxy-3-dodecenyl methoxymethyl ether (1: $R^1$=H, $R^2$=$R^3$=$CH_2CH_3$; a=7) thus prepared.

[Nuclear magnetic resonance spectrum]: $^1$H-NMR (500 MHz, CDCl$_3$): δ=1.19 (6H, t, J=6.9 Hz), 1.24-1.38 (12H, m), 1.55-1.62 (2H, m), 2.03 (2H, dt, J=6.9 Hz, 6.9 Hz), 2.33 (2H, dt, J=6.9 Hz, 6.9 Hz), 3.35 (3H, s), 3.46 (1H, q, J=6.9 Hz), 3.48 (1H, q, J=6.9 Hz), 3.52 (2H, t, J=6.9 Hz), 3.61 (1H, q, J=6.9 Hz), 3.63 (1H, q, J=6.9 Hz), 4.46 (1H, t, J=5.7 Hz), 4.61 (2H, s), 5.33-5.40 (1H, m), 5.42-5.50 (1H, m); $^{13}$C-NMR (500 MHz, CDCl$_3$): δ=15.32, 24.70, 27.29, 27.86, 29.16, 29.40, 29.54, 33.55, 55.07, 60.76, 67.38, 96.30, 102.91, 125.36, 132.11.

[Mass spectrum]: EI-mass spectrum (70 eV): m/z 315 (M$^+$-1), 271, 175, 103, 75, 45.

[Infrared absorption spectrum] (D-ATR): vmax=2927, 2856, 1443, 1375, 1150. 1111, 1062, 1037, 920, 724.

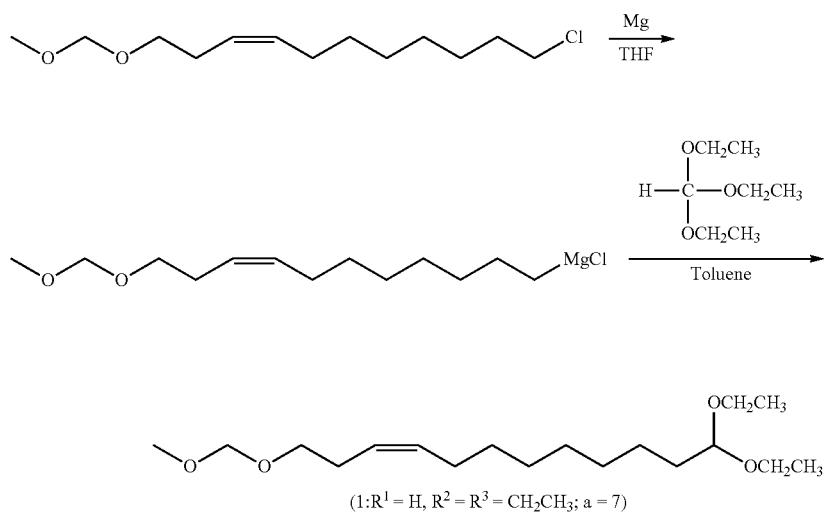

(1: $R^1$ = H, $R^2$ = $R^3$ = $CH_2CH_3$; a = 7)

Example 3

Preparation of (3Z)-12,12-dimethoxy-3-dodecenyl butoxymethyl ether (1: $R^1$=CH$_3$(CH$_2$)$_2$, $R^2$=$R^3$=CH$_3$; a=7)

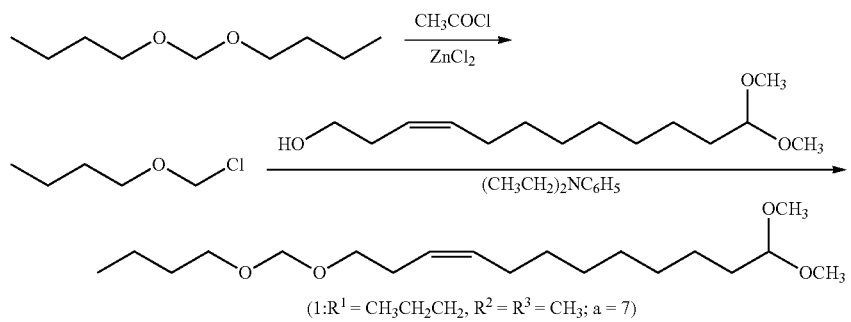

(1:$R^1$ = CH$_3$CH$_2$CH$_2$, $R^2$ = $R^3$ = CH$_3$; a = 7)

Zinc chloride (0.042 g, 0.31 mmol) and dibutoxymethane (8.32 g, 0.052 mol) were placed in a reactor at room temperature and stirred at 15 to 25° C. for 7 minutes. After the completion of the stirring, acetyl chloride (3.63 g, 0.046 mol) was added dropwise at 20 to 35° C. After the completion of the dropwise addition, the reaction mixture was stirred at 35 to 40° C. for 2 hours to obtain chloromethyl butyl ether.

Subsequently, a mixture solution of (3Z)-12,12-dimethoxy-3-dodecen-1-ol (2: $R^4$=$R^5$=CH$_3$; a=7) (8.00 g, 0.031 mol, purity 94.15%; 3Z: 3E=96.1: 3.9) and N,N-diethylaniline (6.91 g, 0.046 mol) were added dropwise at 20 to 30° C. and stirred at 20 to 30° C. for 25 hours. After the completion of the stirring, an aqueous 25% by mass sodium hydroxide solution (15.00 g, 0.094 mol as sodium hydroxide) and subsequently water (15.00 g) was added to the reaction mixture, followed by phase separation. The aqueous phase was removed to obtain the organic phase. The organic phase thus obtained was concentrated at a reduced pressure, and the concentrate was subjected to distillation at a reduced pressure to obtain (3Z)-12,12-dimethoxy-3-dodecenyl butoxymethyl ether (1: $R^1$=CH$_3$(CH$_2$)$_2$, $R^2$=$R^3$=CH$_3$; a=7) (11.55 g, 0.031 mol, purity 88.68%; 3Z: 3E=96.0: 4.0) in a yield of 100%.

The following is the spectrum data of the (3Z)-12,12-dimethoxy-3-dodecenyl butoxymethyl ether (1: $R^1$=CH$_3$(CH$_2$)$_2$, $R^2$=$R^3$=CH$_3$; a=7) thus prepared.

[Nuclear magnetic resonance spectrum]: $^1$H-NMR (500 MHz, CDCl$_3$): δ=0.92 (3H, t, J=7.3 Hz), 1.23-1.42 (12H, m), 1.52-1.60 (4H, m), 2.03 (2H, q-like, J=6.9 Hz), 2.32 (2H, q -like, J=6.9 Hz), 3.30 (6H, s), 3.52 (4H, t, J=6.7 Hz), 4.34 (1H, t, J=5.7 Hz), 4.66 (2H, s), 5.36 (1H, dtt, J=11.1 Hz, 6.9 Hz, 1.5 Hz), 5.45 (1H, d tt, J=10.7 Hz, 7.3 Hz, 1.5 Hz); $^{13}$C-NMR (500 MHz, CDCl$_3$): δ=13.84, 19.34, 24.56, 27.29, 27.87, 29.16, 29.40, 29.56, 31.78, 32.45, 52.52, 67.33, 67.52, 95.15, 104.51, 125.43, 132.06.

[Mass spectrum]: EZ-mass spectrum (70 eV): m/z 329 (M$^+$-1), 299, 267, 241, 225, 194, 175, 149, 121, 95, 75, 57.

[Infrared absorption spectrum] (D-ATR): νmax=2928, 2857, 1465, 1383, 1118, 1075, 1041, 954, 827, 724.

Example 4

Preparation of (3Z)-12,12-dimethoxy-3-dodecenyl benzyloxymethyl ether (1: $R^1$=Ph, $R^2$=$R^3$=CH$_3$; a=7)

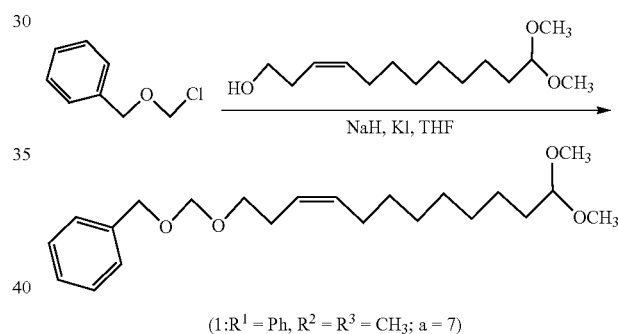

(1:$R^1$ = Ph, $R^2$ = $R^3$ = CH$_3$; a = 7)

Sodium hydride (1.48 g, 0.034 mmol, purity 55%), potassium iodide (0.051 g, 0.31 mmol) and tetrahydrofuran (40.00 g) were placed in a reactor at room temperature and stirred at 0 to 25° C. for 25 minutes. After the completion of the stirring, (3Z)-12,12-dimethoxy-3-dodecen-1-ol (2: $R^4$=$R^5$=CH$_3$; a=7) (8.00 g, 0.031 mol, purity 94. 15%; 3Z: 3E=96.1: 3.9) was added dropwise at 0 to 10° C. After the completion of the dropwise addition, the reaction mixture was stirred at 0 to 10° C. for 1 hours.

Subsequently, benzyl chloromethyl ether (5.36 g, 0.034 mol) was added at 0 to 10° C. and stirred at 45 to 55° C. for 4 hours. After the completion of the stirring, an aqueous solution of ammonium chloride (ammonium chloride, 0.21 g; sodium chloride, 0.94 g; and water, 29.52 g) was added to the reaction mixture, followed by phase separation. The aqueous phase was removed to obtain the organic phase. The organic phase thus obtained was concentrated at a reduced pressure, and the concentrate was subjected to distillation at a reduced pressure to obtain (3Z)-12,12-dimethoxy-3-dodecenyl benzyloxymethyl ether (1: $R^1$=Ph, $R^2$=$R^3$=CH$_3$; a=7) (3.21 g, 0. 0073 mol, purity 82.80%) in a yield of 23.66%.

The following is the spectrum data of the (3Z)-12,12-dimethoxy-3-dodecenyl benzyloxymethyl ether (1: $R^1$=Ph, $R^2$=$R^3$=CH$_3$; a=7) thus prepared.

[Nuclear magnetic resonance spectrum]: $^1$H-NMR (500 MHz, CDCl$_3$): δ=1.24-1.40 (10E, m), 1.59 (2H, q-like, J=7.0 Hz), 2.04 (2H, dt, J=6.9 Hz, 6.9 Hz), 2.35 (2H, dt, J=7.3 Hz, 7.3 Hz), 3.31 (6H, s), 3.60 (2H, t, J=7.1 Hz), 4.35 (1H, t, J=5.7 Hz), 4.61 (2H, s), 4.76 (2H, s), 5.39 (1H, dtt, J=10.7 Hz, 7.3 Hz, 1.5 Hz), 5.48 (1H, dtt, J=10.7 Hz, 7.3 Hz, 1.5 Hz), 7.27-7.37 (5H, m); $^{13}$C-NMR (500 MHz, CDCl$_3$): δ=24.56, 27.31, 27.85, 29.17, 29.41, 29.56, 32.46, 52.54, 67.59, 69.25, 94.50, 104.53, 125.40, 127.62, 127.86, 128.36, 132.15, 137.93.

[Mass spectrum]: EI-mass spectrum (70 eV): m/z 287 (M$^+$−77), 243, 225, 194, 175, 149, 121, 91, 75, 41.

[Infrared absorption spectrum] (D-ATR): vmax=2927, 2855, 1455, 1383, 1121, 1052, 955, 735, 698.

Example 5

Preparation of (3Z)-7,7-diethoxy-3-heptenyl methoxymethyl ether (1: R$^1$=H, R$^2$=R$^3$=CH$_2$CH$_3$; a=2)

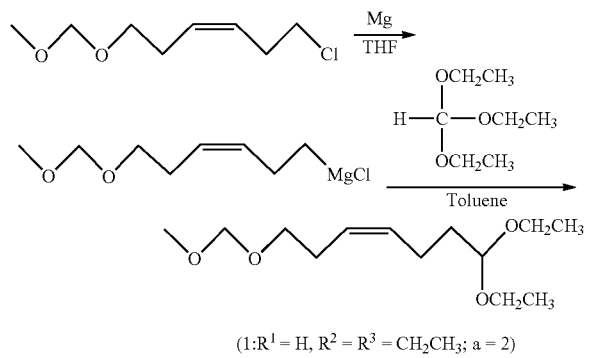

Magnesium (9.83 g, 0.42 mol) and tetrahydrofuran (120.00 g) were placed in a reactor at room temperature and stirred at 60 to 65° C. for 23 minutes. After the completion of the stirring, (3Z)-6-chloro-3-hexenylmethoxymethyl ether (73.66 g, 0.40 mol, purity 97.02%) was added dropwise at 60 to 75° C. After the completion of the dropwise addition, the reaction mixture was stirred at 75 to 80° C. for 3 hours.

Subsequently, toluene (186.00 g) and ethyl orthoformate (77.06 g, 0.52 mol) were added dropwise at 75 to 85° C. After the completion of the dropwise addition, the reaction mixture was stirred at 90 to 100° C. for 11 hours. After the completion of the stirring, the reaction mixture was cooled to 30 to 45° C., and an aqueous acetic acid solution (acetic acid, 400.00 g, and water, 1200.00 g) was added to the reaction mixture, followed by phase separation. The aqueous phase was removed to obtain the organic phase. The organic phase thus obtained was concentrated at a reduced pressure, and the concentrate was subjected to distillation at a reduced pressure to obtain (3Z)-7,7-diethoxy-3-heptenyl methoxymethyl ether (1: R$^1$=H, R$^2$=R$^3$=CH$_2$CH$_3$; a=2) (83.39 g, 0.29 mol, purity 85.52%; 3Z: 3E=90.6: 9.4, bp=112.0 to 126.9° C./0.40 kPa (3. 0 mmHg)) in a yield of 72.37%.

The following is the spectrum data of the (3Z)-7,7-diethoxy-3-heptenyl methoxymethyl ether (1: R$^1$=H, R$^2$=R$^3$=CH$_2$CH$_3$; a=2) thus prepared.

[Nuclear magnetic resonance spectrum]: $^1$H-NMR (500 MHz, CDCl$_3$): δ=1.19 (6H, t, J=7.0 Hz), 1.63-1.68 (2H, m), 2.11 (2H, dt, J=7.4 Hz, 7.4 Hz), 2.34 (2H, dt, J=6.9 Hz, 6.9 Hz), 3.34 (3H, s), 3.46 (1H, q, J=7.0 Hz), 3 48 (1H, q, J=7.0 Hz), 3.52 (2H, t, J=6.9 Hz), 3.61 (1H, q, J=7.0 Hz), 3.63 (1H, q, J=7.0 Hz), 4.47 (1H, t, J=5.7 Hz), 4.60 (2H, s), 5.36-5.50 (2H, m); $^{13}$C-NMR (500 MHz, CDCl$_3$): δ=15.31, 22.67, 27.79, 33.33, 55.06, 60.92, 67.26, 96.29, 102.28, 126.14, 130.94.

[Mass spectrum]: EI-mass spectrum (70 eV): m/z 245 (M$^+$−1), 231, 217, 201, 185, 169, 155, 103, 75, 45.

[Infrared absorption spectrum] (D-ATR): vmax=2975, 2930, 2881, 1444, 1374, 1111, 1062, 1038, 969, 920, 731.

Example 6

Preparation of (3E)-12,12-dimethoxy-3-dodecen-1-ol (2: R$^4$=R$^5$=CH$_3$; a=7)

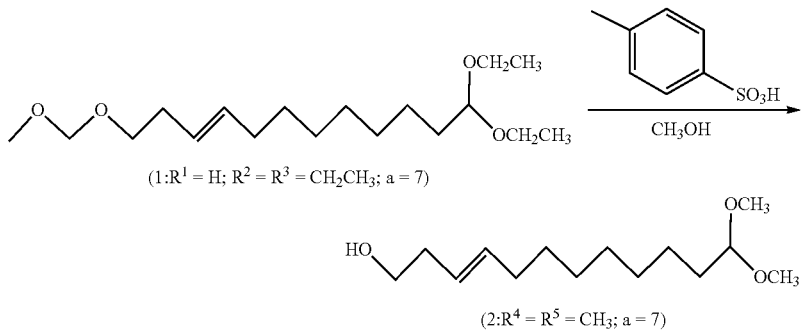

(3E)-12,12-Diethoxy-3-dodecenyl methoxymethyl ether (1: R$^1$=H, R$^2$=R$^3$=CH$_2$CH$_3$; a=7) (81.66 g, 0.24 mol, purity 84.11%; 3Z: 3E=0: 100) obtained as in Example 1, methanol (238.20 g, 7.43 mol) and p-toluenesulfonic acid monohydrate (0.46 g, 0.0024 mol) were placed in a reactor equipped with a distillation column, and the reaction mixture was heated to 60° C. and stirred for 4.5 hours. After the completion of the stirring, the internal temperature was raised to 65 to 70° C., and a mixture of dimethoxymethane by-produced and methanol was distilled off from the distillation column. The reaction mixture was sampled during the reaction. When it was found that the conversion ratio reached 100%, an aqueous 25% by mass sodium hydroxide solution (3.82 g, 0.024 mol as sodium hydroxide) was added, and methanol was removed until no distillate emerged. Then, water (80 g) was added, followed by phase separation. The aqueous phase was removed to obtain the organic phase. The organic phase thus obtained was concentrated at a reduced pressure, and the concentrate was subjected to distillation at a reduced pressure to obtain (3E)-12,12-dimethoxy-3-dodecen-1-ol (2: $R^4$=$R^5$=$CH_3$; a=7) (53.21 g, 0.21 mol, purity 95.02%; 3Z: 3E=0: 100, bp=140.6 to 145.8° C./0.40 kPa (3.0 mmHg)) in a yield of 86.86%.

The following is the spectrum data of the (3E)-12,12-dimethoxy-3-dodecen-1-ol (2: $R^4$=$R^5$=$CH_3$; a=7) thus prepared.

[Nuclear magnetic resonance spectrum]: $^1$H-NMR (500 MHz, CDCl$_3$): δ=1.22-1.37 (10H, m), 1.53-1.60 (2H, m), 1.63 (1H, br. s), 1.98 (2H, q-like, J=7.3 Hz), 2.24 (2H, dt, J=6.1 Hz, 6.1H z), 3.29 (6H, s), 3.59 (2H, t, J=6.3 Hz), 4.33 (1H, t, J=5.7 Hz), 5.37 (1H, dtt, J=15.3 Hz, 7.2 Hz, 1.3 Hz), 5.48-5.56 (1H, m); $^{13}$C-NMR (500 MHz, CDCl$_3$): δ=24.49, 28.97, 29.29, 29.33, 32.39, 32.56, 35.92, 52.52, 61.98, 104.50, 125.72, 134.10.

[Mass spectrum]: EI-mass spectrum (70 eV): m/z 243 (M$^+$–1), 213, 182, 163, 150, 135, 121, 107, 95, 75, 55, 41, 29.

[Infrared absorption spectrum] (D-ATR): vmax=3417, 2926, 2854, 1464, 1386, 1128, 1053, 968.

Example 7

Preparation of (3E)-1-chloro-12,12-dimethoxy-3-dodecene (3: X=Cl, $R^4$=$R^5$=$CH_3$; a=7)

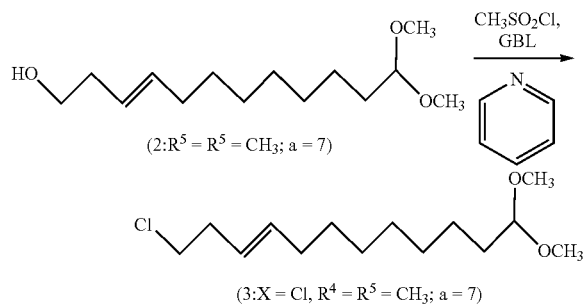

(3E)-12,12-Dimethoxy-3-dodecen-1-ol (2: $R^4$=$R^5$=$CH_3$; a=7) (31.79 g, 0.12 mol, purity 95.02%; 3Z: 3E=0: 100) obtained in Example 6, pyridine (19.82 g, 0.17 mol) and γ-butyrolactone (37.07 g) were placed in a reactor at room temperature and stirred at 0 to 10° C. for 32 minutes.

Subsequently, methanesulfonyl chloride (17.59 g, 0.22 mol) was added dropwise at 0 to 10° C. After the completion of the dropwise addition, the reaction mixture was heated to 60 to 65° C. and stirred for 12.5 hours. After the completion of the stirring, water (61.80 g) and hexane (61.80 g) were added to the reaction mixture, followed by phase separation. The aqueous phase was removed to obtain the organic phase. The organic phase thus obtained was washed with an aqueous acetic acid solution (acetic acid, 6.18 g and water, 61.80 g), then with an aqueous sodium hydrogen carbonate solution (sodium hydrogen carbonate, 3.09 g and water, 61.80 g). The organic phase was concentrated at a reduced pressure, and the concentrate was subjected to distillation at a reduced pressure to obtain (3E)-1-chloro-12,12-dimethoxy-3-dodecene (3: X=Cl, $R^4$=$R^5$=$CH_3$; a=7) (25.04 g, 0.089 mol, purity 93.81%, 3Z: 3E=0: 100, bp=136.2 to 147.2° C./0.40 kPa (3.0 mmHg)) in a yield of 72.30%.

The following is the spectrum data of the (3E)-1-chloro-12,12-dimethoxy-3-dodecene (3: X=Cl, $R^4$=$R^5$=$CH_3$; a=7) thus prepared.

[Nuclear magnetic resonance spectrum]: $^1$H-NMR (500 MHz, CDCl$_3$): δ=1.23-1.38 (10H, m), 1.54-1.61 (2H, m), 1.99 (2H, q-like, J=6.9 Hz), 2.43 (2H, ddt, J=1.1 Hz, 7.1 Hz, 7.1 Hz), 3.30 (6H, s), 3.49 (2H, t, J=6.9 Hz), 4.34 (1H, t, J=5.7 Hz), 5.38 (1H, dtt, J=15.3 Hz, 6.9 Hz, 1.5 Hz), 5.52 (1H, dtt, J=15.3 Hz, 6.9 Hz, 1.2 Hz); $^{13}$C-NMR (500 MHz, CDCl$_3$): δ=24.54, 28.95, 29.21, 29.33, 29.38, 32.45, 32.47, 35.87, 44.46, 52.54, 104.52, 125.47, 133.98.

[Mass spectrum]: EI-mass spectrum (70 eV): m/z 261 (M$^+$–1), 231, 194, 172, 157, 143, 95, 75, 55, 41, 27.

[Infrared absorption spectrum] (D-ATR): vmax=2927, 2855, 1463, 1127, 1055, 968, 722, 658.

Example 8

Preparation of (3E)-12,12-dimethoxy-1,3-dodecadiene (4: $R^4$=$R^5$=$CH_3$; a=7)

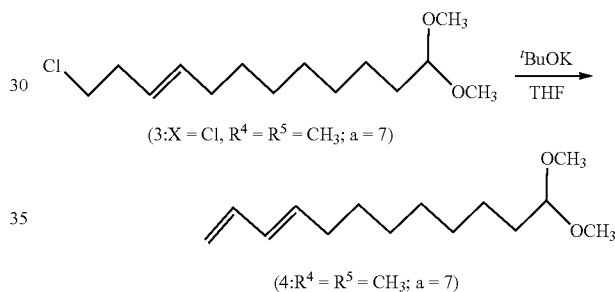

Potassium tert-butoxide (18.26 g, 0.16 mol) and tetrahydrofuran (71.49 g) were placed in a reactor at room temperature and stirred at −5 to 5° C. for 17 minutes.

Subsequently, (3E)-1-chloro-12,12-dimethoxy-3-dodecene (3: X=Cl, $R^4$=$R^5$=$CH_3$; a=7) (25.04 g, 0.089 mol, purity 93.81%, 3Z: 3E=0: 100) obtained in Example 7 was added dropwise at 0 to 10° C. After the completion of the dropwise addition, the reaction mixture was heated to 20 to 25° C. and stirred for 7.5 hours. After the completion of the stirring, water (26.81 g) was added to the reaction mixture, followed by phase separation. The aqueous phase was removed to obtain the organic phase. The organic phase thus obtained was concentrated at a reduced pressure to obtain a crude product, (3E)-12,12-dimethoxy-1,3-dodecadiene (4: $R^4$=$R^5$=$CH_3$; a=7), (25.29 g, 0.094 mol, purity 84.79%; 3Z: 3E=0: 100) quantitatively.

The following is the spectrum data of the (3E)-12,12-dimethoxy-1,3-dodecadiene (4: $R^4$=$R^5$=$CH_3$; a=7) thus prepared.

[Nuclear magnetic resonance spectrum]: $^1$H-NMR (500 MHz, CDCl$_3$): δ=1.25-1.43 (10H, m), 1.54-1.61 (2H, m), 2.06 (2H, dt, J=6.9 Hz, 6.9 Hz), 3.30 (6H, s), 4.35 (1H, t, J=5.7 Hz), 4.93 (1H, dd, J=9.8H z, 1.1 Hz), 5.07 (1H, dd, J=17.4 Hz, 1.1 Hz), 5.69 (1H, dt, J=6.9 Hz, 6.9 Hz), 6.03 (1H, dd, J=15.1 Hz, 10.3 Hz), 6.29 (1H, ddd, J=16.8 Hz, 10.3 Hz, 10.3 Hz); $^{13}$C-NMR (500 MHz, CDCl$_3$): δ=24.54, 29.04, 29.11, 29.35, 29.37, 32.44, 32.48, 52.53, 104.51, 114.54, 130.84, 135.49, 137.31.

[Mass spectrum]: EI-mass spectrum (70 eV): m/z 225 (M+−1), 195, 163, 121, 107, 95, 75, 55, 41.
[Infrared absorption spectrum] (D-ATR): vmax=2927, 2855, 1464, 1126, 1056, 1003, 951, 897.

Example 9

Preparation of (9E)-9,11-dodecadienal (5: a=7)

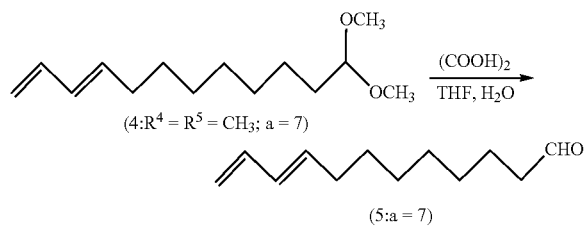

The crude product, (3E)-12,12-dimethoxy-1,3-dodecadiene (4: R⁴=R⁵=CH₃; a=7), (25.29 g, 0.094 mol, purity 84.79%; 3Z: 3E=0: 100), oxalic acid dihydrate (35.58 g, 0.28 mol), tetrahydrofuran (94.07 g) and pure water (94.07 g) were placed in a reactor at room temperature and stirred at 60 to 65° C. for 2 hours.

Subsequently, the reaction mixture was cooled to 50° C., and hexane (27.67 g) was added, and the reaction mixture was stirred for 45 minutes. After the completion of the stirring, the reaction mixture was allowed to stand for phase separation. The aqueous phase was removed to obtain the organic phase. The organic phase thus obtained was concentrated at a reduced pressure, and the concentrate was subjected to distillation at a reduced pressure to obtain (9E)-9,11-dodecadienal (5: a=7) (16.22 g, 0.085 mol, purity 94.76%, 3Z: 3E=0: 100, bp=112.1 to 118.3° C./0.40 kPa (3.0 mmHg)) in an overall yield of of Examples 8 and 9, i.e., two steps, of 95.40% The geometry at position 3 of (3E)-12,12-diethoxy-3-dodecenyl methoxymethyl ether (1: R¹=H, R²=R³=CH₂CH₃; a=7) was maintained in the geometry at position 9 of (9E)-9,11-dodecadienal (5: a=7). Thus, no isomerization was found.

The following is the spectrum data of the (9E)-9,11-dodecadienal (5: a=7) thus prepared.

[Nuclear magnetic resonance spectrum]: ¹H-NMR (500 MHz, CDCl₃): δ=1.26-1.34 (6H, m), 1.31-1.41 (2H, m), 1.61 (2H, quin-like, J=7.3 Hz), 2.06 (2H, tt, J=6.9 Hz, 6.9 Hz), 2.41 (2H, dt, J=7.5 Hz, 1.9 Hz), 4.94 (1H, d, J=9.9 Hz), 5.07 (1H, d, J=17.6 Hz), 5.68 (1H, ddd, J=15.3 Hz, 7.3 Hz, 7.3 Hz), 6.03 (1H, dd, J=15.3 Hz, 10.3 Hz), 6.29 (1H, dt, J=17.2 Hz, 10.3 Hz), 9.75 (1H, t, J=1.9 Hz); ¹³C-NMR (500 MHz, CDCl₃): δ=21.98, 28.88, 29.02, 29.13, 32.42, 43.84, 114.60, 130.90, 135.33, 137.25, 202.79.

[Mass spectrum] : EI-mass spectrum (70 eV) : m/z 180 (M+), 151, 137, 123, 112, 98, 81, 67, 54, 41, 29.
[Infrared absorption spectrum] (D-ATR): vmax=2928, 2855, 1726, 1464, 1004, 951, 897.

Example 10

Preparation of (9E)-9,11-dodecadienal (5: a=7)

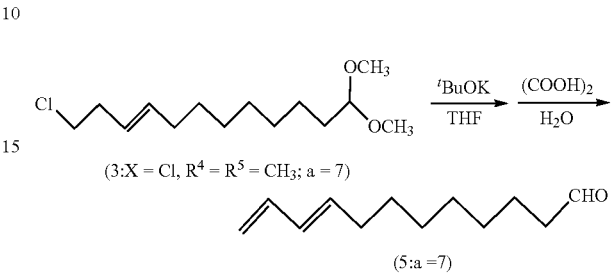

Potassium tert-butoxide (184.15 g, 1.64 mol) and tetrahydrofuran (573.84 g) were placed in a reactor at room temperature and stirred at −5 to 5° C. for 12 minutes.

Subsequently, (3E)-1-chloro-12,12-dimethoxy-3-dodecene (3: X=Cl, R⁴=R⁵=CH³; a=7) (216.02 g, 0.72 mol, purity 87.27%) obtained as in Example 7 was added dropwise at 0 to 10° C. After the completion of the dropwise addition, the reaction mixture was heated to 20 to 25° C. and stirred for 5 hours. After the completion of the stirring, water (458.65 g) was added, followed by phase separation. The aqueous phase was removed to obtain the organic phase. Oxalic acid dihydrate (135.65 g, 1.08 mol), tetrahydrofuran (143.46 g) and pure water (717.30 g) were added to the obtained organic layer, and the reaction mixture was stirred at 60 to 65° C. for 2 hours (washing step). Then, the reaction mixture was cooled to 50° C., and hexane (210.96 g) was added, and the reaction mixture was stirred for 63 minutes. After the completion of the stirring, the reaction mixture was allowed to stand for phase separation. The aqueous phase was removed to obtain the organic phase. The organic phase thus obtained was concentrated at a reduced pressure, and the concentrate was subjected to distillation at a reduced pressure to obtain (9E)-9,11-dodecadienal (5: a=7) (137.32 g, 0.65 mol, purity 85.77%, bp=100.6 to 112.1° C./0.40 kPa (3.0 mmHg)) in a yield of 91.07%. The various spectrum data of the (9E)-9,11-dodecadienal (5: a=7) thus prepared were same as those obtained in Example 9.

Example 11

Preparation of (3Z)-12,12-dimethoxy-3-dodecen-1-ol (2: R⁴=R⁵=CH₃; a=7)

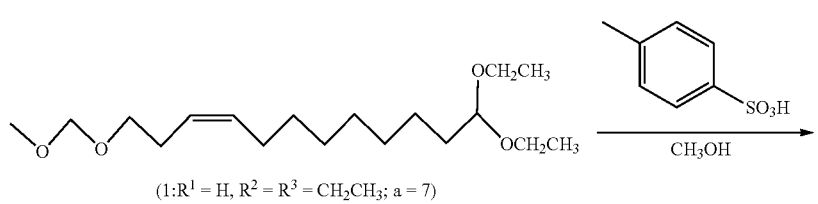

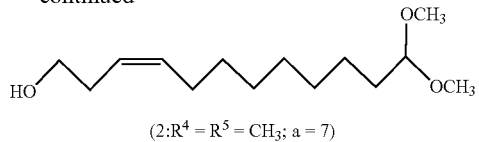

(2: $R^4 = R^5 = CH_3$; a = 7)

(3Z)-12,12-Diethoxy-3-dodecenyl methoxymethyl ether (1: $R^1$=H, $R^2$=$R^3$=$CH_2CH_3$; a=7) (907.41 g, 2.71 mol, purity 92.59%; 3Z: 3E=95.7: 4.3) obtained in Example 2, methanol (2655.00 g, 82.87 mol) and p-toluenesulfonic acid monohydrate (15.15 g, 0.080 mol) were placed in a reactor equipped with a distillation column, and the reaction mixture was heated to 60° C. and stirred for 10 hours. After the completion of the stirring, the internal temperature was raised to 65 to 70° C., and a mixture of dimethoxymethane by-produced and methanol was distilled off from the distillation column. The reaction mixture was sampled during the reaction. When the conversion ratio reached 100%, an aqueous 25% by mass sodium hydroxide solution (25.49 g, 0.16 mol as sodium hydroxide) was added, and methanol was removed until no distillate emerged. Then, water (200 g) and hexane (324.92 g) were added, followed by phase separation. The aqueous phase was removed to obtain the organic phase. The organic phase thus obtained was concentrated at a reduced pressure to obtain (3Z)-12,12-dimethoxy-3-dodecen-1-ol (2: $R^4$=$R^5$=$CH_3$; a=7) (689.37 g, 2.59 mol, purity 91.89%; 3Z: 3E=95.4: 4.6) in a crude yield of 95.71%.

The following is the spectrum data of the (3Z)-12,12-dimethoxy-3-dodecen-1-ol (2: $R^4$=$R^5$=$CH_3$; a=7) thus prepared.

[Nuclear magnetic resonance spectrum]: $^1$H-NMR (500 MHz, CDCl$_3$): δ=1.23-1.37 (10H, m), 1.53-1.60 (2H, m), 1.63 (1H, br. s), 2.04 (2H, q-like, J=6.9 Hz), 2.31 (2H, q-like, J=6.9 Hz), 3.29 (6H, s), 3.61 (2H, t, J=6.7 Hz), 4.34 (1H, t, J=5.7 Hz), 5.34 (1H, dtt, J=11.1 Hz, 7.3 Hz, 1.5 Hz), 5.49-5.57 (1H, m); $^{13}$C-NMR (500 MHz, CDCl$_3$): δ=24.51, 27.27, 29.09, 29.35, 29.58, 30.76, 32.40, 52.53, 62.25, 104.50, 124.98, 133.30.

[Mass spectrum]: EI-mass spectrum (70 eV): m/z 243 (M$^+$-1), 213, 182, 163, 150, 135, 121, 107, 75, 55, 41, 29.

[Infrared absorption spectrum] (D-ATR): vmax=3429, 2926, 1464, 1386, 1128, 1053, 723.

Example 12

Preparation of (3Z)-1-chloro-12,12-dimethoxy-3-dodecene (3: X=Cl, $R^4$=$R^5$=$CH_3$; a=7)

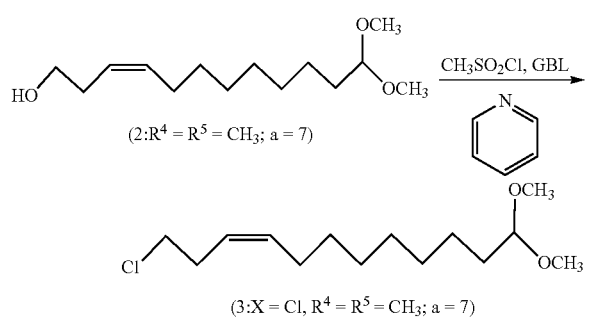

(3Z)-12,12-Dimethoxy-3-dodecen-1-ol (2: $R^4$=$R^5$=$CH_3$; a=7) (689.37 g, 2.59 mol, purity 91.89%; 3Z: 3E=95.4: 4.6) obtained in Example 11, pyridine (369.06 g, 4.67 mol) and γ-butyrolactone (777.63 g) were placed in a reactor at room temperature and stirred at 0 to 10° C. for 23 minutes.

Subsequently, methanesulfonyl chloride (415.69 g, 3.63 mol) was added dropwise at 0 to 10° C. After the completion of the dropwise addition, the reaction mixture was heated to 60 to 65° C. and stirred for 8 hours. After the completion of the stirring, water (777.63 g) and hexane (777.63 g) were added to the reaction mixture, followed by phase separation. The aqueous phase was removed to obtain the organic phase. The organic phase thus obtained was washed with an aqueous acetic acid solution (acetic acid, 7.78 g and water, 777.63 g), and then with an aqueous sodium hydrogen carbonate solution (sodium hydrogen carbonate, 7.78 g and water, 777.3 g). The organic phase was concentrated at a reduced pressure, and the concentrate was subjected to distillation at a reduced pressure to obtain (3Z)-1-chloro-12,12-dimethoxy-3-dodecene (3: X=Cl, $R^4$=$R^5$=$CH_3$; a=7) (478.35 g, 1.66 mol, purity 91.37%; 3Z: 3E=95.5: 4.5, bp=130.1 to 145.9° C./0.40 kPa (3.0 mmHg)) in an oveall yield of Examples 11 and 12, i.e., two steps, of 61.46%.

The following is the spectrum data of the (3Z)-1-chloro-12,12-dimethoxy-3-dodecene (3: X=Cl, $R^4$=$R^5$=$CH_3$; a=7) thus prepared.

[Nuclear magnetic resonance spectrum]: $^1$H-NMR (500 MHz, CDCl$_3$): δ=1.25-1.38 (10H, m), 1.54-1.61 (2H, m), 2.03 (2H, q-like, J=6.9 Hz), 2.50 (2H, dt, J=7.1 Hz, 7.1 Hz), 3.30 (6H, s) 3.49 (2H, t, J=7.3 Hz), 4.34 (1H, t, J=5.8 Hz), 5.36 (1H, dtt, J=10.7 Hz, 7.2 Hz, 1.9 Hz), 5.51 (1H, dtt, J=10.7 Hz, 7.3 Hz, 1.5 Hz); $^{13}$C-NMR (500 MHz, CDCl$_3$): δ=24.54, 27.33, 29.11, 29.37, 29.44, 30.66, 32.45, 44.21, 52.54, 104.51, 124.81, 133.20.

[Mass spectrum]: EI-mass spectrum (70 eV): m/z 261 (M$^+$-1), 231, 172, 157, 143, 95, 75, 55, 41, 27.

[Infrared absorption spectrum] (D-ATR): vmax=2927, 2855, 1463, 1127, 1055, 725, 662.

Example 13

Preparation of (3Z)-12,12-dimethoxy-1,3-dodecadiene (4: $R^4$=$R^5$=$CH_3$; a=7)

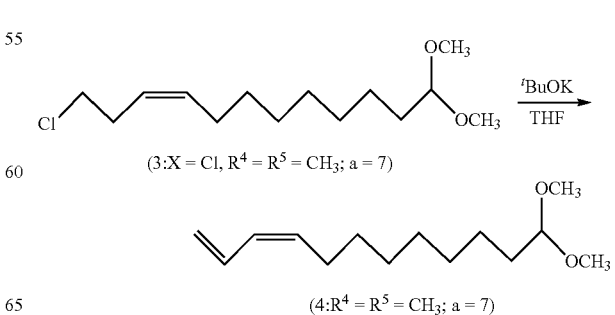

Potassium tert-butoxide (373.21 g, 3.33 mol) and tetrahydrofuran (1380.40 g) were placed in a reactor at room temperature and stirred at -5 to 5° C. for 40 minutes.

Subsequently, (3Z)-1-chloro-12,12-dimethoxy-3-dodecene (3: X=Cl, $R^4$=$R^5$=$CH_3$; a=7) (478.35 g, 1.66 mol, purity 91.37%; 3Z: 3E=95.5: 4.5) obtained in Example 12 was added dropwise at 0 to 10° C. After the completion of the dropwise addition, the reaction mixture was heated to 20 to 25° C. and stirred for 5 hours. After the completion of the stirring, water (798.90 g) was added, followed by phase separation. The aqueous phase was removed to obtain the organic phase. The organic phase thus obtained was concentrated at a reduced pressure to obtain a crude product, (3Z)-12,12-dimethoxy-1,3-dodecadiene (4: $R^4$=$R^5$=$CH_3$; a=7), (416.26 g, 1.56 mol, purity 84.89%) in a crude yield of 93.87%.

The following is the spectrum data of the (3Z)-12,12-dimethoxy-1,3-dodecadiene (4: $R^4$=$R^5$=$CH_3$; a=7) thus prepared.

[Nuclear magnetic resonance spectrum]: $^1$H-NMR (500 MHz, $CDCl_3$): δ=1.24-1.41 (10H, m), 1.54-1.61 (2H, m), 2.17 (2H, ddt, J=1.2 Hz, 7.5 Hz, 7.5 Hz), 3.30 (6H, s), 4.35 (1H, t, J=5.7 Hz), 5.07 (1H, d, J=10.3 Hz), 5.16 (1H, dd, J=17.0 Hz, 1.9 Hz), 5.44 (1H, q-like, J=7.7 Hz), 5.98 (1H, dd, J=10.7 Hz, 10.7 Hz), 6.62 (1H, dddd, J=16.8 Hz, 10.5 Hz, 10.5 Hz, 1.1 Hz); $^{13}$C-NMR (500 MHz, $CDCl_3$): δ=24.54, 27.66, 29.07, 29.36, 29.38, 29.53, 32.44, 52.53, 104.51, 116.65, 129.10, 132.28, 132.95.

[Mass spectrum]: EI-mass spectrum (70 eV): m/z 226 ($M^+$), 195, 163, 121, 95, 75, 41.

[Infrared absorption spectrum] (D-ATR): vmax=2927, 2855, 1464, 1385, 1126, 1056, 997, 902.

Example 14

Preparation of (9Z)-9,11-dodecadienal (5: a=7)

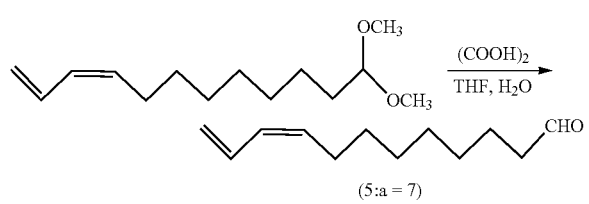

(5:a = 7)

The crude product, (3Z)-12,12-dimethoxy-1,3-dodecadiene (4: $R^4$=$R^5$=$CH_3$; a=7), (416.26 g, 1.56 mol, purity 84.89%), obtained in Example 13, oxalic acid dihydrate (628.96 g, 4.99 mol), tetrahydrofuran (1663.00 g) and pure water (1663.00 g) were placed in a reactor at room temperature and stirred at 60 to 65° C. for 4 hours. The reaction mixture was cooled to 50° C., and hexane (4.09 g) was added and stirred for 47 minutes. After the completion of the stirring, the reaction mixture was allowed to stand for phase separation. The aqueous phase was removed to obtain the organic phase. The organic phase thus obtained was concentrated at a reduced pressure, and the concentrate was subjected to distillation at a reduced pressure to obtain (9Z)-9,11-dodecadienal (5: a=7) (20.75 g, 1.53 mol, purity 97.71%, 3Z: 3E=95.7: 4.3, bp=108.0 to 113.9° C./0.40 kPa (3.0 mmHg)) in an overall yield of Examples 13 and 14 of 91.73%. The geometry at position 3 of diethoxydodecenyl methoxymethyl ether (1: $R^1$=H, $R^2$=$R^3$=$CH_2CH_3$; a=7) was maintained in the geometry at position 9 of (9Z)-9,11-dodecadienal (5: a=7). Thus, no isomerization was found.

The following is the spectrum data of the (9Z)-9,11-dodecadienal (5: a=7) thus prepared.

[Nuclear magnetic resonance spectrum]: $^1$H-NMR (500 MHz, $CDCl_3$): δ=1.25-1.33 (6H, m), 1.33-1.41 (2H, m), 1.61 (2H, quin-like, J=7.3 Hz), 2.17 (2H, ddt, J=1.5 Hz, 7.6 Hz, 7.6 Hz), 2.41 (2H, dt, J=1.9 Hz, 7.3 Hz), 5.07 (1H, d, J=9.9 Hz), 5.17 (1H, dd, J=16.8 Hz, 1.9 Hz), 5.43 (1H, dd, J=16.8 Hz, 1.9 Hz), 5.98 (1H, dd, J=10.7 Hz, 10.7 Hz), 6.62 (1H, dddd, J=16.8 Hz, 10.5 Hz, 10.5 Hz, 1.1 Hz), 9.75 (1H, t, J=1.9 Hz); $^{13}$C-NMR (500 MHz, $CDCl_3$): δ=21.99, 27.60, 28.90, 29.04, 29.13, 29.43, 43.84, 116.72, 129.17, 132.24, 132.79, 202.78.

[Mass spectrum]: EI-mass spectrum (70 eV): m/z 180 ($M^+$), 151, 137, 123, 112, 98, 81, 67, 54, 41, 29.

[Infrared absorption spectrum] (D-ATR): vmax=2928, 2855, 1726, 1464, 999, 903, 657, 613.

Example 15

Preparation of (3Z)-7,7-dimethoxy-3-hepten-1-ol (2: $R^4$=$R^5$=$CH_3$; a=2)

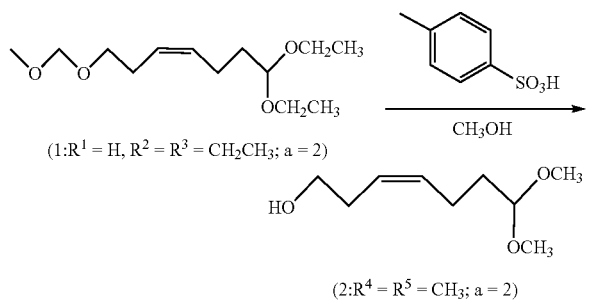

(3Z)-7,7-diethoxy-3-heptenyl methoxymethyl ether (1: $R^1$=H, $R^2$=$R^3$=$CH_2CH_3$; a=2) (69.52 g, 0.27 mol, purity 94.37%; 3Z: 3E=90.6: 9.4) obtained as in Example 5, methanol (853.23 g, 26.63 mol) and p-toluenesulfonic acid monohydrate (2.53 g, 0.01 mol) were placed in a reactor equipped with a distillation column, and the reaction mixture was heated to 60° C. and stirred for 5.5 hours. After the completion of the stirring, the internal temperature was raised to 65 to 70° C., and a mixture of dimethoxymethane by-produced and methanol was distilled off from the distillation column. The reaction mixture was sampled during the reaction, and when the reaction rate reached 100%, an aqueous 25% by mass sodium hydroxide solution (4.26 g, 0.027 mol as sodium hydroxide) was added, and methanol was removed until no distillate emerged. Then, water (30 g) was added, followed by phase separation. The aqueous phase was removed to obtain the organic phase. The organic phase thus obtained was concentrated at a reduced pressure to obtain (3Z)-7,7-dimethoxy-3-hepten-1-ol (2: $R^4$=$R^5$=$CH_3$; a=2) (43.20 g, 0.24 mol, purity 95.76%; 3Z: 3E=90.4: 9.6, bp=110.0 to 116.0° C./3.0 mmHg) in a yield of 89.16%.

The following is the spectrum data of the (3Z)-7,7-dimethoxy-3-hepten-1-ol (2: $R^4$=$R^5$=$CH_3$; a=2) thus prepared.

[Nuclear magnetic resonance spectrum]: $^1$H-NMR (500 MHz, $CDCl_3$): δ=1.65 (2H, dt, J=6.9 Hz, 6.9 Hz), 1.95 (1H, br. s), 2.11 (2H, dt, J=7.5 Hz, 7.5 Hz), 2.31 (2H, dt, J=6.8 Hz, 6.8 Hz), 3.29 (6H, s), 3.61 (2H, t, J=6.5 Hz), 4.36 (1H, t, J=5.9 Hz), 5.36-5.43 (1H, m), 5.47-5.54 (1H, m); $^{13}$C-NMR (500 MHz, CDCl$_3$): δ=22.45, 30.67, 31.90, 52.47, 62.10, 103.64, 126.18, 131.67.

[Infrared absorption spectrum] (D-ATR): vmax=3415, 2946, 1448, 1385, 1128, 1055, 918, 729.

Example 16

Preparation of (3Z)-1-chloro-7,7-dimethoxy-3-heptene (3: X=Cl, R$^4$=R$^5$=CH$_3$; a=2)

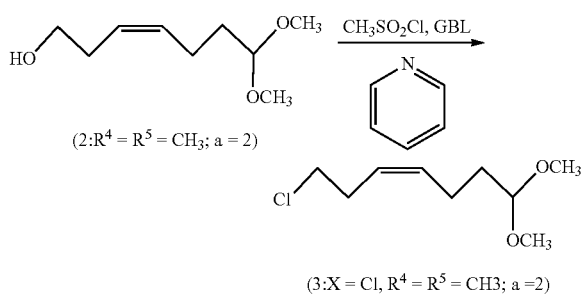

(3Z)-7,7-Dimethoxy-3-hepten-1-ol (2: R$^4$=R$^5$=CH$_3$; a=2) (178.00 g, 0.68 mol, purity 94.77%; 3Z: 3E=89.6: 10.4) obtained as in Example 15, pyridine (70.85 g, 0.90 mol), potassium carbonate (13.75 g, 0.10 mol) and γ-butyrolactone (GBL) (149.28 g) were placed in a reactor at room temperature and stirred at 0 to 10° C. for 18 minutes.

Subsequently, methanesulfonyl chloride (79.80 g, 0.70 mol) was added dropwise at 0 to 10° C. After the completion of the dropwise addition, the reaction mixture was heated to 60 to 65° C. and stirred for 5.5 hours. After the completion of the stirring, water (199.04 g) and hexane (199.04 g) were added to the reaction mixture, followed by phase separation. The aqueous phase was removed to obtain the organic phase. The organic phase thus obtained was washed with an aqueous acetic acid solution (acetic acid, 24.48 g and water, 199.04 g), and then with an aqueous sodium hydrogen carbonate solution (sodium hydrogen carbonate, 12.56 g and water, 199.04 g). The organic phase was concentrated at a reduced pressure, and the concentrate was subjected to distillation at a reduced pressure to obtain (3Z)-1-chloro-7, 7-dimethoxy-3-heptene (3: X=Cl, R$^4$=R$^5$=CH$_3$; a=2) (62.54 g, 0.30 mol, purity 91.97%; 3Z: 3E=89.5: 10.5, bp=73.2 to 74.0° C./3.0 mmHg) in a yield of 60.00%.

The following is the spectrum data of the (3Z)-1-chloro-7,7-dimethoxy-3-heptene (3: X=Cl, R$^4$=R$^5$=CH$_3$; a=2) thus prepared.

[Nuclear magnetic resonance spectrum]: $^1$H-NMR (500 MHz, CDCl$_3$): δ=1.62-1.69 (2H, m), 2.10 (2H, dt, J=7.9 Hz, 7.9 Hz), 2.52 (2H, dt, J=6.9 Hz, 6.9 Hz), 3.31 (6H, s), 3.50 (2H, t, J=6.9 Hz), 4.35 (1H, t, J=5.7 Hz) 5.37-5.44 (1H, m), 5.48-5.55 (1H, m); $^{13}$C-NMR (500 MHz, CDCl$_3$): δ=22.55, 30.51, 32.10, 44.12, 52.78, 103.79, 125.67, 131.88.

[Mass spectrum]: EI-mass spectrum (70 eV): m/z 191 (M$^+$-1), 161, 143, 129, 97, 75, 58, 41.

[Infrared absorption spectrum] (D-ATR): vmax=2952, 2830, 1447, 1385, 1295, 1127, 1066, 918, 737, 660.

Example 17

Preparation of (3Z)-7,7-dimethoxy-1,3-heptadiene (4: R$^4$=R$^5$=CH$_3$; a=2)

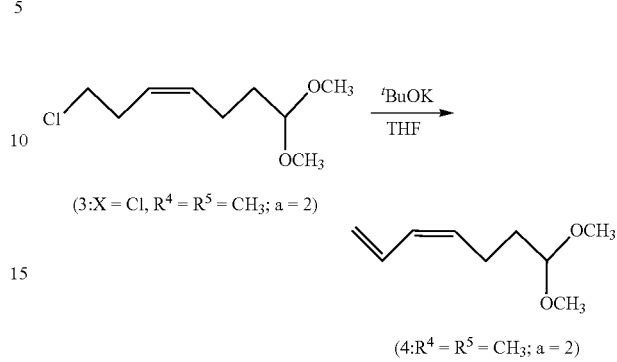

Potassium tert-butoxide (47.33 g, 0.42 mol) and tetrahydrofuran (198.48 g) were placed in a reactor at room temperature and stirred at −5 to 5° C. for 17 minutes.

Subsequently, (3Z)-1-chloro-7,7-dimethoxy-3-heptene (3: X=Cl, R$^4$=R$^5$=CH$_3$; a=2) (51.98 g, 0.25 mol, purity 91.97%; 3Z: 3E=89.5: 10.5) obtained in Example 16 was added dropwise at 0 to 10° C. After the completion of the dropwise addition, the reaction mixture was heated to 20 to 25° C. and stirred for 1.5 hours. After the completion of the stirring, water (125.43 g) was added, followed by phase separation. The aqueous phase was removed to obtain the organic phase. The organic phase thus obtained was concentrated at a reduced pressure to obtain a crude product, (3Z)-7,7-dimethoxy-1,3-heptadiene (4: R$^4$=R$^5$=CH$_3$; a=2), (74.28 g, 0.26 mol, purity 55.13%; 3Z: 3E=89.5: 10.5) in a crude yield of 100%.

The following is the spectrum data of the (3Z)-7,7-dimethoxy-1,3-heptadiene (4: R$^4$=R$^5$=CH$_3$; a=2) thus prepared.

[Nuclear magnetic resonance spectrum]: $^1$H-NMR (500 MHz, CDCl$_3$): δ=1.68 (2H, dt, J=5.7 Hz, 7.6 Hz), 2.24 (2H, ddt, J=1.5 Hz, 7.7 Hz, 7.7 Hz), 3.31 (6H, s), 4.35 (1H, t, J=5.7 Hz), 5.09 (1H, d, J=9.9 Hz), 5.18 (1H, dd, J=16.8 Hz, 1.9 Hz), 5.43 (1H, dt, J=7.7 Hz, 7.7 Hz), 6.01 (1H, dd, J=10.7 Hz, 10.7 Hz), 6.64 (1H, dddd, J=16.9 Hz, 10.6 Hz, 10.6 Hz, 1.1 Hz); LC-NMR (500 MHz, CDCl$_3$): δ=22.90, 32.20, 52.76, 103.82, 117.21, 129.82, 131.35, 132.00.

[Mass spectrum]: EI-mass spectrum (70 eV): m/z 155 (M$^+$-1), 124, 93, 75, 58, 41.

[Infrared absorption spectrum] (D-ATR): vmax=2950, 2830, 1436, 1385, 1365, 1126, 1080, 1065, 903, 788, 667.

Example 18

Preparation of (4Z)-4,6-heptadienal (5: a=2)

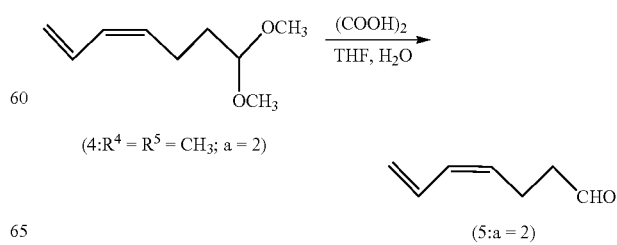

The crude product, (3Z)-7,7-dimethoxy-1,3-heptadiene (4: $R^4=R^5=CH_3$; a=2), (74.28 g, 0.26 mol, purity 55.13%; 3Z: 3E=89.5: 10.5) obtained in Example 17, oxalic acid dihydrate (93.83 g, 0.74 mol), tetrahydrofuran (248.10 g) and pure water (248.10 g) were placed in a reactor at room temperature and stirred at 60 to 65° C. for 2 hours. After the completion of the stirring, the reaction mixture was cooled to 50° C., hexane (726.70 g) was added, and the reaction mixture was stirred for 48 minutes. After the completion of the stirring, the reaction mixture was allowed to stand for phase separation. The aqueous phase was removed to obtain the organic phase. The organic phase thus obtained was concentrated at a reduced pressure, and the concentrate was subjected to distillation at a reduced pressure to obtain (4Z)-4,6-heptadienal (5: a=2) (20.75 g, 0.18 mol, purity 97.71%, 3Z: 3E=89.8: 10.2, bp=58.9-59.0° C./8.00 kPa (60.0 mmHg)) in an overall yield of Examples 17 and 18 of 74.20%. The geometry at position 3 of (3Z)-7,7-dimethoxy-3-hepten-1-ol (2: $R^4=R^5=CH_3$; a=2) was maintained in the geometry at position 4 of (4Z)-4,6-heptadienal (5: a=2). Thus, no isomerization was found.

The following is the spectrum data of the (4Z)-4,6-heptadienal (5: a=2) thus prepared.

[Nuclear magnetic resonance spectrum]: $^1$H-NMR (500 MHz, CDCl$_3$): δ=2.47-2.56 (4H, m), 5.13 (1H, d, J=10.4 Hz), 5.21 (1H, dd, J=16.8 Hz, 1.9 Hz), 5.36-5.43 (1H, m), 6.02 (1H, dd, J=10.7 Hz, 10.7 Hz), 6.62 (1H, dddd, J=18.7 Hz, 10.7 Hz, 10.7 Hz, 1.1 Hz), 9.76 (1H, d, J=1.6 Hz); $^{13}$C-NMR (500 MHz, CDCl$_3$): δ=20.38, 43.50, 118.00, 129.61, 130.42, 131.53, 201.57.

[Mass spectrum]: EI-mass spectrum (70 eV): m/z 110 (M$^+$), 95, 82, 67, 54, 41, 27.

[Infrared absorption spectrum] (D-ATR): vmax=2825, 2726, 1725, 1437, 1409, 1000, 908, 786, 648.

The invention claimed is:

1. A process for preparing a terminal conjugated alkadienal compound of the following general formula (5):

$$CH_2=CHCH=CH(CH_2)_aCHO \quad (5)$$

wherein "a" represents an integer of 1 to 15, the process comprising:
dealkoxymethylating a dialkoxyalkenyl alkoxymethyl ether compound of the following general formula (1):

$$R^1CH_2OCH_2OCH_2CH_2CH=CH(CH_2)_aCH(OR^2)(OR^3) \quad (1)$$

wherein $R^1$ represents a hydrogen atom, an n-alkyl group having 1 to 9 carbon atoms, or a phenyl group, $R^2$ and $R^3$ represent, independently of each other, a monovalent hydrocarbon group having 1 to 15 carbon atoms, or $R^2$ and $R^3$ may form together a divalent hydrocarbon group, $R^2$-$R^3$, having 2 to 10 carbon atoms, and "a" is as defined above,
to prepare a dialkoxy-3-alken-1-ol compound of the following general formula (2):

$$HOCH_2CH_2CH=CH(CH_2)_aCH(OR^4)(OR^5) \quad (2)$$

wherein $R^4$ and $R^5$ represent, independently of each other, a monovalent hydrocarbon group having 1 to 15 carbon atoms, or $R^4$ and $R^5$ may form together a divalent hydrocarbon group, $R^4$-$R^5$, having 2 to 10 carbon atoms, and "a" is as defined above;
halogenating the dialkoxy-3-alken-1-ol compound (2) to prepare a 1-halodialkoxy-3-alkene compound of the following general formula (3):

$$XCH_2CH_2CH=CH(CH_2)_aCH(OR^4)(OR^5) \quad (3)$$

wherein X represents a halogen atom, and $R^4$, $R^5$ and "a" are as defined above;
subjecting the 1-halodialkoxy-3-alkene compound (3) to an elimination reaction in the presence of a base to prepare a dialkoxy-1,3-alkadiene compound of the following general formula (4):

$$CH_2=CHCH=CH(CH_2)_aCH(OR^4)(OR^5) \quad (4)$$

wherein $R^4$, $R^5$ and "a" are as defined above; and
hydrolyzing the dialkoxy-1,3-alkadiene compound (4) to obtain the terminal conjugated alkadienal compound (5).

2. The process for preparing the terminal conjugated alkadienal compound (5) according to claim 1, wherein the hydrolysis is carried out in a washing step after the elimination reaction.

3. A dialkoxyalkenyl alkoxymethyl ether compound of the following general formula (1):

$$R^1CH_2OCH_2OCH_2CH_2CH=CH(CH_2)_aCH(OR^2)(OR^3) \quad (1)$$

wherein $R^1$ represents a hydrogen atom, an n-alkyl group having 1 to 9 carbon atoms, or a phenyl group, $R^2$ and $R^3$ represent, independently of each other, a monovalent hydrocarbon group having 1 to 15 carbon atoms, or $R^2$ and $R^3$ may foam together a divalent hydrocarbon group, $R^2$-$R^3$, having 2 to 10 carbon atoms, and "a" represents an integer of 1 to 15.

4. The dialkoxyalkenyl alkoxymethyl ether compound (1) according to claim 3, wherein "a" represents an integer of 7.

* * * * *

UNITED STATES PATENT AND TRADEMARK OFFICE
CERTIFICATE OF CORRECTION

PATENT NO. : 11,414,368 B2
APPLICATION NO. : 17/489898
DATED : August 16, 2022
INVENTOR(S) : Miyake et al.

It is certified that error appears in the above-identified patent and that said Letters Patent is hereby corrected as shown below:

On the Title Page

Item (57) Abstract, Lines 8-9: Please delete formula (I) and replace with the following:
$R^1CH_2OCH_2OCH_2CH_2CH = CH(CH_2)_aCH(OR^2)(OR^3)$ In the Specification Column 2, Line 28: Please correct "Z-foam" to read --Z-form--

Column 2, Lines 62-63: Please delete formula (I) and replace with the following:
$R^1CH_2OCH_2OCH_2CH_2CH = CH(CH_2)_aCH(OR^2)(OR^3)$ Column 3, Lines 31-32: Please delete formula (I) and replace with the following:
$R^1CH_2OCH_2OCH_2CH_2CH = CH(CH_2)_aCH(OR^2)(OR^3)$ Column 60, Line 26: Please correct "$CH^3$" to read --$CH_3$--

Column 63, Lines 41-48, Example 14: Please delete the reaction scheme and replace with the following:

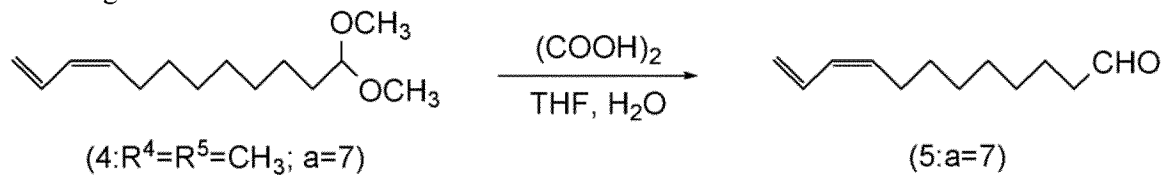

Column 66, Line 46: Please correct "LC-NMR" to read --$^{13}$C-NMR--

Signed and Sealed this
Twenty-seventh Day of June, 2023

Katherine Kelly Vidal
*Director of the United States Patent and Trademark Office*

CERTIFICATE OF CORRECTION (continued)
U.S. Pat. No. 11,414,368 B2

In the Claims

Column 67, Lines 45-46, Claim 1: Please delete formula (I) and replace with the following:
$R^1CH_2OCH_2OCH_2CH_2CH = CH(CH_2)_aCH(OR^2)(OR^3)$ Column 68, Lines 37-38, Claim 3: Please delete formula (I) and replace with the following:
$R^1CH_2OCH_2OCH_2CH_2CH = CH(CH_2)_aCH(OR^2)(OR^3)$ Column 68, Line 43, Claim 3: Please correct "foam" to read --form--